(12) United States Patent
Mou et al.

(10) Patent No.: US 12,037,409 B2
(45) Date of Patent: Jul. 16, 2024

(54) ANTIBODY SPECIFICALLY BOUND TO GLYCOSYLATED CEACAM5

(71) Applicant: SHANGHAI GENBASE BIOTECHNOLOGY CO., LTD., Shanghai (CN)

(72) Inventors: Nan Mou, Shanghai (CN); Yue Yu, Shanghai (CN); Jijun Yuan, Shanghai (CN)

(73) Assignee: Shanghai Genbase Biotechnology Co., Ltd., Shanghai (CN)

( * ) Notice: Subject to any disclaimer, the term of this patent is extended or adjusted under 35 U.S.C. 154(b) by 0 days.

(21) Appl. No.: 18/022,113

(22) PCT Filed: Jan. 8, 2021

(86) PCT No.: PCT/CN2021/070825
§ 371 (c)(1),
(2) Date: Feb. 17, 2023

(87) PCT Pub. No.: WO2022/037002
PCT Pub. Date: Feb. 24, 2022

(65) Prior Publication Data
US 2023/0331862 A1    Oct. 19, 2023

(30) Foreign Application Priority Data
Aug. 21, 2020    (WO) ................ PCT/CN2020/110514

(51) Int. Cl.
| | | |
|---|---|---|
| *C07K 16/00* | (2006.01) | |
| *A61K 39/00* | (2006.01) | |
| *A61K 39/395* | (2006.01) | |
| *A61P 35/00* | (2006.01) | |
| *C07K 16/28* | (2006.01) | |
| *C07K 16/46* | (2006.01) | |
| *C12N 15/63* | (2006.01) | |

(52) U.S. Cl.
CPC .......... *C07K 16/2896* (2013.01); *A61P 35/00* (2018.01); *C12N 15/63* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 5,530,101 A | * | 6/1996 | Queen ................ | C07K 16/465 424/143.1 |
| 5,618,920 A | * | 4/1997 | Robinson ............ | C07K 14/43 435/69.6 |
| 2019/0167721 A1 | * | 6/2019 | Fan ..................... | C07K 16/40 |

FOREIGN PATENT DOCUMENTS

| | | |
|---|---|---|
| CN | 107663240 A | 2/2018 |
| CN | 108341876 A | 7/2018 |
| CN | 110684107 A | 1/2020 |
| CN | 110684108 A | 1/2020 |
| JP | 2019526275 A | 9/2019 |

OTHER PUBLICATIONS

Lwin et al. Fluorescent humanized anti-CEA antibody specifically labels metastatic pancreatic cancer in a patient-derived orthotopic xenograft (PDOX) mouse model. Oncotarget. 2018; 9:37333-37342. (Year: 2018).*

* cited by examiner

*Primary Examiner* — Maher M Haddad
(74) *Attorney, Agent, or Firm* — Haley Guiliano LLP; James F. Haley, Jr.

(57) ABSTRACT

The present application provides an antibody specifically bound to glycosylated CEACAM5, the preparation of a humanized antibody thereof and an application thereof.

5 Claims, 8 Drawing Sheets

Figure 1:
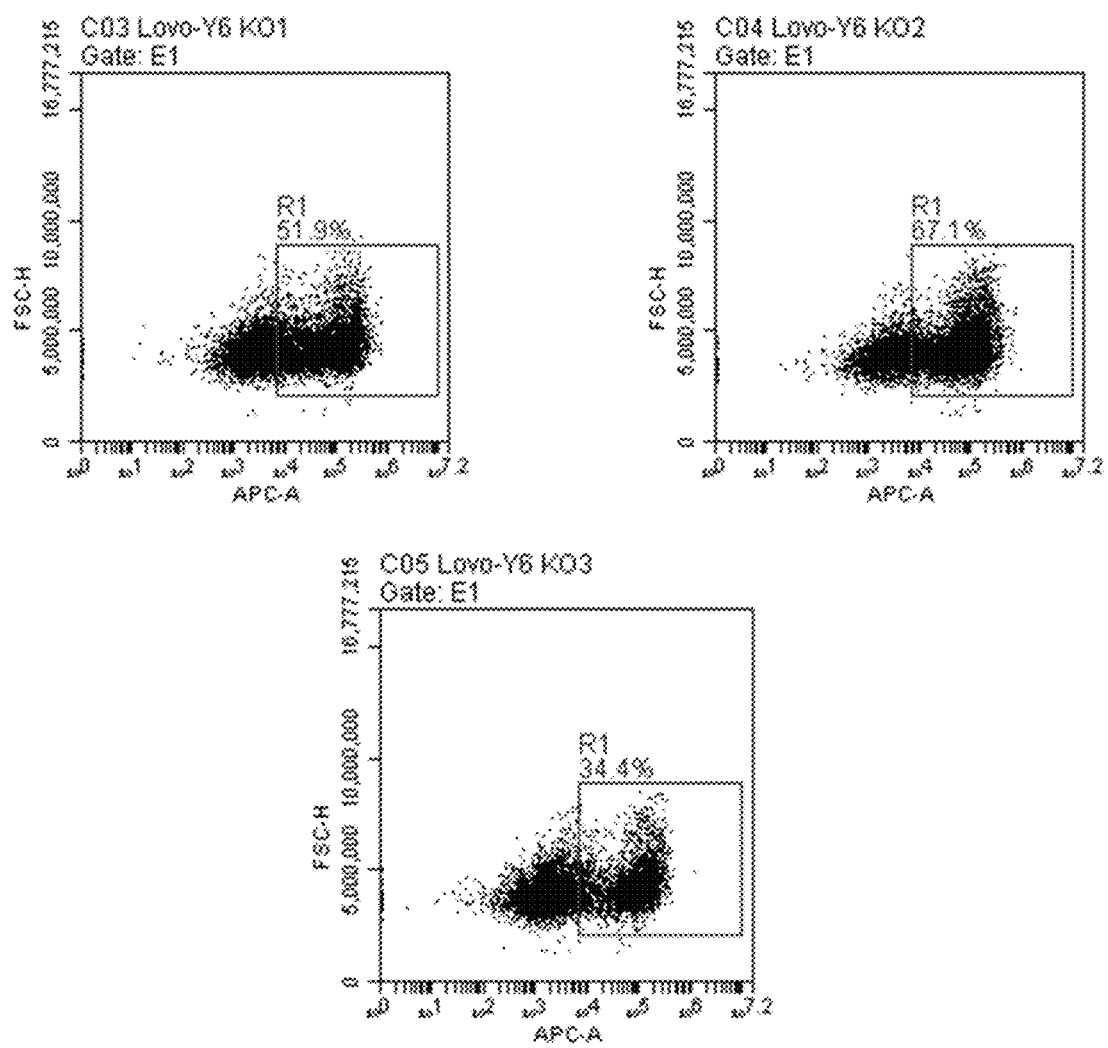

Specification includes a Sequence Listing.

SEQUENCE LISTING

```
<160> NUMBER OF SEQ ID NOS: 131

<210> SEQ ID NO 1
<211> LENGTH: 5
<212> TYPE: PRT
<213> ORGANISM: Artificial Sequence
<220> FEATURE:
<223> OTHER INFORMATION: M19 heavy chain variable region CDR1

<400> SEQUENCE: 1

Asp Tyr Phe Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: M19 heavy chain variable region CDR2
```

```
<400> SEQUENCE: 2

Gln Met Arg Asn Lys Val Asn Gly Asp Thr Thr Glu Tyr Ala Glu Ser
1               5                   10                  15

Val Glu Gly

<210> SEQ ID NO 3
<211> LENGTH: 10
<212> TYPE: PRT
<213> ORGANISM: Artificial Sequence
<220> FEATURE:
<223> OTHER INFORMATION: M19 heavy chain variable region CDR3

<400> SEQUENCE: 3

Asp Lys Gly Ile Ala Tyr Tyr Phe Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: M19 light chain variable region CDR1

<400> SEQUENCE: 4

Arg Ala Ser Ser Ser Val Ser Tyr Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: M19 light chain variable region CDR2

<400> SEQUENCE: 5

Gly Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: M19 light chain variable region CDR3

<400> SEQUENCE: 6

Gln Gln Trp Ser Ser Asn Leu Ser Thr
1               5

<210> SEQ ID NO 7
<211> LENGTH: 5
<212> TYPE: PRT
<213> ORGANISM: Artificial Sequence
<220> FEATURE:
<223> OTHER INFORMATION: M7 heavy chain variable region CDR1

<400> SEQUENCE: 7

Asp Asp Tyr Met His
1               5

<210> SEQ ID NO 8
<211> LENGTH: 17
<212> TYPE: PRT
<213> ORGANISM: Artificial Sequence
<220> FEATURE:
<223> OTHER INFORMATION: M7 heavy chain variable region CDR2
```

```
<400> SEQUENCE: 8

Trp Ile Asp Pro Glu Asn Gly Asp Thr Glu Tyr Ala Ser Lys Phe Gln
1               5                   10                  15

Gly

<210> SEQ ID NO 9
<211> LENGTH: 13
<212> TYPE: PRT
<213> ORGANISM: Artificial Sequence
<220> FEATURE:
<223> OTHER INFORMATION: M7 heavy chain variable region CDR3

<400> SEQUENCE: 9

Ile Tyr Tyr Val Asn Pro His Tyr Tyr Ala Met Asp Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: M7 light chain variable region CDR1

<400> SEQUENCE: 10

Ser Ala Thr Ser Ser Val Ser Tyr Met His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: M7 light chain variable region CDR2

<400> SEQUENCE: 11

Ser Thr Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: M7 light chain variable region CDR3

<400> SEQUENCE: 12

Gln Gln Arg Ser Ser Tyr Pro Leu Thr
1               5

<210> SEQ ID NO 13
<211> LENGTH: 5
<212> TYPE: PRT
<213> ORGANISM: Artificial Sequence
<220> FEATURE:
<223> OTHER INFORMATION: M17 heavy chain variable region CDR1

<400> SEQUENCE: 13

Asp Asp Tyr Met His
1               5

<210> SEQ ID NO 14
<211> LENGTH: 17
<212> TYPE: PRT
<213> ORGANISM: Artificial Sequence
<220> FEATURE:
```

<223> OTHER INFORMATION: M17 heavy chain variable region CDR2

<400> SEQUENCE: 14

Trp Ile Asp Pro Glu Asn Gly Asp Thr Glu Tyr Ala Ser Lys Phe Gln
1               5                   10                  15
Gly

<210> SEQ ID NO 15
<211> LENGTH: 12
<212> TYPE: PRT
<213> ORGANISM: Artificial Sequence
<220> FEATURE:
<223> OTHER INFORMATION: M17 heavy chain variable region CDR3

<400> SEQUENCE: 15

Ile Tyr Tyr Tyr Gly Ser Arg Gly Ala Met Asp Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: M17 light chain variable region CDR1

<400> SEQUENCE: 16

Ser Ala Ser Ser Ser Val Ser Tyr Met His
1               5                   10

<210> SEQ ID NO 17
<211> LENGTH: 7
<212> TYPE: PRT
<213> ORGANISM: Artificial Sequence
<220> FEATURE:
<223> OTHER INFORMATION: M17 light chain variable region CDR2

<400> SEQUENCE: 17

Thr Thr Ser Thr Leu Ala Ser
1               5

<210> SEQ ID NO 18
<211> LENGTH: 9
<212> TYPE: PRT
<213> ORGANISM: Artificial Sequence
<220> FEATURE:
<223> OTHER INFORMATION: M17 light chain variable region CDR3

<400> SEQUENCE: 18

His Gln Arg Ser Ser Tyr Pro Leu Thr
1               5

<210> SEQ ID NO 19
<211> LENGTH: 5
<212> TYPE: PRT
<213> ORGANISM: Artificial Sequence
<220> FEATURE:
<223> OTHER INFORMATION: M18 heavy chain variable region CDR1

<400> SEQUENCE: 19

Thr Tyr Gly Met Thr
1               5

<210> SEQ ID NO 20
<211> LENGTH: 17
<212> TYPE: PRT
<213> ORGANISM: Artificial Sequence

```
<220> FEATURE:
<223> OTHER INFORMATION: M18 heavy chain variable region CDR2

<400> SEQUENCE: 20

Trp Ile Asn Thr Tyr Ser Gly Val Pro Thr Tyr Ile Asp Asp Phe Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: M18 heavy chain variable region CDR3

<400> SEQUENCE: 21

Lys Asp Leu Leu Gly Phe Met Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: M18 light chain variable region CDR1

<400> SEQUENCE: 22

Lys Thr Ser Gln Asp Ile Asn Lys Phe Met Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: M18 light chain variable region CDR2

<400> SEQUENCE: 23

Tyr Thr Ser Thr Leu Gln Pro
1               5

<210> SEQ ID NO 24
<211> LENGTH: 9
<212> TYPE: PRT
<213> ORGANISM: Artificial Sequence
<220> FEATURE:
<223> OTHER INFORMATION: M18 light chain variable region CDR3

<400> SEQUENCE: 24

Leu Gln Tyr Asp Asp Leu Thr Trp Thr
1               5

<210> SEQ ID NO 25
<211> LENGTH: 140
<212> TYPE: PRT
<213> ORGANISM: Artificial Sequence
<220> FEATURE:
<223> OTHER INFORMATION: M19 heavy chain variable region

<400> SEQUENCE: 25

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
```

```
                        35                  40                  45
Thr Asp Tyr Phe Met Asn Trp Val Arg Gln Ala Pro Gly Lys Ala Leu
        50                  55                  60
Glu Trp Leu Gly Gln Met Arg Asn Lys Val Asn Gly Asp Thr Thr Glu
65                  70                  75                  80
Tyr Ala Glu Ser Val Glu Gly Arg Phe Thr Ile Ser Arg Asp Ile Ser
                85                  90                  95
Lys Asn Ser Leu Tyr Leu Gln Met Asn Ser Leu Lys Thr Glu Asp Thr
            100                 105                 110
Ala Val Tyr Tyr Cys Ala Arg Asp Lys Gly Ile Ala Tyr Tyr Phe Asp
            115                 120                 125
Tyr Trp Gly Gln Gly Thr Leu Val Thr Val Ser Ser
            130                 135                 140
```

<210> SEQ ID NO 26
<211> LENGTH: 125
<212> TYPE: PRT
<213> ORGANISM: Artificial Sequence
<220> FEATURE:
<223> OTHER INFORMATION: M19 light chain variable region

<400> SEQUENCE: 26

```
Met Gly Trp Ser Cys Ile Ile Leu Phe Leu Val Ala Thr Ala Thr Gly
1               5                   10                  15
Val His Ser Asp Ile Gln Leu Thr Gln Ser Pro Ser Ser Leu Ser Ala
                20                  25                  30
Ser Val Gly Asp Arg Val Thr Ile Thr Cys Arg Ala Ser Ser Ser Val
            35                  40                  45
Ser Tyr Ile His Trp Tyr Gln Gln Lys Pro Gly Lys Ser Pro Lys Pro
        50                  55                  60
Trp Ile His Gly Thr Ser Asn Leu Ala Ser Gly Val Pro Ser Arg Phe
65                  70                  75                  80
Ser Gly Ser Gly Ser Gly Thr Asp Tyr Thr Leu Thr Ile Ser Ser Leu
                85                  90                  95
Gln Pro Glu Asp Ala Ala Thr Tyr Tyr Cys Gln Gln Trp Ser Ser Asn
            100                 105                 110
Leu Ser Thr Phe Gly Gln Gly Thr Lys Leu Glu Ile Lys
            115                 120                 125
```

<210> SEQ ID NO 27
<211> LENGTH: 122
<212> TYPE: PRT
<213> ORGANISM: Artificial Sequence
<220> FEATURE:
<223> OTHER INFORMATION: M7 heavy chain variable region

<400> SEQUENCE: 27

```
Glu Val Gln Leu Gln Gln Ser Gly Ala Glu Leu Val Arg Pro Gly Ala
1               5                   10                  15
Ser Val Lys Leu Ser Cys Thr Val Ser Gly Phe Asn Ile Lys Asp Asp
                20                  25                  30
Tyr Met His Trp Val Lys Gln Arg Pro Glu Gln Gly Leu Glu Trp Ile
            35                  40                  45
Gly Trp Ile Asp Pro Glu Asn Gly Asp Thr Glu Tyr Ala Ser Lys Phe
        50                  55                  60
Gln Gly Lys Ala Thr Ile Thr Ala Asp Thr Ser Ser Asn Ser Ala Tyr
65                  70                  75                  80
```

```
Leu Gln Leu Ser Ser Leu Thr Ser Glu Asp Thr Ala Val Tyr Tyr Cys
                85                  90                  95

Thr Phe Ile Tyr Tyr Val Asn Pro His Tyr Tyr Ala Met Asp Tyr Trp
            100                 105                 110

Gly Gln Gly Thr Ser Val Thr Val Ser Ser
        115                 120

<210> SEQ ID NO 28
<211> LENGTH: 106
<212> TYPE: PRT
<213> ORGANISM: Artificial Sequence
<220> FEATURE:
<223> OTHER INFORMATION: M7 light chain variable region

<400> SEQUENCE: 28

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 29
<211> LENGTH: 121
<212> TYPE: PRT
<213> ORGANISM: Artificial Sequence
<220> FEATURE:
<223> OTHER INFORMATION: M17 heavy chain variable region

<400> SEQUENCE: 29

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Leu Leu Ser Ser Leu Thr Ser Glu Asp Thr Ala Val Tyr Tyr Cys
                85                  90                  95

Thr Thr Ile Tyr Tyr Tyr Gly Ser Arg Gly Ala Met Asp Tyr Trp Gly
            100                 105                 110

Gln Gly Thr Ser Val Thr Val Ser Ser
        115                 120

<210> SEQ ID NO 30
<211> LENGTH: 106
<212> TYPE: PRT
<213> ORGANISM: Artificial Sequence
```

```
<220> FEATURE:
<223> OTHER INFORMATION: M17 light chain variable region

<400> SEQUENCE: 30

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Thr Thr Ser Thr Leu Ala Ser Gly Val Pro Ala Arg Phe Ser Gly Ser
    50                  55                  60

Gly Ser Gly Thr Ser Tyr Phe Leu Thr Ile Ser Arg Met Glu Ala Glu
65                  70                  75                  80

Asp Ala Ala Thr Tyr Tyr Cys His Gln Arg Ser Ser Tyr Pro Leu Thr
                85                  90                  95

Phe Gly Ala Gly Thr Lys Leu Glu Leu Lys
            100                 105

<210> SEQ ID NO 31
<211> LENGTH: 118
<212> TYPE: PRT
<213> ORGANISM: Artificial Sequence
<220> FEATURE:
<223> OTHER INFORMATION: M18 heavy chain variable region

<400> SEQUENCE: 31

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Thr Trp Val Lys Gln Ala Pro Gly Lys Gly Leu Lys Trp Met
        35                  40                  45

Gly Trp Ile Asn Thr Tyr Ser Gly Val Pro Thr Tyr Ile Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Gly Arg Lys Asp Leu Leu Gly Phe Met Asp Tyr Trp Gly Gln Gly Thr
            100                 105                 110

Ser Val Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: M18 light chain variable region

<400> SEQUENCE: 32

Asp Ile Gln Met Thr Gln Ser Pro Ser Ser Leu Ser Ala Ser Leu Gly
1               5                   10                  15

Gly Lys Val Thr Ile Thr Cys Lys Thr Ser Gln Asp Ile Asn Lys Phe
            20                  25                  30

Met Ala Trp Tyr Gln His Lys Pro Gly Lys Gly Pro Arg Leu Leu Ile
        35                  40                  45
```

```
-continued

Arg Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Arg Asn Leu Glu Pro
 65                  70                  75                  80

Glu Asp Ile Ala Thr Tyr Tyr Cys Leu Gln Tyr Asp Asp Leu Thr Trp
                 85                  90                  95

Thr Phe Gly Gly Gly Thr Lys Leu Glu Ile
                100                 105

<210> SEQ ID NO 33
<211> LENGTH: 213
<212> TYPE: PRT
<213> ORGANISM: Artificial Sequence
<220> FEATURE:
<223> OTHER INFORMATION: antibody hMN14 light chain variable region

<400> SEQUENCE: 33

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Val Gly Thr Ser
                20                  25                  30

Val Ala Trp Tyr Gln Gln Lys Pro Gly Lys Ala Pro Lys Leu Leu Ile
             35                  40                  45

Tyr Trp Thr Ser Thr Arg His Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Leu Tyr Arg Ser
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 34
<211> LENGTH: 449
<212> TYPE: PRT
<213> ORGANISM: Artificial Sequence
<220> FEATURE:
<223> OTHER INFORMATION: antibody hMN14 heavy chain variable region

<400> SEQUENCE: 34

Glu Val Gln Leu Val Glu Ser Gly Gly Gly Val Val Gln Pro Gly Arg
 1               5                  10                  15

Ser Leu Arg Leu Ser Cys Ser Ala Ser Gly Phe Asp Phe Thr Thr Tyr
                20                  25                  30
```

```
Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
 50                  55                  60

Lys Asp Arg Phe Thr Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Ser Leu Tyr Phe Gly Phe Pro Trp Phe Ala Tyr Trp Gly Gln Gly
                100                 105                 110

Thr Pro Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445
```

Lys

```
<210> SEQ ID NO 35
<211> LENGTH: 12
<212> TYPE: RNA
<213> ORGANISM: Artificial Sequence
<220> FEATURE:
<223> OTHER INFORMATION: CEACAM5 KO1 sgRNA sequence

<400> SEQUENCE: 35
gacgacagac gg                                                            12

<210> SEQ ID NO 36
<211> LENGTH: 16
<212> TYPE: RNA
<213> ORGANISM: Artificial Sequence
<220> FEATURE:
<223> OTHER INFORMATION: CEACAM5 KO2 sgRNA sequence

<400> SEQUENCE: 36
gagacgaaca cgcgcc                                                        16

<210> SEQ ID NO 37
<211> LENGTH: 16
<212> TYPE: RNA
<213> ORGANISM: Artificial Sequence
<220> FEATURE:
<223> OTHER INFORMATION: CEACAM5 KO3 sgRNA sequence

<400> SEQUENCE: 37
caggggagca ccacgg                                                        16

<210> SEQ ID NO 38
<211> LENGTH: 417
<212> TYPE: DNA
<213> ORGANISM: Artificial Sequence
<220> FEATURE:
<223> OTHER INFORMATION: M19 heavy chain variable region nucleotide
      sequence

<400> SEQUENCE: 38
atgggctgga gctgcatcat cctgttcctc gtggccacag ctacaggagt gcatagcgag        60
gtgcagctgg tggaatcagg aggaggactg gtgcagccag gaggatctct gagactgtct       120
tgcgccgcca gcggctttac attcaccgac tacttcatga attgggtccg gcaggcccca       180
ggaaaagcac tcgagtggct gggacagatg cggaacaagg tcaacggcga caccacagag       240
tacgccgaaa gcgtggaggg cagattcacc atcagccggg acatcagcaa gaacagcctg       300
tacctgcaga tgaacagcct gaagaccgag gataccgccg tgtactattg cgccagggac       360
aagggcatcg cctactactt cgactactgg ggccagggaa cactggtgac agtgtct         417

<210> SEQ ID NO 39
<211> LENGTH: 375
<212> TYPE: DNA
<213> ORGANISM: Artificial Sequence
<220> FEATURE:
<223> OTHER INFORMATION: M19 light chain variable region nucleotide
      sequence

<400> SEQUENCE: 39
atgggctgga gctgcatcat cctgttcctc gtggccacag ctacaggagt gcatagcgac        60
atccagctga cccagtctcc tagcagcctg agcgccagcg tggagatag agtgaccatc       120 acttgcagag ccagcagcag cgtgtcctac atccattggt accagcagaa gcccggcaag       180
```

```
agccctaagc cttggattca cggcaccagc aatctggcca gcggagtgcc tagcagattc    240
agcggcagcg aagcggcac  cgattacacc ctgaccatca gctctctgca gccagaggac    300
gcagccacct actattgcca gcagtggagc agcaacctga gcacctttgg ccagggaacc    360
aagctggaga tcaag                                                     375
```

<210> SEQ ID NO 40
<211> LENGTH: 366
<212> TYPE: DNA
<213> ORGANISM: Artificial Sequence
<220> FEATURE:
<223> OTHER INFORMATION: M7 heavy chain variable region nucleotide
      sequence

<400> SEQUENCE: 40

```
gaggttcagc tgcagcagtc tggggctgag cttgtgaggc caggggcctc agtcaagttg     60
tcctgcacag tttctggctt aacattaaa  gacgactata tgcactgggt gaagcagagg    120
cctgaacagg gcctggagtg gattggatgg attgatcctg agaatggtga tactgaatat    180
gcctcgaagt tccagggcaa ggccactata acagcagaca catcctccaa ctcagcctac    240
ctgcagctca gcagcctgac atctgaggac actgccgtct attactgtac ttttatctac    300
tatgttaatc ctcattacta tgctatggac tactggggtc aaggaacctc agtcaccgtc    360
tcctca                                                                366
```

<210> SEQ ID NO 41
<211> LENGTH: 318
<212> TYPE: DNA
<213> ORGANISM: Artificial Sequence
<220> FEATURE:
<223> OTHER INFORMATION: M7 light chain variable region nucleotide
      sequence

<400> SEQUENCE: 41

```
caaattgttc tcacccagtc tccagcaatc atgtctgctt ctccagggga aaggtcacc     60 atcacctgca gtgccacctc aagtgtaagt tacatgcact ggttccagca gaagccaggc    120
acttctccca aactctggat ttatagcaca tccaacctgg cttctggagt ccctgctcgc    180
ttcagtggca gtggatctgg gacctcttac tctctcacaa tcagccgagt ggaggctgaa    240
gatgctgcca cttattactg ccagcaaagg agtagttacc cgctcacgtt cggtgctggg    300
accaagctgg agctgaaa                                                 318
```

<210> SEQ ID NO 42
<211> LENGTH: 363
<212> TYPE: DNA
<213> ORGANISM: Artificial Sequence
<220> FEATURE:
<223> OTHER INFORMATION: M17 heavy chain variable region nucleotide
      sequence

<400> SEQUENCE: 42

```
gaggttcagc tgcagcagtc tggggctgag cttgtgaggc caggggcctc agtcaagttg     60
tcctgcacag cttctggctt aacattaaa  gacgactata tgcactgggt gaagcagagg    120
cctgaacagg gcctggagtg gattggatgg attgatcctg agaatggtga tactgaatat    180
gcctcgaagt tccagggcaa ggccactata acagcagaca catcctccaa cacagcctac    240
ctgctgctca gcagcctgac atctgaggac actgccgtct attactgtac taccatttat    300
tactacggta gtagaggtgc tatggactac tggggtcaag gaacctcagt caccgtctcc    360
``` tca                                                                                 363

<210> SEQ ID NO 43
<211> LENGTH: 318
<212> TYPE: DNA
<213> ORGANISM: Artificial Sequence
<220> FEATURE:
<223> OTHER INFORMATION: M17 light chain variable region nucleotide
      sequence

<400> SEQUENCE: 43
caaattgttc tcacccagtc tccagcaatc atgtctgcat ctccagggga gaaggtcacc        60
ataacctgca gtgccagctc aagtgtaagt tacatgcact ggttccagca gaagccaggc       120
acttctccca aactctggat ttataccaca tccaccctgg cttctggagt ccctgctcgc       180
ttcagtggca gtggatctgg gacctcttac tttctcacaa tcagccgaat ggaggctgaa       240
gatgctgcca cttattactg ccaccaaagg agtagttacc cactcacgtt cggtgctggg       300
accaagctgg agctgaaa                                                     318

<210> SEQ ID NO 44
<211> LENGTH: 354
<212> TYPE: DNA
<213> ORGANISM: Artificial Sequence
<220> FEATURE:
<223> OTHER INFORMATION: M18 heavy chain variable region nucleotide
      sequence

<400> SEQUENCE: 44
cagatccagt tggtacagtc tggacctgag ctgaagaagc ctggagagac agtcaagatc        60
tcctgcaagg cttctgggta tacctttaca acctatggaa tgacctgggt gaaacaggct       120
ccaggaaagg gtttaaagtg gatgggctgg ataaacacct actctggagt gccaacatat       180
attgatgact caagggacg gtttgccttc tctttggaaa cctctgccag cactgcctat        240
ttgcagatca acaacctcaa aaatgaggac acggctacat atttctgtgg aagaaaggat       300
ctacttggtt ttatggacta ctggggtcaa ggaacctcag tcaccgtctc ctca             354

<210> SEQ ID NO 45
<211> LENGTH: 318
<212> TYPE: DNA
<213> ORGANISM: Artificial Sequence
<220> FEATURE:
<223> OTHER INFORMATION: M18 light chain variable region nucleotide
      sequence

<400> SEQUENCE: 45
gacatccaga tgacacagtc tccatcctca ctgtctgcat ctctgggagg caaagtcacc        60
atcacttgca agacaagcca agacattaac aagtttatgg cttggtacca acacaagcct       120
ggaaaaggtc ctaggctgct catacgttac acatctacat tacagccagg catcccatca       180
aggttcagtg gaagtgggtc tgggagagat tattccttca gcatcaggaa cctgagcct       240 gaagatattg caacttatta ttgtctacag tatgatgatc ttacgtggac gttcggtgga       300
ggcaccaagc tggaaatc                                                     318

<210> SEQ ID NO 46
<211> LENGTH: 940
<212> TYPE: DNA
<213> ORGANISM: Artificial Sequence
<220> FEATURE:
<223> OTHER INFORMATION: extracellular domain A1-B1-His nucleotide -continued sequence

<400> SEQUENCE: 46

```
atgcacagct cagcactgct ctgttgcctg gtcctcctga ctggggtgag ggccaagctc      60
actattgaat ccacgccgtt caatgtcgca gaggggaagg aggtgcttct acttgtccac     120
aatctgcccc agcatctttt tggctacagc tggtacaaag gtgaaagagt ggatggcaac     180
cgtcaaatta taggatatgt aataggaact caacaagcta ccccagggcc cgcatacagt     240
ggtcgagaga taatataccc caatgcatcc ctgctgatcc agaacatcat ccagaatgac     300
acaggattct acaccctaca cgtcataaag tcagatcttg tgaatgaaga agcaactggc     360
cagttccggg tatacccgga gctgcccaag ccctccatct ccagcaacaa ctccaaaccc     420
gtggaggaca aggatgctgt ggccttcacc tgtgaacctg agactcagga cgcaacctac     480
ctgtggtggg taaacaatca gagcctcccg gtcagtccca ggctgcagct gtccaatggc     540
aacaggaccc tcactctatt caatgtcaca agaaatgaca cagcaagcta caatgtgaa      600
acccagaacc cagtgagtgc caggcgcagt gattcagtca tcctgaatgt cctctatggc     660
ccggatgccc ccaccatttc ccctctaaac acatcttaca gatcagggga aaatctgaac     720
ctctcctgcc acgcagcctc taacccacct gcacagtact cttggtttgt caatgggact     780
ttccagcaat ccacccaaga gctctttatc cccaacatca ctgtgaataa tagtggatcc     840
tatacgtgcc aagcccataa ctcagacact ggcctcaata ggaccacagt cacgacgatc     900
acagtctatg cacaccatca ccatcaccat tgagtctaga                          940
```

<210> SEQ ID NO 47
<211> LENGTH: 292
<212> TYPE: PRT
<213> ORGANISM: Artificial Sequence
<220> FEATURE:
<223> OTHER INFORMATION: extracellular domain A1-B1-His amino acid sequence

<400> SEQUENCE: 47

```
Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
                20                  25                  30

Trp Tyr Lys Gly Glu Arg Val Asp Gly Asn Arg Gln Ile Ile Gly Tyr
            35                  40                  45

Val Ile Gly Thr Gln Gln Ala Thr Pro Gly Pro Ala Tyr Ser Gly Arg
        50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175
```

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
            195                 200                 205

Ser Pro Leu Asn Thr Ser Tyr Arg Ser Gly Glu Asn Leu Asn Leu Ser
            210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala His His
            275                 280                 285

His His His His
    290

<210> SEQ ID NO 48
<211> LENGTH: 616
<212> TYPE: DNA
<213> ORGANISM: Artificial Sequence
<220> FEATURE:
<223> OTHER INFORMATION: extracellular domain A2-B2-His nucleotide
      sequence

<400> SEQUENCE: 48
atgcacagct cagcactgct ctgttgcctg gtcctcctga ctggggtgag ggccgagcca      60
cccaaaccct tcatcaccag caacaactcc aaccccgtgg aggatgagga tgctgtagcc     120
ttaacctgtg aacctgagat tcagaacaca acctacctgt ggtgggtaaa taatcagagc     180
ctcccggtca gtcccaggct gcagctgtcc aatgacaaca ggaccctcac tctactcagt     240
gtcacaagga tgatgtagg accctatgag tgtggaatcc agaacgaatt aagtgttgac     300
cacagcgacc cagtcatcct gaatgtcctc tatggcccag cgaccccac catttccccc     360 tcatacacct attaccgtcc aggggtgaac ctcagcctct cctgccatgc agcctctaac     420
ccacctgcac agtattcttg gctgattgat gggaacatcc agcaacacac acaagagctc     480
tttatctcca acatcactga aagaacagc ggactctata cctgccaggc caataactca     540
gccagtggcc acagcaggac tacagtcaag acaatcacag tctctgcgca ccatcaccat     600
caccattgag tctaga                                                      616

<210> SEQ ID NO 49
<211> LENGTH: 184
<212> TYPE: PRT
<213> ORGANISM: Artificial Sequence
<220> FEATURE:
<223> OTHER INFORMATION: extracellular domain A2-B2-His amino acid
      sequence

<400> SEQUENCE: 49

Glu Pro Pro Lys Pro Phe Ile Thr Ser Asn Asn Ser Asn Pro Val Glu
1               5                   10                  15

Asp Glu Asp Ala Val Ala Leu Thr Cys Glu Pro Glu Ile Gln Asn Thr
            20                  25                  30

Thr Tyr Leu Trp Trp Val Asn Asn Gln Ser Leu Pro Val Ser Pro Arg
        35                  40                  45

Leu Gln Leu Ser Asn Asp Asn Arg Thr Leu Thr Leu Leu Ser Val Thr

Arg Asn Asp Val Gly Pro Tyr Glu Cys Gly Ile Gln Asn Glu Leu Ser
65                  70                  75                  80

Val Asp His Ser Asp Pro Val Ile Leu Asn Val Leu Tyr Gly Pro Asp
                85                  90                  95

Asp Pro Thr Ile Ser Pro Ser Tyr Thr Tyr Tyr Arg Pro Gly Val Asn
            100                 105                 110

Leu Ser Leu Ser Cys His Ala Ala Ser Asn Pro Pro Ala Gln Tyr Ser
        115                 120                 125

Trp Leu Ile Asp Gly Asn Ile Gln Gln His Thr Gln Glu Leu Phe Ile
    130                 135                 140

Ser Asn Ile Thr Glu Lys Asn Ser Gly Leu Tyr Thr Cys Gln Ala Asn
145                 150                 155                 160

Asn Ser Ala Ser Gly His Ser Arg Thr Thr Val Lys Thr Ile Thr Val
                165                 170                 175

Ser Ala His His His His His His
            180

<210> SEQ ID NO 50
<211> LENGTH: 643
<212> TYPE: DNA
<213> ORGANISM: Artificial Sequence
<220> FEATURE:
<223> OTHER INFORMATION: extracellular domain A3-B3-His nucleotide
      sequence

<400> SEQUENCE: 50
atgcacagct cagcactgct ctgttgcctg gtcctcctga ctggggtgag ggccgagctg      60
cccaagccct ccatctccag caacaactcc aaaccgtgg aggacaagga tgctgtggcc     120
ttcacctgtg aacctgaggc tcagaacaca acctacctgt ggtgggtaaa tggtcagagc     180
ctcccagtca gtcccaggct gcagctgtcc aatggcaaca ggaccctcac tctattcaat     240
gtcacaagaa atgacgcaag agcctatgta tgtggaatcc agaactcagt gagtgcaaac     300
cgcagtgacc cagtcaccct ggatgtcctc tatgggccgg acaccccat catttccccc     360 ccagactcgt cttacctttc gggagcgaac ctcaacctct cctgccactc ggcctctaac     420
ccatccccgc agtattcttg gcgtatcaat gggataccgc agcaacacac acaagttctc     480
tttatcgcca aaatcacgcc aaataataac gggaacctatg cctgttttgt ctctaacttg     540
gctactggcc gcaataattc catagtcaag agcatcacag tctctgcatc tggaacttct     600
cctggtctct cagctcacca tcaccatcac cattgagtct aga                        643

<210> SEQ ID NO 51
<211> LENGTH: 193
<212> TYPE: PRT
<213> ORGANISM: Artificial Sequence
<220> FEATURE:
<223> OTHER INFORMATION: extracellular domain A3-B3-His amino acid
      sequence

<400> SEQUENCE: 51

Glu Leu Pro Lys Pro Ser Ile Ser Ser Asn Asn Ser Lys Pro Val Glu
1               5                   10                  15

Asp Lys Asp Ala Val Ala Phe Thr Cys Glu Pro Glu Ala Gln Asn Thr
            20                  25                  30

Thr Tyr Leu Trp Trp Val Asn Gly Gln Ser Leu Pro Val Ser Pro Arg
        35                  40                  45

Leu Gln Leu Ser Asn Gly Asn Arg Thr Leu Thr Leu Phe Asn Val Thr
    50                  55                  60

Arg Asn Asp Ala Arg Ala Tyr Val Cys Gly Ile Gln Asn Ser Val Ser
65                  70                  75                  80

Ala Asn Arg Ser Asp Pro Val Thr Leu Asp Val Leu Tyr Gly Pro Asp
                85                  90                  95

Thr Pro Ile Ile Ser Pro Pro Asp Ser Ser Tyr Leu Ser Gly Ala Asn
                100                 105                 110

Leu Asn Leu Ser Cys His Ser Ala Ser Asn Pro Ser Pro Gln Tyr Ser
            115                 120                 125

Trp Arg Ile Asn Gly Ile Pro Gln Gln His Thr Gln Val Leu Phe Ile
    130                 135                 140

Ala Lys Ile Thr Pro Asn Asn Asn Gly Thr Tyr Ala Cys Phe Val Ser
145                 150                 155                 160

Asn Leu Ala Thr Gly Arg Asn Asn Ser Ile Val Lys Ser Ile Thr Val
                165                 170                 175

Ser Ala Ser Gly Thr Ser Pro Gly Leu Ser Ala His His His His
                180                 185                 190

His

<210> SEQ ID NO 52
<211> LENGTH: 375
<212> TYPE: DNA
<213> ORGANISM: Artificial Sequence
<220> FEATURE:
<223> OTHER INFORMATION: humanized antibody hAb-009 light chain variable
      region nucleotide sequence

<400> SEQUENCE: 52
atgggctgga gctgcatcat cctgttcctc gtggccacag ctacaggagt gcatagcgag    60
atcgtgctga cccagtctcc agccacactg agcgcttctc aggagagag agccacactg    120 tcttgtagag ccagccagag cgtgtcctac atccattggt accagcagaa gcccggacag    180
tctcctaggc cttggattca cggcacaagc aatctggcca ccggagtgcc agctagattc    240
agcggcagcg gaagcggcac cgactttacc ctgaccatca gctctctgga gccagaggac    300
gcagccgtgt actattgcca gcagtggagc agcaatctga gcacctttgg cggcggaacc    360
aaggtggaga tcaag                                                    375

<210> SEQ ID NO 53
<211> LENGTH: 417
<212> TYPE: DNA
<213> ORGANISM: Artificial Sequence
<220> FEATURE:
<223> OTHER INFORMATION: humanized antibody hAb-009 heavy chain variable
      region nucleotide sequence

<400> SEQUENCE: 53
atgggctgga gctgcatcat cctgttcctc gtggccacag ctacaggagt gcatagcgag    60
gtgcagctgg tggaatcagg aggaggactg gtgcagccag aggatctct gagactgtct    120 tgcgccgcca gcggctttac attcaccgac tactacatga attgggtccg gcaggcccca    180
ggaaaagcac tcgagtggct gggcttcatc cggaacaagg tcaacggcga caccacagag    240
tacgccgcca gcgtgaaggg cagattcacc atcagccggg acgacagcaa gaacagcctg    300
tacctgcaga tgaacagcct gaagaccgag gataccgccg tgtactattg cgccagggac    360
aagggcatcg cctactactt cgactactgg ggccaggaa cactggtgac agtgtct     417

<210> SEQ ID NO 54
<211> LENGTH: 375
<212> TYPE: DNA
<213> ORGANISM: Artificial Sequence
<220> FEATURE:
<223> OTHER INFORMATION: humanized antibody hAb-003 light chain variable
      region nucleotide sequence

<400> SEQUENCE: 54

```
atgggctgga gctgcatcat cctgttcctc gtggccacag ctacaggagt gcatagcgac    60
atccagatga cccagagccc tagcagcctg agcgccagcg tgggagatag agtgaccatc   120
acttgcagag ccagcagcag cgtgtcctac atccattggt accagcagaa gcccggcaag   180
agccctaagc ccctgatcta cggcaccagc aatctggcca gcggagtgcc tagcagattc   240
agcggcagcg gaagcggcac cgactttacc ctgaccatca gctctctgca gccagaggac   300
gcagccacct actattgcca gcagtggagc agcaacctga gcacctttgg ccagggaacc   360
aagctggaga tcaag                                                    375
```

<210> SEQ ID NO 55
<211> LENGTH: 417
<212> TYPE: DNA
<213> ORGANISM: Artificial Sequence
<220> FEATURE:
<223> OTHER INFORMATION: humanized antibody hAb-003 heavy chain variable
      region nucleotide sequence

<400> SEQUENCE: 55

```
atgggctgga gctgcatcat cctgttcctc gtggccacag ctacaggagt gcatagcgag    60
gtgcagctgg tggaatcagg aggaggactg gtgcagccag aggatctct gagactgtct    120
tgcgccgcca gcggctttac attcaccgac tacttcatga attgggtccg gcaggcccca   180
ggaaaagcac tcgagtgggt cggacagatg cggaacaagg tcaacggcga caccacagag   240
tacgccgaga gcgtggaggg aagattcacc atcagccggg acgacagcaa gaacagcctg   300
tacctgcaga tgaacagcct gaagaccgag gataccgccg tgtactattg cgccagggac   360
aagggcatcg cctactactt cgactactgg ggccagggaa cactggtgac agtgtct     417
```

<210> SEQ ID NO 56
<211> LENGTH: 375
<212> TYPE: DNA
<213> ORGANISM: Artificial Sequence
<220> FEATURE:
<223> OTHER INFORMATION: humanized antibody hAb-005 light chain variable
      region nucleotide sequence

<400> SEQUENCE: 56

```
atgggctgga gctgcatcat cctgttcctc gtggccacag ctacaggagt gcatagcgac    60
atccagctga cccagtctcc tagcagcctg agcgccagcg tgggagatag agtgaccatc   120
acttgcagag ccagcagcag cgtgtcctac atccattggt accagcagaa gcccggcaag   180
agccctaagc cttggatcta cggcaccagc aatctggcca gcggagtgcc tagcagattc   240
agcggcagcg gaagcggcac cgattacacc ctgaccatca gctctctgca gccagaggac   300
gcagccacct actattgcca gcagtggagc agcaacctga gcacctttgg ccagggaacc   360
aaggtggaga tcaag                                                    375
```

<210> SEQ ID NO 57
<211> LENGTH: 417
<212> TYPE: DNA

<213> ORGANISM: Artificial Sequence
<220> FEATURE:
<223> OTHER INFORMATION: humanized antibody hAb-005 heavy chain variable
      region nucleotide sequence

<400> SEQUENCE: 57

```
atgggctgga gctgcatcat cctgttcctc gtggccacag ctacaggagt gcatagcgag      60
gtgcagctgg tggaatcagg aggaggactg gtgcagccag aggatctct  gagactgtct     120
tgcgccgcca gcggctttac attcaccgac tacaccatgt cttgggtccg gcaggcacca     180
ggaaaagcac tcgagtgggt cggcttcatc cggaacaagg tcaacggcga caccacagag     240
tacagcgaca cgcgtggaggg aaggttcacc atcagccggg acaacagcaa gaacaccctg    300
tacctgcaga tgaacagcct gcgcgcagag gataccgccg tgtactattg cgccagggac     360
aagggcatcg cctactactt cgactactgg ggccagggaa cactggtgac agtgtct        417
```

<210> SEQ ID NO 58
<211> LENGTH: 375
<212> TYPE: DNA
<213> ORGANISM: Artificial Sequence
<220> FEATURE:
<223> OTHER INFORMATION: humanized antibody hAb-006 light chain variable
      region nucleotide sequence

<400> SEQUENCE: 58

```
atgggctgga gctgcatcat cctgttcctc gtggccacag ctacaggagt gcatagcgac      60
atcgtgctgt ctcagtctcc aggcaccctg tctctgtctc caggagagag agccaccctg     120
tcttgtagag ccagcagcag cgtgtcctac atccattggt accagcagaa gcccggacag     180
gctcctagac cttggattca cggcacaagc aatctggcca gcggaatccc cgacagattc     240
agcggcagcg gaagcggcac cgattacacc ctgaccatca gcagactgga gccagaggac     300
ttcgccgtgt actattgcca gcagtggagc agcaatctga gcacctttgg cggcggaacc     360
aaggtggaga tcaag                                                      375
```

<210> SEQ ID NO 59
<211> LENGTH: 417
<212> TYPE: DNA
<213> ORGANISM: Artificial Sequence
<220> FEATURE:
<223> OTHER INFORMATION: humanized antibody hAb-006 heavy chain variable
      region nucleotide sequence

<400> SEQUENCE: 59

```
atgggctgga gctgcatcat cctgttcctc gtggccacag ctacaggagt gcatagcgag      60
gtgcagctgg tggaatcagg aggaggactg gtgcagccag aggatctct  gagactgtct     120
tgcgccgcca gcggctttac attcaccgac tactacatga attgggtccg gcaggccca     180
ggaaaaggac tcgagtggct gggcttcatc cggaacaagg tcaacggcga caccaccgag    240
tacagcgcca cgcgtgaaggg caggttcacc atcagccggg acatcagcaa gaacagcctg    300
tacctgcaga tgaacagcct gaagaccgag gataccgccg tgtactattg cgccagggac     360
aagggcatcg cctactactt cgactactgg ggccagggaa cactggtgac agtgtct        417
```

<210> SEQ ID NO 60
<211> LENGTH: 375
<212> TYPE: DNA
<213> ORGANISM: Artificial Sequence
<220> FEATURE:
<223> OTHER INFORMATION: humanized antibody hAb-010 light chain variable
      region nucleotide sequence

```
<400> SEQUENCE: 60
atgggctgga gctgcatcat cctgttcctc gtggccacag ctacaggagt gcatagcgag      60
atcgtgctga cccagtctcc agccacactg agcgcttctc caggagagag agccacactg     120
tcttgcagag ccagctctag cgtgtcctac atccattggt accagcagaa gcccggccag     180
tctcctagac ccctgatcta cggcaccagc aacagagcca caggcgtgcc agctagattc     240
agcggcagcg gaagcggcac cgactttacc ctgaccatca gctctctgga gccagaggac     300
gcagccgtgt actattgcca gcagtggagc agcaatctga gcacctttgg cggcggaacc     360
aaggtggaga tcaag                                                      375

<210> SEQ ID NO 61
<211> LENGTH: 417
<212> TYPE: DNA
<213> ORGANISM: Artificial Sequence
<220> FEATURE:
<223> OTHER INFORMATION: humanized antibody hAb-010 heavy chain variable
      region nucleotide sequence

<400> SEQUENCE: 61
atgggctgga gctgcatcat cctgttcctc gtggccacag ctacaggagt gcatagcgag      60
gtgcagctgg tggaatcagg aggaggactg gtgcagccag aggatctct gagactgtct     120 tgcgccgcca gcggctttac attcaccgac tactacatgg attgggtccg cggctcca     180 ggaaaagcac tcgagtgggt cggcttcatc cggaacaagg tcaacggcga caccacagag     240
tacgccgcca gcgtgaaggg cagattcacc atcagccggg acgacagcaa gaacagcctg     300
tacctgcaga tgaacagcct gaagaccgag gataccgccg tgtactattg cgccagggac     360
aagggcatcg cctactactt cgactactgg ggccagggaa cactggtgac agtgtct      417

<210> SEQ ID NO 62
<211> LENGTH: 375
<212> TYPE: DNA
<213> ORGANISM: Artificial Sequence
<220> FEATURE:
<223> OTHER INFORMATION: humanized antibody hAb-013 light chain variable
      region nucleotide sequence

<400> SEQUENCE: 62
atgggctgga gctgcatcat cctgttcctc gtggccacag ctacaggagt gcatagccag      60
atcgtgctga cccagtctcc agccacactg agcgcttctc caggagagag agccacactg     120
tcttgcagag ccagctctag cgtgtcctac atccattggt accagcagaa gcccggacag     180
agccctagac tctgatcta cggcaccagc aatctggcca gcggagtgcc agctagattc     240
agcggcagcg gaagcggcac cgactttacc ctgaccatca gctctctgga gccagaggac     300
gcagccgtgt actattgcca gcagtggagc agcaatctga gcacctttgg cggcggaacc     360
aaggtggaga tcaag                                                      375

<210> SEQ ID NO 63
<211> LENGTH: 417
<212> TYPE: DNA
<213> ORGANISM: Artificial Sequence
<220> FEATURE:
<223> OTHER INFORMATION: humanized antibody hAb-013 heavy chain variable
      region nucleotide sequence

<400> SEQUENCE: 63
atgggctgga gctgcatcat cctgttcctc gtggccacag ctacaggagt gcatagcgag      60
```
gtgcagctgg tggaatcagg aggaggactg gtgcagccag gaggatctct gagactgtct    120
tgcgccgcca gcggctttac attcaccgac tactacatgg attgggtccg gcaggctcca    180
ggaaaagcac tcgagtgggt cggcttcacc cggaacaagg tcaacggcga caccacagag    240
tacgccgcca gcgtgaaggg cagattcacc atcagccggg acgacagcaa gaacagcctg    300
tacctgcaga tgaacagcct gaagaccgag gataccgccg tgtactattg cgccagggac    360
aagggcatcg cctactactt cgactactgg ggccagggaa cactggtgac agtgtct      417

<210> SEQ ID NO 64
<211> LENGTH: 375
<212> TYPE: DNA
<213> ORGANISM: Artificial Sequence
<220> FEATURE:
<223> OTHER INFORMATION: humanized antibody hAb-016 light chain variable
      region nucleotide sequence

<400> SEQUENCE: 64
atgggctgga gctgcatcat cctgttcctc gtggccacag ctacaggagt gcatagcgag     60
atcgtgctga cccagtctcc aggcacactg agcgcttctc caggagagag agccacactg    120
tcttgcagag ccagctctag cgtgtcctac atccattggt accagcagaa gcccggacag    180
agccctagac tctgatcta cggcaccagc aatctggcca gcggagtgcc agacagattc    240
agcggcagcg gaagcggcac cgactttacc ctgaccatca gcagactgga gccagaggac    300
gcagccgtgt actattgcca gcagtggagc agcaatctga gcacctttgg cggcggaacc    360
aaggtggaga tcaag                                                    375

<210> SEQ ID NO 65
<211> LENGTH: 417
<212> TYPE: DNA
<213> ORGANISM: Artificial Sequence
<220> FEATURE:
<223> OTHER INFORMATION: humanized antibody hAb-016 heavy chain variable
      region nucleotide sequence

<400> SEQUENCE: 65
atgggctgga gctgcatcat cctgttcctc gtggccacag ctacaggagt gcatagcgag     60
gtgcagctgg tggaatcagg aggaggactg gtgcagccag gaggatctct gagactgtct    120
tgcgccgcca gcggctttac attcaccgac tactacatgg attgggtccg gcaggctcca    180
ggaaaagcac tcgagtgggt cggcttcacc cggaacaagg tcaacggcga caccacagag    240
tacgccgcca gcgtgaaggg cagattcacc atcagccggg acgacagcaa gaacagcctg    300
tacctgcaga tgaacagcct gaagaccgag gataccgccg tgtactattg cgccagggac    360
aagggcatcg cctactactt cgactactgg ggccagggaa cactggtgac agtgtct      417

<210> SEQ ID NO 66
<211> LENGTH: 375
<212> TYPE: DNA
<213> ORGANISM: Artificial Sequence
<220> FEATURE:
<223> OTHER INFORMATION: humanized antibody hAb-017 light chain variable
      region nucleotide sequence

<400> SEQUENCE: 66
atgggctgga gctgcatcat cctgttcctc gtggccacag ctacaggagt gcatagcgag     60
atcgtgctga cccagtctcc agccacactg agcgcttctc caggagagag agccacactg    120
tcttgcagag ccagctctag cgtgtcctac atccattggt accagcagaa gcccggccag    180

```
tctcctagac ctctgatcta cggcgccagc aatctggcca gcggcgtgcc agccagattc    240
agcggaagcg gcagcggcac cgactttacc ctgaccatca gctctctgga gccagaggac    300
gcagccgtgt actattgcca gcagtggagc agcaatctga gcacctttgg cggcggaacc    360
aaggtggaga tcaag                                                     375
```

<210> SEQ ID NO 67
<211> LENGTH: 417
<212> TYPE: DNA
<213> ORGANISM: Artificial Sequence
<220> FEATURE:
<223> OTHER INFORMATION: humanized antibody hAb-017 heavy chain variable
      region nucleotide sequence

<400> SEQUENCE: 67

```
atgggctgga gctgcatcat cctgttcctc gtggccacag ctacaggagt gcatagcgag     60
gtgcagctgg tggaatcagg aggaggactg gtgcagccag aggatctctc tgagactgtct   120 tgcgccgcca gcggctttac attcaccgac tactacatgg attgggtccg gcaggctcca   180
ggaaaagcac tcgagtgggt cggcttcacc cggaacaagg tcaacggcga caccacagag   240
tacgccgcca gcgtgaaggg cagattcacc atcagccggg acgacagcaa gaacagcctg   300
tacctgcaga tgaacagcct gaagaccgag gataccgccg tgtactattg cgccagggac   360
aagggcatcg cctactactt cgactactgg ggccaggga cactggtgac agtgtct      417
```

<210> SEQ ID NO 68
<211> LENGTH: 125
<212> TYPE: PRT
<213> ORGANISM: Artificial Sequence
<220> FEATURE:
<223> OTHER INFORMATION: humanized antibody hAb-009 light chain variable
      region amino acid sequence

<400> SEQUENCE: 68

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Ala
                20                  25                  30

Ser Pro Gly Glu Arg Ala Thr Leu Ser Cys Arg Ala Ser Gln Ser Val
            35                  40                  45

Ser Tyr Ile His Trp Tyr Gln Gln Lys Pro Gly Gln Ser Pro Arg Pro
        50                  55                  60

Trp Ile His Gly Thr Ser Asn Leu Ala Thr Gly Val Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Ala Ala Val Tyr Tyr Cys Gln Gln Trp Ser Ser Asn
            100                 105                 110

Leu Ser Thr Phe Gly Gly Gly Thr Lys Val Glu Ile Lys
        115                 120                 125
```

<210> SEQ ID NO 69
<211> LENGTH: 140
<212> TYPE: PRT
<213> ORGANISM: Artificial Sequence
<220> FEATURE:
<223> OTHER INFORMATION: humanized antibody hAb-009 heavy chain variable
      region amino acid sequence

<400> SEQUENCE: 69

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Thr Asp Tyr Tyr Met Asn Trp Val Arg Gln Ala Pro Gly Lys Ala Leu
50                  55                  60

Glu Trp Leu Gly Phe Ile Arg Asn Lys Val Asn Gly Asp Thr Thr Glu
65                  70                  75                  80

Tyr Ala Ala Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Lys Gly Ile Ala Tyr Tyr Phe Asp
        115                 120                 125

Tyr Trp Gly Gln Gly Thr Leu Val Thr Val Ser Ser
    130                 135                 140

<210> SEQ ID NO 70
<211> LENGTH: 125
<212> TYPE: PRT
<213> ORGANISM: Artificial Sequence
<220> FEATURE:
<223> OTHER INFORMATION: humanized antibody hAb-003 light chain variable
      region amino acid sequence

<400> SEQUENCE: 70

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Ser Ser Val
            35                  40                  45

Ser Tyr Ile His Trp Tyr Gln Gln Lys Pro Gly Lys Ser Pro Lys Pro
50                  55                  60

Leu Ile Tyr Gly Thr Ser Asn Leu Ala Ser Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Ala Ala Thr Tyr Tyr Cys Gln Gln Trp Ser Ser Asn
            100                 105                 110

Leu Ser Thr Phe Gly Gln Gly Thr Lys Leu Glu Ile Lys
        115                 120                 125

<210> SEQ ID NO 71
<211> LENGTH: 140
<212> TYPE: PRT
<213> ORGANISM: Artificial Sequence
<220> FEATURE:
<223> OTHER INFORMATION: humanized antibody hAb-003 heavy chain variable
      region amino acid sequence

<400> SEQUENCE: 71

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

-continued

```
Pro Gly Gly Ser Leu Arg Leu Ser Cys Ala Ala Ser Gly Phe Thr Phe
        35                  40                  45

Thr Asp Tyr Phe Met Asn Trp Val Arg Gln Ala Pro Gly Lys Ala Leu
    50                  55                  60

Glu Trp Val Gly Gln Met Arg Asn Lys Val Asn Gly Asp Thr Thr Glu
65                  70                  75                  80

Tyr Ala Glu Ser Val Glu Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Lys Gly Ile Ala Tyr Tyr Phe Asp
        115                 120                 125

Tyr Trp Gly Gln Gly Thr Leu Val Thr Val Ser Ser
    130                 135                 140

<210> SEQ ID NO 72
<211> LENGTH: 125
<212> TYPE: PRT
<213> ORGANISM: Artificial Sequence
<220> FEATURE:
<223> OTHER INFORMATION: humanized antibody hAb-005 light chain variable
      region amino acid sequence

<400> SEQUENCE: 72

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Arg Ala Ser Ser Ser Val
        35                  40                  45

Ser Tyr Ile His Trp Tyr Gln Gln Lys Pro Gly Lys Ser Pro Lys Pro
    50                  55                  60

Trp Ile Tyr Gly Thr Ser Asn Leu Ala Ser Gly Val Pro Ser Arg Phe
65                  70                  75                  80

Ser Gly Ser Gly Ser Gly Thr Asp Tyr Thr Leu Thr Ile Ser Ser Leu
                85                  90                  95

Gln Pro Glu Asp Ala Ala Thr Tyr Tyr Cys Gln Gln Trp Ser Ser Asn
            100                 105                 110

Leu Ser Thr Phe Gly Gln Gly Thr Lys Val Glu Ile Lys
        115                 120                 125

<210> SEQ ID NO 73
<211> LENGTH: 140
<212> TYPE: PRT
<213> ORGANISM: Artificial Sequence
<220> FEATURE:
<223> OTHER INFORMATION: humanized antibody hAb-005 heavy chain variable
      region amino acid sequence

<400> SEQUENCE: 73

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Thr Met Ser Trp Val Arg Gln Ala Pro Gly Lys Ala Leu
    50                  55                  60
```

Glu Trp Val Gly Phe Ile Arg Asn Lys Val Asn Gly Asp Thr Thr Glu
65                  70                  75                  80

Tyr Ser Asp Ser Val Glu Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Lys Gly Ile Ala Tyr Tyr Phe Asp
        115                 120                 125

Tyr Trp Gly Gln Gly Thr Leu Val Thr Val Ser Ser
    130                 135                 140

<210> SEQ ID NO 74
<211> LENGTH: 125
<212> TYPE: PRT
<213> ORGANISM: Artificial Sequence
<220> FEATURE:
<223> OTHER INFORMATION: humanized antibody hAb-006 light chain variable
      region amino acid sequence

<400> SEQUENCE: 74

Met Gly Trp Ser Cys Ile Ile Leu Phe Leu Val Ala Thr Ala Thr Gly
1               5                   10                  15

Val His Ser Asp Ile Val Leu Ser Gln Ser Pro Gly Thr Leu Ser Leu
            20                  25                  30

Ser Pro Gly Glu Arg Ala Thr Leu Ser Cys Arg Ala Ser Ser Ser Val
        35                  40                  45

Ser Tyr Ile His Trp Tyr Gln Gln Lys Pro Gly Gln Ala Pro Arg Pro
    50                  55                  60

Trp Ile His Gly Thr Ser Asn Leu Ala Ser Gly Ile Pro Asp Arg Phe
65                  70                  75                  80

Ser Gly Ser Gly Ser Gly Thr Asp Tyr Thr Leu Thr Ile Ser Arg Leu
                85                  90                  95

Glu Pro Glu Asp Phe Ala Val Tyr Tyr Cys Gln Gln Trp Ser Ser Asn
            100                 105                 110

Leu Ser Thr Phe Gly Gly Gly Thr Lys Val Glu Ile Lys
        115                 120                 125

<210> SEQ ID NO 75
<211> LENGTH: 140
<212> TYPE: PRT
<213> ORGANISM: Artificial Sequence
<220> FEATURE:
<223> OTHER INFORMATION: humanized antibody hAb-006 heavy chain variable
      region amino acid sequence

<400> SEQUENCE: 75

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Asn Trp Val Arg Gln Ala Pro Gly Lys Gly Leu
    50                  55                  60

Glu Trp Leu Gly Phe Ile Arg Asn Lys Val Asn Gly Asp Thr Thr Glu
65                  70                  75                  80

Tyr Ser Ala Ser Val Lys Gly Arg Phe Thr Ile Ser Arg Asp Ile Ser
                85                  90                  95

```
Lys Asn Ser Leu Tyr Leu Gln Met Asn Ser Leu Lys Thr Glu Asp Thr
                100                 105                 110

Ala Val Tyr Tyr Cys Ala Arg Asp Lys Gly Ile Ala Tyr Tyr Phe Asp
            115                 120                 125

Tyr Trp Gly Gln Gly Thr Leu Val Thr Val Ser Ser
        130                 135                 140

<210> SEQ ID NO 76
<211> LENGTH: 125
<212> TYPE: PRT
<213> ORGANISM: Artificial Sequence
<220> FEATURE:
<223> OTHER INFORMATION: humanized antibody hAb-010 light chain variable
      region amino acid sequence

<400> SEQUENCE: 76

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Ala
            20                  25                  30

Ser Pro Gly Glu Arg Ala Thr Leu Ser Cys Arg Ala Ser Ser Ser Val
        35                  40                  45

Ser Tyr Ile His Trp Tyr Gln Gln Lys Pro Gly Gln Ser Pro Arg Pro
    50                  55                  60

Leu Ile Tyr Gly Thr Ser Asn Arg Ala Thr Gly Val Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Ala Ala Val Tyr Tyr Cys Gln Gln Trp Ser Ser Asn
            100                 105                 110

Leu Ser Thr Phe Gly Gly Gly Thr Lys Val Glu Ile Lys
        115                 120                 125

<210> SEQ ID NO 77
<211> LENGTH: 140
<212> TYPE: PRT
<213> ORGANISM: Artificial Sequence
<220> FEATURE:
<223> OTHER INFORMATION: humanized antibody hAb-010 heavy chain variable
      region amino acid sequence

<400> SEQUENCE: 77

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Asp Trp Val Arg Gln Ala Pro Gly Lys Ala Leu
    50                  55                  60

Glu Trp Val Gly Phe Ile Arg Asn Lys Val Asn Gly Asp Thr Thr Glu
65                  70                  75                  80

Tyr Ala Ala Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Lys Gly Ile Ala Tyr Tyr Phe Asp
        115                 120                 125
```

Tyr Trp Gly Gln Gly Thr Leu Val Thr Val Ser Ser
        130                 135                 140

<210> SEQ ID NO 78
<211> LENGTH: 125
<212> TYPE: PRT
<213> ORGANISM: Artificial Sequence
<220> FEATURE:
<223> OTHER INFORMATION: humanized antibody hAb-013 light chain variable
      region amino acid sequence

<400> SEQUENCE: 78

Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Thr Leu Ser Ala
            20                  25                  30

Ser Pro Gly Glu Arg Ala Thr Leu Ser Cys Arg Ala Ser Ser Ser Val
        35                  40                  45

Ser Tyr Ile His Trp Tyr Gln Gln Lys Pro Gly Gln Ser Pro Arg Pro
    50                  55                  60

Leu Ile Tyr Gly Thr Ser Asn Leu Ala Ser Gly Val Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Ala Ala Val Tyr Tyr Cys Gln Gln Trp Ser Ser Asn
            100                 105                 110

Leu Ser Thr Phe Gly Gly Gly Thr Lys Val Glu Ile Lys
        115                 120                 125

<210> SEQ ID NO 79
<211> LENGTH: 140
<212> TYPE: PRT
<213> ORGANISM: Artificial Sequence
<220> FEATURE:
<223> OTHER INFORMATION: humanized antibody hAb-013 heavy chain variable
      region amino acid sequence

<400> SEQUENCE: 79

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Asp Trp Val Arg Gln Ala Pro Gly Lys Ala Leu
    50                  55                  60

Glu Trp Val Gly Phe Thr Arg Asn Lys Val Asn Gly Asp Thr Thr Glu
65                  70                  75                  80

Tyr Ala Ala Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Lys Gly Ile Ala Tyr Phe Asp
        115                 120                 125

Tyr Trp Gly Gln Gly Thr Leu Val Thr Val Ser Ser
        130                 135                 140

<210> SEQ ID NO 80

```
<211> LENGTH: 125
<212> TYPE: PRT
<213> ORGANISM: Artificial Sequence
<220> FEATURE:
<223> OTHER INFORMATION: humanized antibody hAb-016 light chain variable
      region amino acid sequence

<400> SEQUENCE: 80

Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Ala
            20                  25                  30

Ser Pro Gly Glu Arg Ala Thr Leu Ser Cys Arg Ala Ser Ser Ser Val
        35                  40                  45

Ser Tyr Ile His Trp Tyr Gln Gln Lys Pro Gly Gln Ser Pro Arg Pro
    50                  55                  60

Leu Ile Tyr Gly Thr Ser Asn Leu Ala Ser Gly Val Pro Asp Arg Phe
65                  70                  75                  80

Ser Gly Ser Gly Ser Gly Thr Asp Phe Thr Leu Thr Ile Ser Arg Leu
                85                  90                  95

Glu Pro Glu Asp Ala Ala Val Tyr Tyr Cys Gln Gln Trp Ser Ser Asn
            100                 105                 110

Leu Ser Thr Phe Gly Gly Gly Thr Lys Val Glu Ile Lys
        115                 120                 125

<210> SEQ ID NO 81
<211> LENGTH: 140
<212> TYPE: PRT
<213> ORGANISM: Artificial Sequence
<220> FEATURE:
<223> OTHER INFORMATION: humanized antibody hAb-016 heavy chain variable
      region amino acid sequence

<400> SEQUENCE: 81

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Asp Trp Val Arg Gln Ala Pro Gly Lys Ala Leu
    50                  55                  60

Glu Trp Val Gly Phe Thr Arg Asn Lys Val Asn Gly Asp Thr Thr Glu
65                  70                  75                  80

Tyr Ala Ala Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Lys Gly Ile Ala Tyr Tyr Phe Asp
        115                 120                 125

Tyr Trp Gly Gln Gly Thr Leu Val Thr Val Ser Ser
    130                 135                 140

<210> SEQ ID NO 82
<211> LENGTH: 125
<212> TYPE: PRT
<213> ORGANISM: Artificial Sequence
<220> FEATURE:
<223> OTHER INFORMATION: humanized antibody hAb-017 light chain variable
      region amino acid sequence
```

<400> SEQUENCE: 82

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Ala
            20                  25                  30

Ser Pro Gly Glu Arg Ala Thr Leu Ser Cys Arg Ala Ser Ser Ser Val
        35                  40                  45

Ser Tyr Ile His Trp Tyr Gln Gln Lys Pro Gly Gln Ser Pro Arg Pro
    50                  55                  60

Leu Ile Tyr Gly Ala Ser Asn Leu Ala Ser Gly Val Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Ala Ala Val Tyr Tyr Cys Gln Gln Trp Ser Ser Asn
            100                 105                 110

Leu Ser Thr Phe Gly Gly Gly Thr Lys Val Glu Ile Lys
        115                 120                 125

<210> SEQ ID NO 83
<211> LENGTH: 140
<212> TYPE: PRT
<213> ORGANISM: Artificial Sequence
<220> FEATURE:
<223> OTHER INFORMATION: humanized antibody hAb-017 heavy chain variable
      region amino acid sequence

<400> SEQUENCE: 83

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Asp Trp Val Arg Gln Ala Pro Gly Lys Ala Leu
    50                  55                  60

Glu Trp Val Gly Phe Thr Arg Asn Lys Val Asn Gly Asp Thr Thr Glu
65                  70                  75                  80

Tyr Ala Ala Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Lys Gly Ile Ala Tyr Tyr Phe Asp
        115                 120                 125

Tyr Trp Gly Gln Gly Thr Leu Val Thr Val Ser Ser
    130                 135                 140

<210> SEQ ID NO 84
<211> LENGTH: 10
<212> TYPE: PRT
<213> ORGANISM: Artificial Sequence
<220> FEATURE:
<223> OTHER INFORMATION: humanized antibody hAb-009 light chain variable
      region CDR1 sequence

<400> SEQUENCE: 84

Arg Ala Ser Gln Ser Val Ser Tyr Ile His
1               5                   10

```
<210> SEQ ID NO 85
<211> LENGTH: 7
<212> TYPE: PRT
<213> ORGANISM: Artificial Sequence
<220> FEATURE:
<223> OTHER INFORMATION: humanized antibody hAb-009 light chain variable
      region CDR2 sequence

<400> SEQUENCE: 85

Gly Thr Ser Asn Leu Ala Thr
1               5

<210> SEQ ID NO 86
<211> LENGTH: 9
<212> TYPE: PRT
<213> ORGANISM: Artificial Sequence
<220> FEATURE:
<223> OTHER INFORMATION: humanized antibody hAb-009 light chain variable
      region CDR3 sequence

<400> SEQUENCE: 86

Gln Gln Trp Ser Ser Asn Leu Ser Thr
1               5

<210> SEQ ID NO 87
<211> LENGTH: 5
<212> TYPE: PRT
<213> ORGANISM: Artificial Sequence
<220> FEATURE:
<223> OTHER INFORMATION: humanized antibody hAb-009 heavy chain variable
      region CDR1 sequence

<400> SEQUENCE: 87

Asp Tyr Tyr Met Asn
1               5

<210> SEQ ID NO 88
<211> LENGTH: 19
<212> TYPE: PRT
<213> ORGANISM: Artificial Sequence
<220> FEATURE:
<223> OTHER INFORMATION: humanized antibody hAb-009 heavy chain variable
      region CDR2 sequence

<400> SEQUENCE: 88

Phe Ile Arg Asn Lys Val Asn Gly Asp Thr Thr Glu Tyr Ala Ala Ser
1               5                   10                  15

Val Lys Gly

<210> SEQ ID NO 89
<211> LENGTH: 10
<212> TYPE: PRT
<213> ORGANISM: Artificial Sequence
<220> FEATURE:
<223> OTHER INFORMATION: humanized antibody hAb-009 heavy chain variable
      region CDR3 sequence

<400> SEQUENCE: 89

Asp Lys Gly Ile Ala Tyr Tyr Phe Asp Tyr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: humanized antibody hAb-003 light chain variable
``` region CDR1 sequence

<400> SEQUENCE: 90

Arg Ala Ser Ser Ser Val Ser Tyr Ile His
1               5                   10

<210> SEQ ID NO 91
<211> LENGTH: 7
<212> TYPE: PRT
<213> ORGANISM: Artificial Sequence
<220> FEATURE:
<223> OTHER INFORMATION: humanized antibody hAb-003 light chain variable
      region CDR2 sequence

<400> SEQUENCE: 91

Gly Thr Ser Asn Leu Ala Ser
1               5

<210> SEQ ID NO 92
<211> LENGTH: 9
<212> TYPE: PRT
<213> ORGANISM: Artificial Sequence
<220> FEATURE:
<223> OTHER INFORMATION: humanized antibody hAb-003 light chain variable
      region CDR3 sequence

<400> SEQUENCE: 92

Gln Gln Trp Ser Ser Asn Leu Ser Thr
1               5

<210> SEQ ID NO 93
<211> LENGTH: 5
<212> TYPE: PRT
<213> ORGANISM: Artificial Sequence
<220> FEATURE:
<223> OTHER INFORMATION: humanized antibody hAb-003 heavy chain variable
      region CDR1 sequence

<400> SEQUENCE: 93

Asp Tyr Phe Met Asn
1               5

<210> SEQ ID NO 94
<211> LENGTH: 19
<212> TYPE: PRT
<213> ORGANISM: Artificial Sequence
<220> FEATURE:
<223> OTHER INFORMATION: humanized antibody hAb-003 heavy chain variable
      region CDR2 sequence

<400> SEQUENCE: 94

Gln Met Arg Asn Lys Val Asn Gly Asp Thr Thr Glu Tyr Ala Glu Ser
1               5                   10                  15

Val Glu Gly

<210> SEQ ID NO 95
<211> LENGTH: 10
<212> TYPE: PRT
<213> ORGANISM: Artificial Sequence
<220> FEATURE:
<223> OTHER INFORMATION: humanized antibody hAb-003 heavy chain variable
      region CDR3 sequence

<400> SEQUENCE: 95

Asp Lys Gly Ile Ala Tyr Tyr Phe Asp Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: humanized antibody hAb-005 light chain variable
      region CDR1 sequence

<400> SEQUENCE: 96

Arg Ala Ser Ser Ser Val Ser Tyr Ile His
1               5                   10

<210> SEQ ID NO 97
<211> LENGTH: 7
<212> TYPE: PRT
<213> ORGANISM: Artificial Sequence
<220> FEATURE:
<223> OTHER INFORMATION: humanized antibody hAb-005 light chain variable
      region CDR2 sequence

<400> SEQUENCE: 97

Gly Thr Ser Asn Leu Ala Ser
1               5

<210> SEQ ID NO 98
<211> LENGTH: 9
<212> TYPE: PRT
<213> ORGANISM: Artificial Sequence
<220> FEATURE:
<223> OTHER INFORMATION: humanized antibody hAb-005 light chain variable
      region CDR3 sequence

<400> SEQUENCE: 98

Gln Gln Trp Ser Ser Asn Leu Ser Thr
1               5

<210> SEQ ID NO 99
<211> LENGTH: 5
<212> TYPE: PRT
<213> ORGANISM: Artificial Sequence
<220> FEATURE:
<223> OTHER INFORMATION: humanized antibody hAb-005 heavy chain variable
      region CDR1 sequence

<400> SEQUENCE: 99

Asp Tyr Thr Met Ser
1               5

<210> SEQ ID NO 100
<211> LENGTH: 19
<212> TYPE: PRT
<213> ORGANISM: Artificial Sequence
<220> FEATURE:
<223> OTHER INFORMATION: humanized antibody hAb-005 heavy chain variable
      region CDR2 sequence

<400> SEQUENCE: 100

Phe Ile Arg Asn Lys Val Asn Gly Asp Thr Thr Glu Tyr Ser Asp Ser
1               5                   10                  15

Val Glu Gly

<210> SEQ ID NO 101
<211> LENGTH: 10
<212> TYPE: PRT
<213> ORGANISM: Artificial Sequence
<220> FEATURE:
<223> OTHER INFORMATION: humanized antibody hAb-005 heavy chain variable region CDR3 sequence

<400> SEQUENCE: 101

Asp Lys Gly Ile Ala Tyr Tyr Phe Asp Tyr
1               5                   10

<210> SEQ ID NO 102
<211> LENGTH: 10
<212> TYPE: PRT
<213> ORGANISM: Artificial Sequence
<220> FEATURE:
<223> OTHER INFORMATION: humanized antibody hAb-006 light chain variable
      region CDR1 sequence

<400> SEQUENCE: 102

Arg Ala Ser Ser Ser Val Ser Tyr Ile His
1               5                   10

<210> SEQ ID NO 103
<211> LENGTH: 7
<212> TYPE: PRT
<213> ORGANISM: Artificial Sequence
<220> FEATURE:
<223> OTHER INFORMATION: humanized antibody hAb-006 light chain variable
      region CDR2 sequence

<400> SEQUENCE: 103

Gly Thr Ser Asn Leu Ala Ser
1               5

<210> SEQ ID NO 104
<211> LENGTH: 9
<212> TYPE: PRT
<213> ORGANISM: Artificial Sequence
<220> FEATURE:
<223> OTHER INFORMATION: humanized antibody hAb-006 light chain variable
      region CDR3 sequence

<400> SEQUENCE: 104

Gln Gln Trp Ser Ser Asn Leu Ser Thr
1               5

<210> SEQ ID NO 105
<211> LENGTH: 5
<212> TYPE: PRT
<213> ORGANISM: Artificial Sequence
<220> FEATURE:
<223> OTHER INFORMATION: humanized antibody hAb-006 heavy chain variable
      region CDR1 sequence

<400> SEQUENCE: 105

Asp Tyr Tyr Met Asn
1               5

<210> SEQ ID NO 106
<211> LENGTH: 19
<212> TYPE: PRT
<213> ORGANISM: Artificial Sequence
<220> FEATURE:
<223> OTHER INFORMATION: humanized antibody hAb-006 heavy chain variable
      region CDR2 sequence

<400> SEQUENCE: 106

Phe Ile Arg Asn Lys Val Asn Gly Asp Thr Thr Glu Tyr Ser Ala Ser
1               5                   10                  15

Val Lys Gly

<210> SEQ ID NO 107
<211> LENGTH: 10
<212> TYPE: PRT
<213> ORGANISM: Artificial Sequence
<220> FEATURE:
<223> OTHER INFORMATION: humanized antibody hAb-006 heavy chain variable
      region CDR3 sequence

<400> SEQUENCE: 107

Asp Lys Gly Ile Ala Tyr Tyr Phe Asp Tyr
1               5                   10

<210> SEQ ID NO 108
<211> LENGTH: 10
<212> TYPE: PRT
<213> ORGANISM: Artificial Sequence
<220> FEATURE:
<223> OTHER INFORMATION: humanized antibody hAb-010 light chain variable
      region CDR1 sequence

<400> SEQUENCE: 108

Arg Ala Ser Ser Ser Val Ser Tyr Ile His
1               5                   10

<210> SEQ ID NO 109
<211> LENGTH: 7
<212> TYPE: PRT
<213> ORGANISM: Artificial Sequence
<220> FEATURE:
<223> OTHER INFORMATION: humanized antibody hAb-010 light chain variable
      region CDR2 sequence

<400> SEQUENCE: 109

Gly Thr Ser Asn Arg Ala Thr
1               5

<210> SEQ ID NO 110
<211> LENGTH: 9
<212> TYPE: PRT
<213> ORGANISM: Artificial Sequence
<220> FEATURE:
<223> OTHER INFORMATION: humanized antibody hAb-010 light chain variable
      region CDR3 sequence

<400> SEQUENCE: 110

Gln Gln Trp Ser Ser Asn Leu Ser Thr
1               5

<210> SEQ ID NO 111
<211> LENGTH: 5
<212> TYPE: PRT
<213> ORGANISM: Artificial Sequence
<220> FEATURE:
<223> OTHER INFORMATION: humanized antibody hAb-010 heavy chain variable
      region CDR1 sequence

<400> SEQUENCE: 111

Asp Tyr Tyr Met Asp
1               5

<210> SEQ ID NO 112
<211> LENGTH: 19
<212> TYPE: PRT
<213> ORGANISM: Artificial Sequence
<220> FEATURE:
<223> OTHER INFORMATION: humanized antibody hAb-010 heavy chain variable
      region CDR2 sequence

<400> SEQUENCE: 112

Phe Ile Arg Asn Lys Val Asn Gly Asp Thr Thr Glu Tyr Ala Ala Ser
1               5                   10                  15
Val Lys Gly

<210> SEQ ID NO 113
<211> LENGTH: 10
<212> TYPE: PRT
<213> ORGANISM: Artificial Sequence
<220> FEATURE:
<223> OTHER INFORMATION: humanized antibody hAb-010 heavy chain variable
      region CDR3 sequence

<400> SEQUENCE: 113

Asp Lys Gly Ile Ala Tyr Tyr Phe Asp Tyr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: humanized antibody hAb-013 light chain variable
      region CDR1 sequence

<400> SEQUENCE: 114

Arg Ala Ser Ser Ser Val Ser Tyr Ile His
1               5                   10

<210> SEQ ID NO 115
<211> LENGTH: 7
<212> TYPE: PRT
<213> ORGANISM: Artificial Sequence
<220> FEATURE:
<223> OTHER INFORMATION: humanized antibody hAb-013 light chain variable
      region CDR2 sequence

<400> SEQUENCE: 115

Gly Thr Ser Asn Leu Ala Ser
1               5

<210> SEQ ID NO 116
<211> LENGTH: 9
<212> TYPE: PRT
<213> ORGANISM: Artificial Sequence
<220> FEATURE:
<223> OTHER INFORMATION: humanized antibody hAb-013 light chain variable
      region CDR3 sequence

<400> SEQUENCE: 116

Gln Gln Trp Ser Ser Asn Leu Ser Thr
1               5

<210> SEQ ID NO 117
<211> LENGTH: 5
<212> TYPE: PRT
<213> ORGANISM: Artificial Sequence
<220> FEATURE:
<223> OTHER INFORMATION: humanized antibody hAb-013 heavy chain variable
      region CDR1 sequence

<400> SEQUENCE: 117

Asp Tyr Tyr Met Asp
1               5

<210> SEQ ID NO 118

```
<211> LENGTH: 19
<212> TYPE: PRT
<213> ORGANISM: Artificial Sequence
<220> FEATURE:
<223> OTHER INFORMATION: humanized antibody hAb-013 heavy chain variable
      region CDR2 sequence

<400> SEQUENCE: 118

Phe Thr Arg Asn Lys Val Asn Gly Asp Thr Thr Glu Tyr Ala Ala Ser
1               5                   10                  15

Val Lys Gly

<210> SEQ ID NO 119
<211> LENGTH: 10
<212> TYPE: PRT
<213> ORGANISM: Artificial Sequence
<220> FEATURE:
<223> OTHER INFORMATION: humanized antibody hAb-013 heavy chain variable
      region CDR3 sequence

<400> SEQUENCE: 119

Asp Lys Gly Ile Ala Tyr Tyr Phe Asp Tyr
1               5                   10

<210> SEQ ID NO 120
<211> LENGTH: 10
<212> TYPE: PRT
<213> ORGANISM: Artificial Sequence
<220> FEATURE:
<223> OTHER INFORMATION: humanized antibody hAb-016 light chain variable
      region CDR1 sequence

<400> SEQUENCE: 120

Arg Ala Ser Ser Ser Val Ser Tyr Ile His
1               5                   10

<210> SEQ ID NO 121
<211> LENGTH: 7
<212> TYPE: PRT
<213> ORGANISM: Artificial Sequence
<220> FEATURE:
<223> OTHER INFORMATION: humanized antibody hAb-016 light chain variable
      region CDR2 sequence

<400> SEQUENCE: 121

Gly Thr Ser Asn Leu Ala Ser
1               5

<210> SEQ ID NO 122
<211> LENGTH: 9
<212> TYPE: PRT
<213> ORGANISM: Artificial Sequence
<220> FEATURE:
<223> OTHER INFORMATION: humanized antibody hAb-016 light chain variable
      region CDR3 sequence

<400> SEQUENCE: 122

Gln Gln Trp Ser Ser Asn Leu Ser Thr
1               5

<210> SEQ ID NO 123
<211> LENGTH: 5
<212> TYPE: PRT
<213> ORGANISM: Artificial Sequence
<220> FEATURE:
<223> OTHER INFORMATION: humanized antibody hAb-016 heavy chain variable
      region CDR1 sequence
```

```
<400> SEQUENCE: 123

Asp Tyr Tyr Met Asp
1               5

<210> SEQ ID NO 124
<211> LENGTH: 19
<212> TYPE: PRT
<213> ORGANISM: Artificial Sequence
<220> FEATURE:
<223> OTHER INFORMATION: humanized antibody hAb-016 heavy chain variable
      region CDR2 sequence

<400> SEQUENCE: 124

Phe Thr Arg Asn Lys Val Asn Gly Asp Thr Thr Glu Tyr Ala Ala Ser
1               5                   10                  15

Val Lys Gly

<210> SEQ ID NO 125
<211> LENGTH: 10
<212> TYPE: PRT
<213> ORGANISM: Artificial Sequence
<220> FEATURE:
<223> OTHER INFORMATION: humanized antibody hAb-016 heavy chain variable
      region CDR3 sequence

<400> SEQUENCE: 125

Asp Lys Gly Ile Ala Tyr Tyr Phe Asp Tyr
1               5                   10

<210> SEQ ID NO 126
<211> LENGTH: 10
<212> TYPE: PRT
<213> ORGANISM: Artificial Sequence
<220> FEATURE:
<223> OTHER INFORMATION: humanized antibody hAb-017 light chain variable
      region CDR1 sequence

<400> SEQUENCE: 126

Arg Ala Ser Ser Ser Val Ser Tyr Ile His
1               5                   10

<210> SEQ ID NO 127
<211> LENGTH: 7
<212> TYPE: PRT
<213> ORGANISM: Artificial Sequence
<220> FEATURE:
<223> OTHER INFORMATION: humanized antibody hAb-017 light chain variable
      region CDR2 sequence

<400> SEQUENCE: 127

Gly Ala Ser Asn Leu Ala Ser
1               5

<210> SEQ ID NO 128
<211> LENGTH: 9
<212> TYPE: PRT
<213> ORGANISM: Artificial Sequence
<220> FEATURE:
<223> OTHER INFORMATION: humanized antibody hAb-017 light chain variable
      region CDR3 sequence

<400> SEQUENCE: 128

Gln Gln Trp Ser Ser Asn Leu Ser Thr
1               5

<210> SEQ ID NO 129
```

```
<211> LENGTH: 5
<212> TYPE: PRT
<213> ORGANISM: Artificial Sequence
<220> FEATURE:
<223> OTHER INFORMATION: humanized antibody hAb-017 heavy chain variable
      region CDR1 sequence

<400> SEQUENCE: 129

Asp Tyr Tyr Met Asp
1               5

<210> SEQ ID NO 130
<211> LENGTH: 19
<212> TYPE: PRT
<213> ORGANISM: Artificial Sequence
<220> FEATURE:
<223> OTHER INFORMATION: humanized antibody hAb-017 heavy chain variable
      region CDR2 sequence

<400> SEQUENCE: 130

Phe Thr Arg Asn Lys Val Asn Gly Asp Thr Thr Glu Tyr Ala Ala Ser
1               5                   10                  15

Val Lys Gly

<210> SEQ ID NO 131
<211> LENGTH: 10
<212> TYPE: PRT
<213> ORGANISM: Artificial Sequence
<220> FEATURE:
<223> OTHER INFORMATION: humanized antibody hAb-017 heavy chain variable
      region CDR3 sequence

<400> SEQUENCE: 131

Asp Lys Gly Ile Ala Tyr Tyr Phe Asp Tyr
1               5                   10
```

ANTIBODY SPECIFICALLY BOUND TO GLYCOSYLATED CEACAM5

CROSS-REFERENCE TO RELATED APPLICATIONS

This application is a United States National Phase Application filed under 35 U.S.C. § 371 from International Patent Application No. PCT/CN2021/070825, filed on Jan. 8, 2021, which claims priority to International Patent Application No. PCT/CN2020/110514, filed on Aug. 21, 2020. The content and disclosure of the foregoing applications are incorporated by reference herein in their entireties.

SEQUENCE LISTING

The instant application contains a Sequence Listing which is submitted electronically in text format in lieu of a paper copy and is hereby incorporated by reference in its entirety. Said text copy, created on Feb. 16, 2023, is named 000362-0004-301-Sequence.txt and is 80,307 bytes in size. The text file is being submitted electronically via EFS-Web.

TECHNICAL FIELD

The present invention relates to a monoclonal antibody. More specifically, the present application relates to a monoclonal antibody specifically binding to a glycosylated CEACAM5, preparation of a humanized antibody thereof, and use thereof.

BACKGROUND ART

In China, the gastrointestinal-related tumors including colorectal cancer, gastric cancer, and esophageal cancer are common, and their new case numbers are 520,000, 460,000, and 310,000 each year (WHO, 2018). Therefore, the gastrointestinal-related tumors have surpassed lung cancer and become the most common cancer in China. At present, the treatment methods for gastrointestinal tumors mainly include surgery, chemotherapy, targeted therapy and immunotherapy. Commonly used chemotherapy drugs include docetaxel, 5-fluorouracil, mitomycin C, platinum agents, etc.; targeted therapy drugs include VEGFR monoclonal antibody, Her2 monoclonal antibody, etc.; immunotherapy mainly includes PD1/PDL1 antibodies, etc.

The human carcinoembryonic antigen cell adhesion factor (CEACAM) family was discovered in the 1960s. The CEA family is highly expressed in a variety of gastrointestinal and lung cancer tumors, such as colorectal cancer, pancreatic cancer, lung cancer, gastric cancer, hepatocellular carcinoma, breast cancer, etc. CEACAM family consists of CEACAM subgroup and PSG family, and is characterized by IgV domains in series in the extracellular region which form a highly similar structure and are highly glycosylated (glycosylation moiety accounts for 50% of the molecular weight), and its extracellular region consists of A1-B1-A2-B2-A3-B3 structure in series (A1-3 or B1-3 is a highly homologous structure); the common CEA molecule is CEACAM5 (CD66e), which is coupled to the cell membrane through glycosylphosphatidylinositol (GPI), and can be released into the blood through enzymatic degradation of GPI (e.g., phospholipase C); CEACAM5 molecules are involved in cell adhesion (via a CEA family homo- or hetero-dimer, such as CEACAM6), intracellular signaling, tumor metastasis and generation of drug-resistance; at the same time, CEACAM5 is related to the adhesion of *Escherichia coli* in the gastrointestinal tract.

CEACAM5 is a highly glycosylated protein antigen, so the recombinantly expressed CEACAM5 (e.g., 293 system) antigen may have glycosylation different from the CEACAM5 protein expressed by tumor cells itself, so an antibody that can recognize the natural CEACAM5 antigen is needed in the art. In addition, CEACAM5 is expressed in a small amount in normal tissues such as the digestive tract, which is located on the apical surface of the digestive tract; in tumor cells, CEACAM5 is expressed on the apical and basolateral surfaces, and it is difficult for CEACAM5 antibody drugs to reach the tumor site. Therefore, it is needed in the art to address the problem of increasing the local concentration of CEACAM5 antibody drug.

CONTENTS OF THE PRESENT INVENTION

One aspect of the present invention provides a monoclonal antibody or antigen-binding fragment thereof against a glycosylated CEACAM5, and the antibody or antigen-binding fragment thereof specifically binds to the domains A1-B1, A2-B2, and/or A3-B3 of the glycosylated CEACAM5.

In specific embodiments, the monoclonal antibody of the present invention comprises a heavy chain variable region and a light chain variable region, wherein:

- a. the heavy chain variable region comprises: CDR-H1 as set forth in SEQ ID NO: 1, CDR-H2 as set forth in SEQ ID NO: 2, and CDR-H3 as set forth in SEQ ID NO: 3; while the light chain variable region comprises: CDR-L1 as set forth in SEQ ID NO: 4, CDR-L2 as set forth in SEQ ID NO: 5, and CDR-L3 as set forth in SEQ ID NO: 6;
- b. the heavy chain variable region comprises: CDR-H1 as set forth in SEQ ID NO: 7, CDR-H2 as set forth in SEQ ID NO: 8, and CDR-H3 as set forth in SEQ ID NO: 9; while the light chain variable region comprises: CDR-L1 as set forth in SEQ ID NO: 10, CDR-L2 as set forth in SEQ ID NO: 11, and CDR-L3 as set forth in SEQ ID NO: 12;
- c. the heavy chain variable region comprises: CDR-H1 as set forth in SEQ ID NO: 13, CDR-H2 as set forth in SEQ ID NO: 14, and CDR-H3 as set forth in SEQ ID NO: 15; while the light chain variable region comprises: CDR-L1 as set forth in SEQ ID NO: 16, CDR-L2 as set forth in SEQ ID NO: 17, and CDR-L3 as set forth in SEQ ID NO: 18; or
- d. the heavy chain variable region comprises: CDR-H1 as set forth in SEQ ID NO: 19, CDR-H2 as set forth in SEQ ID NO: 20, and CDR-H3 as set forth in SEQ ID NO: 21; while the light chain variable region comprises: CDR-L1 as set forth in SEQ ID NO: 22, CDR-L2 as set forth in SEQ ID NO: 23, and CDR-L3 as set forth in SEQ ID NO: 24.

In a specific embodiment, the monoclonal antibody of the present invention comprises a heavy chain variable region and a light chain variable region, wherein:

- a) the heavy chain variable region comprises a polypeptide as set forth in SEQ ID NO: 25, while the light chain variable region comprises a polypeptide as set forth in SEQ ID NO: 26;
- b) the heavy chain variable region comprises a polypeptide as set forth in SEQ ID NO: 27, while the light chain variable region comprises a polypeptide as set forth in SEQ ID NO: 28;

c) the heavy chain variable region comprises a polypeptide as set forth in SEQ ID NO: 29, while the light chain variable region comprises a polypeptide as set forth in SEQ ID NO: 30; or d) the heavy chain variable region comprises a polypeptide as set forth in SEQ ID NO: 31, while the light chain variable region comprises a polypeptide as set forth in SEQ ID NO: 32.

In one aspect, the present invention provides a humanized antibody or antigen-binding fragment thereof specifically binding to glycosylated CEACAM5, wherein the antibody comprises a light chain variable region and a heavy chain variable region, wherein:

the light chain variable region comprises:
CDR-L1 selected from the group consisting of SEQ ID NO: 84, SEQ ID NO: 90, SEQ ID NO: 96, SEQ ID NO: 102, SEQ ID NO: 108, SEQ ID NO: 114, SEQ ID NO: 120 and SEQ ID NO: 126;
CDR-L2 selected from the group consisting of SEQ ID NO: 85, SEQ ID NO: 91, SEQ ID NO: 97, SEQ ID NO: 103, SEQ ID NO: 109, SEQ ID NO: 115, SEQ ID NO: 121 and SEQ ID NO: 127; and
CDR-L3 selected from the group consisting of SEQ ID NO: 86, SEQ ID NO: 92, SEQ ID NO: 98, SEQ ID NO: 104, SEQ ID NO: 110, SEQ ID NO: 116, SEQ ID NO: 122 and SEQ ID NO: 128,
and the heavy chain variable region comprises:
CDR-H1 selected from the group consisting of SEQ ID NO: 87, SEQ ID NO: 93, SEQ ID NO: 99, SEQ ID NO: 105, SEQ ID NO: 111, SEQ ID NO: 117, SEQ ID NO: 123 and SEQ ID NO: 129;
CDR-H2 selected from the group consisting of SEQ ID NO: 88, SEQ ID NO: 94, SEQ ID NO: 100, SEQ ID NO: 106, SEQ ID NO: 112, SEQ ID NO: 118, SEQ ID NO: 124 and SEQ ID NO: 130; and
CDR-H3 selected from the group consisting of SEQ ID NO: 89, SEQ ID NO: 95, SEQ ID NO: 101, SEQ ID NO: 107, SEQ ID NO: 113, SEQ ID NO: 119, SEQ ID NO: 125 and SEQ ID NO: 131.

In a specific embodiment, in the humanized antibody of the present invention, the light chain variable region comprises an amino acid sequence having at least 90% identity to an amino acid sequence selected from SEQ ID NOs: 68, 70, 72, 74, 76, 78, 80, 82, and the heavy chain variable region comprises an amino acid sequence having at least 90% identity to an amino acid sequence selected from SEQ ID NOs: 69, 71, 73, 75, 77, 79, 81, 83.

In a preferred technical solution, the humanized antibody of the present invention comprises: a light chain variable region encoded by a nucleotide sequence selected from SEQ ID NOs: 52, 54, 56, 58, 60, 62, 64, 66, and a heavy chain variable region encoded by a nucleotide sequence selected from SEQ ID NOs: 53, 55, 57, 59, 61, 63, 65, 67.

In a preferred technical solution, the humanized antibody of the present invention comprises a light chain variable region selected from SEQ ID NOs: 68, 70, 72, 74, 76, 78, 80, 82 and a heavy chain variable region selected from SEQ ID NOs: 69, 71, 73, 75, 77, 79, 81, 83.

In a preferred technical solution, the humanized antibody of the present invention comprises a light chain variable region and a heavy chain variable region, wherein:

a. the light chain variable region comprises: CDR-L1 as set forth in SEQ ID NO: 84, CDR-L2 as set forth in SEQ ID NO: 85 and CDR-L3 as set forth in SEQ ID NO: 86; while the heavy chain variable region comprises: CDR-H1 as set forth in SEQ ID NO: 87, CDR-H2 as set forth in SEQ ID NO: 88 and CDR-H3 as set forth in SEQ ID NO: 89;

b. the light chain variable region comprises: CDR-L1 as set forth in SEQ ID NO: 90, CDR-L2 as set forth in SEQ ID NO: 91 and CDR-L3 as set forth in SEQ ID NO: 92; while the heavy chain variable region comprises: CDR-H1 as set forth in SEQ ID NO: 93, CDR-H2 as set forth in SEQ ID NO: 94 and CDR-H3 as set forth in SEQ ID NO: 95;

c. the light chain variable region comprises: CDR-L1 as set forth in SEQ ID NO: 96, CDR-L2 as set forth in SEQ ID NO: 97 and CDR-L3 as set forth in SEQ ID NO: 98; while the heavy chain variable region comprises: CDR-H1 as set forth in SEQ ID NO: 99, CDR-H2 as set forth in SEQ ID NO: 100 and CDR-H3 as set forth in SEQ ID NO: 101;

d. the light chain variable region comprises: CDR-L1 as set forth in SEQ ID NO: 102, CDR-L2 as set forth in SEQ ID NO: 103 and CDR-L3 as set forth in SEQ ID NO: 104; while the heavy chain variable region comprises: CDR-H1 as set forth in SEQ ID NO: 105, CDR-H2 as set forth in SEQ ID NO: 106 and CDR-H3 as set forth in SEQ ID NO: 107;

e. the light chain variable region comprises: CDR-L1 as set forth in SEQ ID NO: 108, CDR-L2 as set forth in SEQ ID NO: 109 and CDR-L3 as set forth in SEQ ID NO: 110; while the heavy chain variable region comprises: CDR-H1 as set forth in SEQ ID NO: 111, CDR-H2 as set forth in SEQ ID NO: 112 and CDR-H3 as set forth in SEQ ID NO: 113;

f. the light chain variable region comprises: CDR-L1 as set forth in SEQ ID NO: 114, CDR-L2 as set forth in SEQ ID NO: 115 and CDR-L3 as set forth in SEQ ID NO: 116; while the heavy chain variable region comprises: CDR-H1 as set forth in SEQ ID NO: 117, CDR-H2 as set forth in SEQ ID NO: 118 and CDR-H3 as set forth in SEQ ID NO: 119;

g. the light chain variable region comprises: CDR-L1 as set forth in SEQ ID NO: 120, CDR-L2 as set forth in SEQ ID NO: 121 and CDR-L3 as set forth in SEQ ID NO: 122; while the heavy chain variable region comprises: CDR-H1 as set forth in SEQ ID NO: 123, CDR-H2 as set forth in SEQ ID NO: 124 and CDR-H3 as set forth in SEQ ID NO: 125; or h. the light chain variable region comprises: CDR-L1 as set forth in SEQ ID NO: 126, CDR-L2 as set forth in SEQ ID NO: 127 and CDR-L3 as set forth in SEQ ID NO: 128; while the heavy chain variable region comprises: CDR-H1 as set forth in SEQ ID NO: 129, CDR-H2 as set forth in SEQ ID NO: 130 and CDR-H3 as set forth in SEQ ID NO: 131.

In another aspect, the present invention provides an isolated nucleic acid molecule comprising a nucleotide sequence encoding an antibody or antigen-binding fragment thereof specifically binding to glycosylated CEACAM5.

In another aspect, the present invention relates to an expression vector comprising a nucleic acid molecule encoding the antibody specifically binding to glycosylated CEACAM5 as disclosed herein.

In another aspect, the present invention relates to a host cell comprising the expression vectors as disclosed herein.

In another aspect, the present invention relates to a pharmaceutical composition comprising at least one antibody specifically binding to glycosylated CEACAM5 as disclosed herein and a pharmaceutically acceptable carrier.

In another aspect, the present invention relates to a method for preparing an antibody specifically binding to glycosylated CEACAM5, which comprises: expressing in a host cell a nucleic acid sequence encoding the antibody specifically binding to glycosylated CEACAM5 as disclosed herein, and separating the antibody specifically binding glycosylated CEACAM5 from the host cell.

In another aspect, the present invention provides a use of the antibody of the present invention in the manufacture of a medicament for treating a gastrointestinal tract-related tumor.

In another aspect, the present invention provides a method for treating a gastrointestinal tract-related tumor, comprising administering to a subject in need thereof the antibody of the present invention.

Preparation and Screening of Monoclonal Antibodies

Monoclonal antibodies can be prepared as follows. Firstly, mice or other suitable host animals are immunized with an immunogen (added with an adjuvant if necessary). The immunogen or adjuvant is usually injected by subcutaneous multi-point injection or intraperitoneal injection. The immunogen can be pre-coupled to a certain known protein, such as serum albumin or soybean trypsin inhibitor, to enhance the immunogenicity of the antigen in the host. The adjuvant can be Freund's adjuvant or MPL-TDM, etc. After the animal is immunized, lymphocytes that secrete antibodies specifically binding to the immunogen will be produced in the body. In addition, lymphocytes can also be obtained by in vitro immunization. The target lymphocytes are collected and fused with myeloma cells using a suitable fusion agent such as PEG to obtain hybridoma cells (Goding, Monoclonal Antibodies: Principles and Practice, pp. 59-103, Academic Press, 1996). The preferred myeloma cells should have the characteristics of high fusion rate, stable antibody secretion ability, and sensitivity to HAT medium. The culture medium for growing hybridoma cells is used to detect the generation of monoclonal antibodies against specific antigens. Methods for determining the binding specificity of monoclonal antibodies produced by hybridoma cells include, for example, immunoprecipitation or in vitro binding assay, such as radioimmunoassay (RIA), enzyme-linked immunosorbent assay (ELISA). For example, the affinity of monoclonal antibodies can be determined using the Scatchard assay described by Munson et al., Anal. Biochem. 107:220 (1980). After determining the specificity, affinity and reactivity of the antibody produced by the hybridoma, the target cell line can be subjected to subcloning by the standard limited dilution assay described by Goding, Monoclonal Antibodies: Principles and Practice, pp. 59-103, Academic Press, 1996. Suitable culture medium can be DMEM or RPMI-1640, etc. In addition, hybridoma cells can also be grown in animals in the form of ascitic tumors. Monoclonal antibodies secreted by subclonal cells can be isolated from cell culture, ascites, or serum using traditional immunoglobulin purification methods, such as protein A agarose gel, hydroxyapatite chromatography, gel electrophoresis, dialysis, or affinity chromatography, etc.

Monoclonal antibodies can also be obtained through genetic engineering and recombination techniques. The DNA molecules encoding the heavy chain and light chain genes of the monoclonal antibody can be isolated from hybridoma cells by using nucleic acid primers that specifically bind to the heavy chain and light chain genes of the monoclonal antibody to carry out PCR amplification. The resulting DNA molecule is inserted into an expression vector, then transfected into a host cell (e.g., *E. coli* cell, COS cell, CHO cell, or other myeloma cell that does not produce immunoglobulin), and cultured under appropriate conditions, to obtain the antibody of interest as recombinantly expressed.

In the present invention, a tumor cell line (e.g., Lovo) with high expression of CEACAM5 is used to immunize mice to obtain antibodies that recognize natural CEACAM5 antigen.

Through CRISPR technology, sgRNA-guided Cas9 is used to cut the target genome, efficiently knock out gene expression, and construct a CEACAM5 knockout cell line for efficient screening of specific CEACAM5 antibodies. The antibody screened and obtained by the present invention binds to the three structural domains (A1-B1, A2-B2, A3-B3) at of CEACAM5 the same time, so it can increase the surface binding amount of tumor cells with high CEACAM5 expression, thereby increasing its local concentration and drug efficacy.

Humanized Antibody

The humanization design and screening of the screened murine antibodies may reduce the HAMA (Human Anti Mouse Antibody) effect in clinical applications, thereby reducing the production of neutralizing antibodies in patients, and increasing the blood concentration of the drug to improve the efficacy.

A "humanized antibody" is an antibody comprising one or both of a humanized VH domain and a humanized VL domain. The one or more immunoglobulin constant regions need not be present, but if present, they are derived entirely or substantially from human immunoglobulin constant regions.

Humanized antibodies are genetically engineered antibodies in which CDRs from a non-human "donor" antibody are grafted into human "recipient" antibody sequences (see, for example, Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The recipient antibody sequence can be, for example, a mature human antibody sequence, a complex of such sequence, a consensus sequence or germline sequence of human antibody sequence. The human recipient sequence can be chosen such that the variable region framework has a high degree of sequence identity to the donor sequence to match typical patterns and other criteria between the recipient and donor CDRs. Thus, a humanized antibody is an antibody in which CDRs are derived entirely or substantially from the donor antibody and variable region framework sequences, and constant regions (if present) are derived entirely or substantially from human antibody sequences. Similarly, a humanized heavy chain typically has all three CDRs derived substantially from donor antibody heavy chain and heavy chain variable region framework sequences, and heavy chain constant regions (if present) derived substantially from human heavy chain variable region framework and constant region sequences. Similarly, a humanized light chain typically has all three CDRs derived entirely or substantially from donor antibody light chain and light chain variable region framework sequences, and light chain constant regions (if present) derived substantially from human light chain variable region framework and constant region sequences. When at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the corresponding residues (as defined by Kabat numbering system) are identical between the respective CDRs, or about 100% of the corresponding residues (as defined by Kabat numbering system) are identical, the CDRs in a humanized antibody are substantially derived from the corresponding CDRs in a non-human antibody. When at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the corresponding residues (variable regions are defined by Kabat numbering system and constant regions are defined by EU numbering system) are identical, or about 100% of the corresponding residues (variable regions are defined by Kabat numbering system and constant regions are defined by EU numbering system) are identical, the variable region framework sequences of the antibody chains or the constant regions of the antibody chains, respectively, are substantially derived from human variable region framework sequences or human constant regions.

While humanized antibodies often incorporate all six CDRs (preferably as defined by Kabat or IMGT) from a mouse antibody, the humanized antibodies can also be composed of fewer than all six CDRs (e.g., at least 3, 4 or 5 CDRs) from the mouse antibody (e.g., Pascalis et al., J. Immunol. 169:3076, 2002; Vajdos et al., Journal of Molecular Biology, 320:415-428, 2002; Iwahashi et al., Mol. Immunol. 36:1079-1091, 1999; Tamura et al., Journal of Immunology, 164:1432-1441, 2000).

A CDR in a humanized antibody is "substantially derived from" the corresponding CDR in a non-human antibody, when at least 60%, at least 85%, at least 90%, at least 95% or 100% of the corresponding residues (as defined by Kabat or IMGT) are identical between respective CDRs. In specific changes in which the CDRs are substantially derived from a humanized VH or VL domain of a non-human immunoglobulin, the CDRs of the humanized VH or VL domain span all three CDRs with respect to the corresponding non-human VH or VL CDRs, and have no more than six (e.g., no more than 5, no more than 4, no more than 3, no more than 2, or no more than 1) amino acid substitutions (preferably conservative substitutions). When at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the corresponding residues (variable regions are defined by Kabat numbering system and constant regions are defined by EU numbering system) are identical, or about 100% of the corresponding residues (variable regions are defined by Kabat numbering system and constant regions are defined by EU numbering system) are identical, variable region framework sequences of antibody VH or VL domains or immunoglobulin constant region sequences (if present) are "substantially derived from" human VH or VL framework sequences or human constant regions, respectively. Thus, all portions of a humanized antibody (except CDRs) will usually be derived entirely or substantially from the corresponding portions of native human immunoglobulin sequences.

Definitions of General Terms

In the present invention, unless otherwise specified, the scientific and technical terms used herein have the meanings commonly understood by those skilled in the art. Moreover, the laboratory operation steps of cell culture, molecular genetics, nucleic acid chemistry, and immunology used herein are all routine steps widely used in the corresponding fields. Meanwhile, in order to better understand the present invention, definitions and explanations of relevant terms are provided below.

As used herein, the term "antibody" refers to an immunoglobulin molecule, usually composed of two pairs of polypeptide chains (each pair having a light chain and a heavy chain). Antibody light chains can be classified as κ and λ light chains. Heavy chains can be classified as μ, δ, γ, α, or ε, and the antibody isotypes are respectively defined as IgM, IgD, IgG, IgA, and IgE. Within the light and heavy chains, the variable and constant regions are joined by a "J" region of about 12 or more amino acids, while the heavy chain also comprises a "D" region of about 3 or more amino acids. Each heavy chain is composed of a heavy chain variable region (VH) and a heavy chain constant region (CH). The heavy chain constant region consists of 3 domains (CH1, CH2 and CH3). Each light chain is composed of a light chain variable region (VL) and a light chain constant region (CL). The light chain constant region consists of one domain, CL. The constant regions of antibodies can mediate the binding of immunoglobulin to host tissues or factors, including various immune system cells (e.g., effector cells) and the first component (Clq) of classical complement system. The VH and VL regions can also be subdivided into regions of high variability called complementarity determining regions (CDRs) interspersed with more conserved regions called framework regions (FRs). Each VH and VL consists of 3 CDRs and 4 FRs arranged in the following order: FR1, CDR1, FR2, CDR2, FR3, CDR3, FR4, from amino-terminal to carboxy-terminal. The variable regions (VH and VL) of each heavy chain/light chain pair form the antibody binding site, respectively. Assignment of amino acids to regions or domains follows the definitions of the Kabat Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342:878-883. The term "antibody" is not limited to any particular method of producing antibodies. For example, it includes recombinant antibodies, monoclonal antibodies and polyclonal antibodies. The antibody can be of a different isotype, for example, IgG (e.g., IgG1, IgG2, IgG3 or IgG4 subtype), IgA1, IgA2, IgD, IgE or IgM antibody.

Herein, unless the context clearly dictates otherwise, when the term "antibody" is referred to, it includes not only entire antibody but also antigen-binding fragment of the antibody. As used herein, the term "antigen-binding fragment" of antibody refers to a polypeptide comprising a fragment of a full-length antibody, which retains the ability to specifically bind to the same antigen to which the full-length antibody binds, and/or competes with the full-length antibody for specifically binding to antigen, which is also referred to as an "antigen-binding moiety". See generally, Fundamental Immunology, Ch. 7 (Paul, W., ed., 2nd ed., Raven Press, N.Y. (1989), which is incorporated herein by reference in its entirety for all purposes. Antigen-binding fragments of antibody can be obtained by recombinant DNA techniques or by enzymatic or chemical cleavage of intact antibody. In some cases, the antigen-binding fragments include Fab, Fab', F(ab')$_2$, Fd, Fv, dAb, and complementarity determining region (CDR) fragments, single chain antibody (e.g., scFv), chimeric antibody, diabody, and polypeptide comprising at least a portion of antibody sufficient to confer to the polypeptide the specific antigen-binding ability.

Antigen-binding fragments of antibody (e.g., the antibody fragments described above) can be obtained from a given antibody using conventional techniques known to those of skill in the art (e.g., recombinant DNA techniques or enzymatic or chemical fragmentation methods), and can be used to screen antigen-binding fragment of antibody for specificity in the same manner as the intact antibody.

As used herein, the terms "mAb" and "monoclonal antibody" refer to an antibody or a fragment of antibody derived from a population of highly homogeneous antibody molecules, that is, a group of identical antibody molecules excluding natural mutations that may occur spontaneously. The mAbs are highly specific for a single epitope on an antigen. Compared with monoclonal antibodies, polyclonal antibodies usually contain at least two or more different antibodies, and these different antibodies usually recognize different epitopes on antigens. Monoclonal antibodies can usually be obtained by hybridoma technology first reported by Kohler et al. (Nature, 256:495, 1975), but can also be obtained by recombinant DNA technology (see, for example, U.S. Pat. No. 4,816,567).

For example, monoclonal antibodies can be prepared as follows. Mice or other suitable host animals are first immunized in injection manner with immunogen (added with an adjuvant if necessary). The immunogen or adjuvant is usually injected subcutaneously at multiple points or intraperitoneally. The immunogen can be pre-coupled to certain known proteins, such as serum albumin or soybean trypsin inhibitor, to enhance the immunogenicity of the antigen in the host. The adjuvant can be Freund's adjuvant or MPL-TDM, etc. After the animal is immunized, lymphocytes that secrete antibodies that specifically bind to the immunogen will be produced in the body. In addition, lymphocytes can also be obtained by in vitro immunization. The lymphocytes of interest are collected and fused with myeloma cells using a suitable fusion agent, such as PEG, to obtain hybridoma cells (Goding, Monoclonal Antibodies: Principles and Practice, pp. 59-103, Academic Press, 1996). The hybridoma cells prepared above can be inoculated to grow in a suitable culture medium, which preferably contains one or more substances capable of inhibiting the growth of unfused, parental myeloma cells. For example, for parental myeloma cells lacking hypoxanthine guanine phosphotransferase (HGPRT or HPRT), adding substances such as hypoxanthine, aminopterin, and thymine (HAT medium) to the culture medium will inhibit the growth of HGPRT-defective cells. The preferred myeloma cells should have the characteristics of high fusion rate, stable antibody secretion ability, and sensitivity to HAT medium. Among them, the first choice for myeloma cells is murine myeloma, such as MOP-21 or MC-11 mouse tumor derivative strain (THE Salk Institute Cell Distribution Center, San Diego, Calif USA), and SP-2/0 or X63-Ag8-653 cell line (American Type Culture Collection, Rockville, Md. USA). In addition, there are also research reports, in which human myeloma and human mouse heteromyeloma cell lines are used to prepare human monoclonal antibodies (Kozbor, J. Immunol., 133: 3001 (1984); Brodeur et al., Monoclonal Antibody Production Techniques and Applications, pp 51-63, Marcel Dekker, Inc., New York, 1987). The culture medium for growing hybridoma cells is used to detect the production of monoclonal antibodies against specific antigens. Methods for determining the binding specificity of monoclonal antibodies produced by hybridoma cells include, for example, immunoprecipitation or in vitro binding assay, such as radioimmunoassay (MA), enzyme-linked immunosorbent assay (ELISA). For example, the affinity of mAbs can be determined using the Scatchard assay described by Munson et al., Anal. Biochem. 107:220 (1980). After determining the specificity, affinity and reactivity of the antibody produced by the hybridoma, the target cell line can be subjected to subcloning by the standard limited dilution assay described by Goding, Monoclonal Antibodies: Principles and Practice, pp. 59-103, Academic Press, 1996. A suitable culture medium can be DMEM or RPMI-1640, etc. In addition, hybridoma cells can also be grown in animals in the form of ascitic tumors. Monoclonal antibodies secreted by subcloned cells can be purified from cell culture fluid, ascites or serum by using traditional immunoglobulin purification methods, such as protein A agarose gel, hydroxyapatite chromatography, gel electrophoresis, dialysis, or affinity chromatography.

Monoclonal antibodies can also be obtained through genetic engineering and recombination techniques. The DNA molecules encoding the heavy chain and light chain genes of the monoclonal antibody can be isolated from hybridoma cells by using nucleic acid primers that specifically bind to the heavy chain and light chain genes of the monoclonal antibody to carry out PCR amplification. The resulting DNA molecule is inserted into an expression vector, then transfected into a host cell (e.g., *E. coli* cell, COS cell, CHO cell, or other myeloma cell that does not produce immunoglobulin), and cultured under appropriate conditions, to obtain the recombinantly expressed antibody of interest.

As used herein, the term "chimeric antibody" refers to an antibody whose light chain and/or heavy chain are partially derived from one antibody (which may be derived from a specific species or belong to a specific antibody class or subclass), and the other part of the light chain or/and heavy chain is derived from another antibody (which may be derived from the same or different species or belong to the same or different antibody class or subclass), but in any case, it still retains the binding activity to the target antigen (U.S. Pat. No. 4,816,567 to Cabilly et al.; Morrison et al., Proc. Natl. Acad. Sci. USA, 81:6851 6855 (1984)).

As used herein, the term "human antibody" refers to an antibody or antibody fragment obtained by replacing all or part of the CDR regions of a humanized antibody or human immunoglobulin (recipient antibody) by the CDR regions of a non-human antibody (donor antibody), in which the donor antibody may be a non-human (for example, mouse, rat or rabbit) antibody with desired specificity, affinity or reactivity. In addition, some amino acid residues in the framework region (FR) of the recipient antibody can also be replaced by amino acid residues of corresponding non-human antibodies, or by amino acid residues of other antibodies, so as to further improve or optimize the performance of the antibody. For more details on humanized antibodies, see, for example, Jones et al., Nature, 321:522 525 (1986); Reichmann et al., Nature, 332:323 329 (1988); Presta, Curr. Op. Struct. Biol., 2:593 596 (1992); and Clark, Immunol. Today 21:397 402 (2000).

As used herein, the term "epitope" refers to a site on an antigen that is specifically bound by an immunoglobulin or an antibody. An "epitope" is also referred to in the art as an "antigenic determinant". Epitopes or antigenic determinants usually consist of chemically active surface groups of molecules such as amino acids or carbohydrates or sugar side chains, and usually have specific three-dimensional structural characteristics as well as specific charge characteristics. For example, an epitope typically comprise at least 3, 4, 5, 6, 7, 8, 9, 10, 11, 12, 13, 14, or 15 consecutive or non-consecutive amino acids in a unique spatial conformation, which may be "linear" or "conformational". See, for example, Epitope Mapping Protocols in Methods in Molecular Biology, Vol. 66, G. E. Morris, Ed. (1996). In a linear epitope, all points of interaction between a protein and an interacting molecule (e.g., antibody) exist linearly along the primary amino acid sequence of the protein. In a conformational epitope, the points of interaction exist across protein amino acid residues that are separated from each other.

As used herein, the term "epitope peptide" refers to a peptide segment on an antigen that can serve as an epitope. In some cases, an epitope peptide alone is capable of being specifically recognized/bound by an antibody directed against the epitope. In other cases, it may be necessary to fuse the epitope peptide to a carrier protein so that the epitope peptide can be recognized by a specific antibody. As used herein, the term "carrier protein" refers to a protein that can act as a carrier for an epitope peptide, i.e., it can insert an epitope peptide at a specific position (e.g., internal, N-terminal or C-terminal of protein), so that the epitope peptide can be presented, so that the epitope peptide can be recognized by the antibody or the immune system. Such carrier proteins are well known to those skilled in the art and include, for example, HPV L1 protein (epitope peptide may be inserted between amino acids 130-131 or between amino acids 426-427 of the protein, see: Slupetzky, K. et al Chimeric papillomavirus-like particles expressing a foreign epitope on capsid surface loops[J]. J Gen Virol, 2001, 82:2799-2804; Varsani, A. et al Chimeric human papillomavirus type 16 (HPV-16) L1 particles presenting the common neutralizing epitope for the L2 minor capsid protein of HPV-6 and HPV-16[J]. J Virol, 2003, 77:8386-8393), HBV core antigen (epitope peptide may be used to replace the amino acids 79-81 of the protein, see: Koletzki, D., et al. HBV core particles allow the insertion and surface exposure of the entire potentially protective region of Puumala hantavirus nucleocapsid protein[J]. Biol Chem, 1999, 380:325-333), woodchuck hepatitis virus core protein (epitope peptide can be used to replace the amino acids 79-81 of the protein, see: Sabine Konig, Gertrud Beterams and Michael Nassal, J. Virol. 1998, 72(6):4997), CRM197 protein (epitope peptide can be linked to the N-terminus or C-terminus of the protein or fragment thereof). Optionally, a linker (e.g., flexible or rigid linker) can be used between the epitope peptide and the carrier protein to facilitate the folding thereof.

Antibodies can be competitively screened for binding to the same epitope using routine techniques known to those of skill in the art. For example, competition and cross-competition studies can be performed to obtain antibodies that compete with each other or cross-compete for binding to an antigen (e.g., influenza virus hemagglutinin protein). A high-throughput method for obtaining antibodies binding to the same epitope based on their cross-competition is described in the International Patent Application WO03/48731. Thus, antibodies and antigen-binding fragments thereof (i.e., antigen-binding portions) that compete with the monoclonal antibodies of the present invention for binding to the same epitope on the influenza virus hemagglutinin protein can be obtained using routine techniques known to those skilled in the art.

As used herein, the term "specific binding" refers to a non-random binding reaction between two molecules, such as the reaction between an antibody and an antigen to which it is directed. In certain embodiments, an antibody that specifically binds to an antigen (or an antibody having specificity to an antigen) refers to an antibody that binds to the antigen with an affinity ($K_D$) of less than about $10^{-5}$ M, such as less than about $10^{-6}$ M, $10^{-7}$ M, $10^{-8}$ M, $10^{-9}$ M or $10^{-10}$ M or less.

As used herein, the term "$K_D$" refers to the dissociation equilibrium constant for a particular antibody-antigen interaction, which is used to describe the binding affinity between an antibody and an antigen. The smaller the equilibrium dissociation constant, the tighter the antibody-antigen binding, and the higher the affinity between the antibody and the antigen. It can be determined using various methods, for example in a BIACORE instrument using surface plasmon resonance (SPR).

As used herein, the terms "hybridoma" and "hybridoma cell line" are used interchangeably, and when the terms "hybridoma" and "hybridoma cell line" are referred to, they also include subclones and progeny cells of hybridomas. For example, when referring to hybridoma cell line 2F4, it also refers to subclones and progeny cells of hybridoma cell line 2F4.

BRIEF DESCRIPTION OF THE DRAWINGS

FIG. 1 shows the results of CEACAM5 gene knockout in Lovo 6-1 cells with high expression of CEACAM5 using a vector (CEACAM5 KO1-3) by the CRISPR method.

FIG. 2 shows the results of CEACAM5 gene knockout in Lovo 6-1 cells with high expression of CEACAM5 using CEACAM5 KO3 vector.

FIG. 3 shows the binding results of mouse monoclonal antibody to CEACAM5 recombinant protein.

FIG. 4 shows the binding of mouse monoclonal antibody to the extracellular domain of CEACAM5.

FIG. 5 shows the binding of mouse monoclonal antibody to LS174T cells and KATO3 cells with high expression of CEACAM5.

FIG. 6 shows the binding of humanized antibody to recombinant CEACAM5 antigen.

FIG. 7 shows the binding of humanized antibody to KATO3 cells with high expression of CEACAM5.

FIG. 8 shows the competitive binding of humanized antibody and murine m2F4 antibody for CEACAM5.

SEQUENCE INFORMATION

Part of the sequence information involved in the present application is described in the table below, and the rest are described in the examples.

| SEQ ID NO: | Description |
|---|---|
| 1 | M19 heavy chain variable region CDR1 |
| 2 | M19 heavy chain variable region CDR2 |
| 3 | M19 heavy chain variable region CDR3 |
| 4 | M19 light chain variable region CDR1 |
| 5 | M19 light chain variable region CDR2 |
| 6 | M19 light chain variable region CDR3 |
| 7 | M7 heavy chain variable region CDR1 |
| 8 | M7 heavy chain variable region CDR2 |
| 9 | M7 heavy chain variable region CDR3 |
| 10 | M7 light chain variable region CDR1 |

-continued

| SEQ ID NO: | Description |
|---|---|
| 11 | M7 light chain variable region CDR2 |
| 12 | M7 light chain variable region CDR3 |
| 13 | M17 heavy chain variable region CDR1 |
| 14 | M17 heavy chain variable region CDR2 |
| 15 | M17 heavy chain variable region CDR3 |
| 16 | M17 light chain variable region CDR1 |
| 17 | M17 light chain variable region CDR2 |
| 18 | M17 light chain variable region CDR3 |
| 19 | M18 heavy chain variable region CDR1 |
| 20 | M18 heavy chain variable region CDR2 |
| 21 | M18 heavy chain variable region CDR3 |
| 22 | M18 light chain variable region CDR1 |
| 23 | M18 light chain variable region CDR2 |
| 24 | M18 light chain variable region CDR3 |
| 25 | M19 heavy chain variable region |
| 26 | M19 light chain variable region |
| 27 | M7 heavy chain variable region |
| 28 | M7 light chain variable region |
| 29 | M17 heavy chain variable region |
| 30 | M17 light chain variable region |
| 31 | M18 heavy chain variable region |
| 32 | M18 light chain variable region |
| 33 | Antibody hMN14 light chain variable region |
| 34 | Antibody hMN14 heavy chain variable region |
| 35 | CEACAM5 KO1 sgRNA sequence |
| 36 | CEACAM5 KO2 sgRNA sequence |
| 37 | CEACAM5 KO3 sgRNA sequence |
| 38 | M19 heavy chain variable region nucleotide sequence |
| 39 | M19 light chain variable region nucleotide sequence |
| 40 | M7 heavy chain variable region nucleotide sequence |
| 41 | M7 light chain variable region nucleotide sequence |
| 42 | M17 heavy chain variable region nucleotide sequence |
| 43 | M17 light chain variable region nucleotide sequence |
| 44 | M18 heavy chain variable region nucleotide sequence |
| 45 | M18 light chain variable region nucleotide sequence |
| 46 | Extracellular domain A1-B1-His nucleotide sequence |
| 47 | Extracellular domain A1-B1-His amino acid sequence |
| 48 | Extracellular domain A2-B2-His nucleotide sequence |
| 49 | Extracellular domain A2-B2-His amino acid sequence |
| 50 | Extracellular domain A3-B3-His nucleotide sequence |
| 51 | Extracellular domain A3-B3-His amino acid sequence |
| 52 | Humanized antibody hAb-009 light chain variable region nucleotide sequence |
| 53 | Humanized antibody hAb-009 heavy chain variable region nucleotide sequence |
| 54 | Humanized antibody hAb-003 light chain variable region nucleotide sequence |
| 55 | Humanized antibody hAb-003 heavy chain variable region nucleotide sequence |
| 56 | Humanized antibody hAb-005 light chain variable region nucleotide sequence |
| 57 | Humanized antibody hAb-005 heavy chain variable region nucleotide sequence |
| 58 | Humanized antibody hAb-006 light chain variable region nucleotide sequence |
| 59 | Humanized antibody hAb-006 heavy chain variable region nucleotide sequence |
| 60 | Humanized antibody hAb-010 light chain variable region nucleotide sequence |
| 61 | Humanized antibody hAb-010 heavy chain variable region nucleotide sequence |
| 62 | Humanized antibody hAb-013 light chain variable region nucleotide sequence |
| 63 | Humanized antibody hAb-013 heavy chain variable region nucleotide sequence |
| 64 | Humanized antibody hAb-016 light chain variable region nucleotide sequence |
| 65 | Humanized antibody hAb-016 heavy chain variable region nucleotide sequence |
| 66 | Humanized antibody hAb-017 light chain variable region nucleotide sequence |
| 67 | Humanized antibody hAb-017 heavy chain variable region nucleotide sequence |
| 68 | Humanized antibody hAb-009 light chain variable region amino acid sequence |
| 69 | Humanized antibody hAb-009 heavy chain variable region amino acid sequence |
| 70 | Humanized antibody hAb-003 light chain variable region amino acid sequence |
| 71 | Humanized antibody hAb-003 heavy chain variable region amino acid sequence |
| 72 | Humanized antibody hAb-005 light chain variable region amino acid sequence |
| 73 | Humanized antibody hAb-005 heavy chain variable region amino acid sequence |
| 74 | Humanized antibody hAb-006 light chain variable region amino acid sequence |
| 75 | Humanized antibody hAb-006 heavy chain variable region amino acid sequence |
| 76 | Humanized antibody hAb-010 light chain variable region amino acid sequence |
| 77 | Humanized antibody hAb-010 heavy chain variable region amino acid sequence |
| 78 | Humanized antibody hAb-013 light chain variable region amino acid sequence |
| 79 | Humanized antibody hAb-013 heavy chain variable region amino acid sequence |
| 80 | Humanized antibody hAb-016 light chain variable region amino acid sequence |
| 81 | Humanized antibody hAb-016 heavy chain variable region amino acid sequence |
| 82 | Humanized antibody hAb-017 light chain variable region amino acid sequence |
| 83 | Humanized antibody hAb-017 heavy chain variable region amino acid sequence |
| 84 | Humanized antibody hAb-009 light chain variable region CDR1 sequence |
| 85 | Humanized antibody hAb-009 light chain variable region CDR2 sequence |
| 86 | Humanized antibody hAb-009 light chain variable region CDR3 sequence |

| SEQ ID NO: | Description |
|---|---|
| 87 | Humanized antibody hAb-009 heavy chain variable region CDR1 sequence |
| 88 | Humanized antibody hAb-009 heavy chain variable region CDR2 sequence |
| 89 | Humanized antibody hAb-009 heavy chain variable region CDR3 sequence |
| 90 | Humanized antibody hAb-003 light chain variable region CDR1 sequence |
| 91 | Humanized antibody hAb-003 light chain variable region CDR2 sequence |
| 92 | Humanized antibody hAb-003 light chain variable region CDR3 sequence |
| 93 | Humanized antibody hAb-003 heavy chain variable region CDR1 sequence |
| 94 | Humanized antibody hAb-003 heavy chain variable region CDR2 sequence |
| 95 | Humanized antibody hAb-003 heavy chain variable region CDR3 sequence |
| 96 | Humanized antibody hAb-005 light chain variable region CDR1 sequence |
| 97 | Humanized antibody hAb-005 light chain variable region CDR2 sequence |
| 98 | Humanized antibody hAb-005 light chain variable region CDR3 sequence |
| 99 | Humanized antibody hAb-005 heavy chain variable region CDR1 sequence |
| 100 | Humanized antibody hAb-005 heavy chain variable region CDR2 sequence |
| 101 | Humanized antibody hAb-005 heavy chain variable region CDR3 sequence |
| 102 | Humanized antibody hAb-006 light chain variable region CDR1 sequence |
| 103 | Humanized antibody hAb-006 light chain variable region CDR2 sequence |
| 104 | Humanized antibody hAb-006 light chain variable region CDR3 sequence |
| 105 | Humanized antibody hAb-006 heavy chain variable region CDR1 sequence |
| 106 | Humanized antibody hAb-006 heavy chain variable region CDR2 sequence |
| 107 | Humanized antibody hAb-006 heavy chain variable region CDR3 sequence |
| 108 | Humanized antibody hAb-010 light chain variable region CDR1 sequence |
| 109 | Humanized antibody hAb-010 light chain variable region CDR2 sequence |
| 110 | Humanized antibody hAb-010 light chain variable region CDR3 sequence |
| 111 | Humanized antibody hAb-010 heavy chain variable region CDR1 sequence |
| 112 | Humanized antibody hAb-010 heavy chain variable region CDR2 sequence |
| 113 | Humanized antibody hAb-010 heavy chain variable region CDR3 sequence |
| 114 | Humanized antibody hAb-013 light chain variable region CDR1 sequence |
| 115 | Humanized antibody hAb-013 light chain variable region CDR2 sequence |
| 116 | Humanized antibody hAb-013 light chain variable region CDR3 sequence |
| 117 | Humanized antibody hAb-013 heavy chain variable region CDR1 sequence |
| 118 | Humanized antibody hAb-013 heavy chain variable region CDR2 sequence |
| 119 | Humanized antibody hAb-013 heavy chain variable region CDR3 sequence |
| 120 | Humanized antibody hAb-016 light chain variable region CDR1 sequence |
| 121 | Humanized antibody hAb-016 light chain variable region CDR2 sequence |
| 122 | Humanized antibody hAb-016 light chain variable region CDR3 sequence |
| 123 | Humanized antibody hAb-016 heavy chain variable region CDR1 sequence |
| 124 | Humanized antibody hAb-016 heavy chain variable region CDR2 sequence |
| 125 | Humanized antibody hAb-016 heavy chain variable region CDR3 sequence |
| 126 | Humanized antibody hAb-017 light chain variable region CDR1 sequence |
| 127 | Humanized antibody hAb-017 light chain variable region CDR2 sequence |
| 128 | Humanized antibody hAb-017 light chain variable region CDR3 sequence |
| 129 | Humanized antibody hAb-017 heavy chain variable region CDR1 sequence |
| 130 | Humanized antibody hAb-017 heavy chain variable region CDR2 sequence |
| 131 | Humanized antibody hAb-017 heavy chain variable region CDR3 sequence |

Specific Models for Carrying Out the Present Invention

The embodiments of the present application will be described in detail below in conjunction with examples, but those skilled in the art will understand that the following examples are only for illustrating the present application, rather than limiting the scope of the present application. Various objects and advantages of the present application will become apparent to those skilled in the art from the following detailed description of the preferred embodiments.

Example 1. Preparation of Monoclonal Antibodies

In this example, a tumor cell line expressing CEACAM5 was used to immunize mice to prepare monoclonal antibodies.

1. SJL Mouse Immunization/Hybridoma Fusion

The Lovo cell line ATCC CCL-229, which highly expressed CEACAM5, was cultured in RPMI1640 medium containing 10% FBS. After the Lovo cells were digested with TrypLE trypsin, they were resuspended in DPBS solution, and each SJL mouse was subcutaneously immunized at multiple points, $10^7$ Lovo cells were immunized per time, once a week, 5 times in total. After the mice tested for serum titer were sacrificed, the spleen was taken, ground and sieved, and SP20 myeloma cells were fused according to the standard fusion procedure to obtain hybridoma cells.

2. Construction and Screening of Lovo CEACAM5 KO Cell Line 2.1 Screening of Monoclonal Cell Line with High Expression of Lovo CEACAM5

The Lovo cells were labeled with anti-CEACAM5 antibody hMN14 (Immunomedics, Phase 2 drug), expressed through recombination, and the sequence was as follows

```
>hMN14 VH
                                    (SEQ ID NO: 34)
EVQLVESGGGVVQPGRSLRLSCSASGFDFT

TYWMSWVRQAPGKGLEWIGEIHPDSSTINY

APSLKDRFTISRDNAKNTLFLQMDSLRPED

TGVYFCASLYFGFPWFAYWGQGTPVTVSSA

STKGPSVFPLAPSSKSTSGGTAALGCLVKD

YFPEPVTVSWNSGALTSGVHTFPAVLQSSG
```

-continued

LYSLSSVVTVPSSSLGTQTYICNVNHKPSN

TKVDKKVEPKSCDKTHTCPPCPAPELLGGP

SVFLFPPKPKDTLMISRTPEVTCVVVDVSH

EDPEVKFNWYVDGVEVHNAKTKPREEQYNS

TYRVVSVLTVLHQDWLNGKEYKCKVSNKAL

PAPIEKTISKAKGQPREPQVYTLPPSREEM

TKNQVSLTCLVKGFYPSDIAVEWESNGQPE

NNYKTTPPVLDSDGSFFLYSKLTVDKSRWQ

QGNVFSCSVMHEALHNHYTQKSLSLSPGK

>hMN14 VL
(SEQ ID NO: 33)
DIQLTQSPSSLSASVGDRVTITCKASQDVG

TSVAWYQQKPGKAPKLLIYWTSTRHTGVPS

RFSGSGSGTDFTFTISSLQPEDIATYYCQQ

YSLYRSFGQGTKVEIKRTVAAPSVFIFPPS

DEQLKSGTASVVCLLNNFYPREAKVQWKVD

NALQSGNSQESVTEQDSKDSTYSLSSTLTL

SKADYEKHKVYACEVTHQGLSSPVTKSFNR

GEC,

After labeling, anti-mouse Fc-PE fluorescence-labeled secondary antibody was added, sorted into 96-well plate by BD FACS Aria, after monoclonal culture was carried out, MN14 was used to detect the expression of monoclonal CEACAM5, and the results were as follows:

| Clone | CEACAM5 positive ratio, % | CEACAM5 positive MFI |
|---|---|---|
| Lovo + second antibody | 0.3% | NA |
| 1-1 | 90.5% | 1105790 |
| 1-2 | 95.6% | 783976 |
| 2-1 | 95.6% | 1009535 |
| 2-2 | 96.4% | 999722 |
| 3-1 | 97.8% | 915297 |
| 3-2 | 95.9% | 974630 |
| 4-1 | 93.7% | 904109 |
| 4-2 | 82.7% | 1142303 |
| 5-1 | 76.6% | 513840 |
| 5-2 | 96.9% | 1053108 |
| 6-1 | 98.6% | 1470927 |
| 6-2 | 88.1% | 751552 |
| 7-1 | 93.9% | 759412 |
| 7-2 | 96.9% | 990410 |
| 8-1 | 97.9% | 1188614 |
| 8-2 | 96.8% | 1099974 |

The above results showed that clone 6-1 had a higher purity than other clones, reaching 98.6%, and its CEACAM5 expression MFI was significantly higher than other clones, so that clone 6-1 was selected for CEACAM5 knockout.

2.2 Screening of Lovo CEACAM5 KO Cell Line

The Lovo 6-1 clone was subjected to CEACAM5 gene knockout by the CRISPR method, and the Lovo CEACAM5 KO cell line (hereinafter referred to as the Lovo CEA KO cell line) was screened. The vector carrying CRISPR and sgRNA was packaged into a lentiviral vector (CEACAM5 KO1-3) and transduced into Lovo 6-1 cells. After transduction, CEACAM5 expression (MN14 antibody) was detected by FACS, and MN14 binding was detected by mouse Fc-APC secondary antibody. The results were shown in FIG. 1. The results showed that CEACAM5 KO1-3 could knock out CEACAM5, and the knockout efficiency of CEACAM5 KO3 vector was higher, which was manifested that the CEACAM5-negative population was more clear. The sequences of the three sgRNAs targeting CEACAM5 were as follows:

| No. | sgRNA |
|---|---|
| CEACAM5 KO1 | GATCTGACTTTATGACGTGT (SEQ ID NO: 35) |
| CEACAM5 KO2 | GATGACTGAATCACTGCGCC (SEQ ID NO: 36) |
| CEACAM5 KO3 | CAGGGGATGCACCATCTGTG (SEQ ID NO: 37) |

Figure 2:
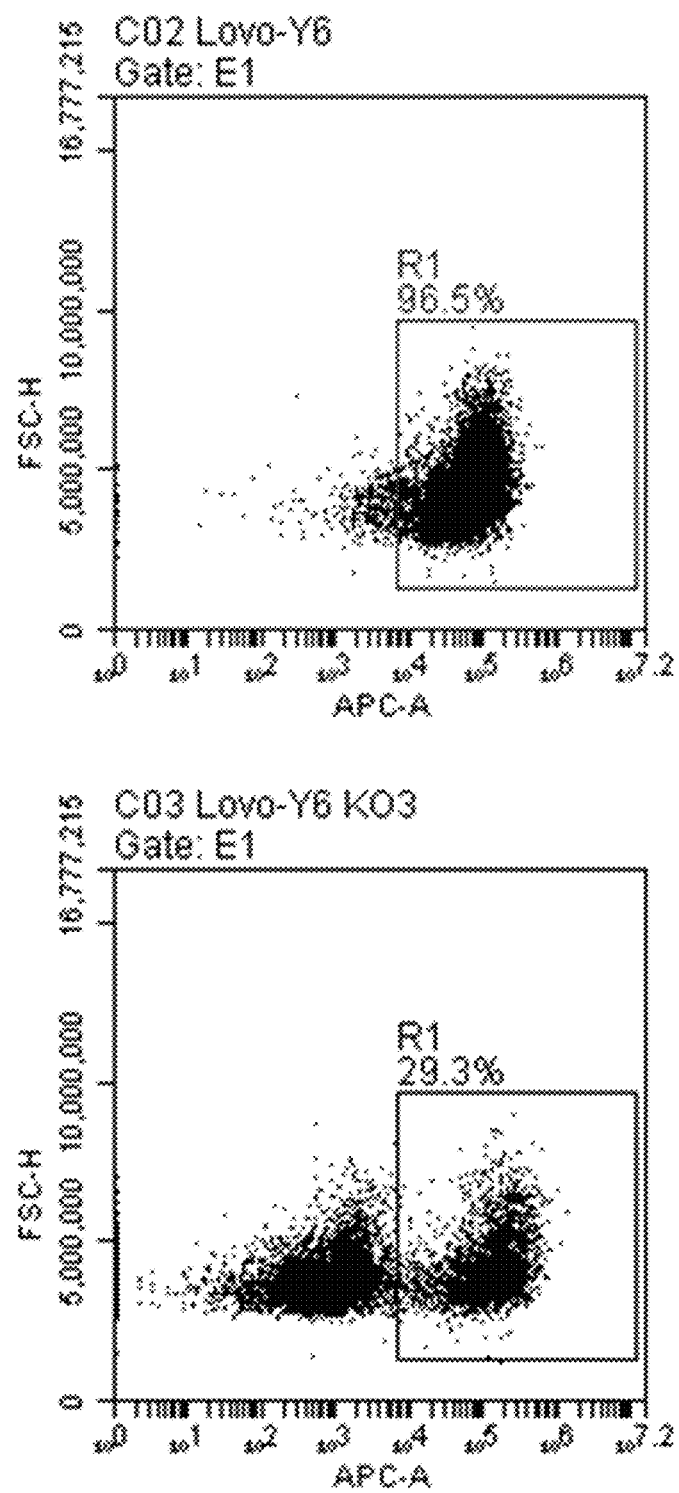

As shown in FIG. 2, after the Lovo 6-1 clone was subjected to CEACAM5 knockout by CRISPR method, CEACAM5 knockout population appeared in the cell population, accounting for 100% to 29.3%, indicating that CEACAM5 knockout was successfully carried out.

3. Hybridoma Cloning and Screening

Lovo cells and Lovo CEA KO cells were inoculated in 96-well plates, $10^4$ per well, and cultured overnight, 1-10 μl of hybridoma supernatant was added to Lovo/Lovo CEA KO cell culture plates, incubated for 1 hour, the supernatant was discarded, anti-mouse Fc-FITC fluorescent secondary antibody was added, incubated for 1 hour, the supernatant was discarded, DPBS solution containing 2% BSA was added, the fluorescent signals and FITC staining areas were read and analyzed in Celigo.

Four clones of M19 (2F4), M7 (11B6), M17 (6A8) and M18 (7G1) were obtained by screening.

| Clone | Lovo binding percentage | Lovo CEA KO binding percentage |
|---|---|---|
| M7 | 54.6% | 0.5% |
| M17 | 34.7% | 1.1% |
| M18 | 89.5% | 0.7% |
| M19 | 78.4% | 0.3% |

4. Hybridoma Sequencing/Recombinant Expression Vector Construction

Four clones of M19 (2F4), M7 (11B6), M17 (6A8) and M18 (7G1) were obtained by screening. The selected hybridoma clones were sequenced according to the standard hybridoma sequencing method to obtain the heavy chain and light chain variable regions (VH and VL) of the selected clones. The VH and VL were synthesized through whole gene synthesis and ligated to human IgG1 and kappa chain constant regions, and the heavy chain and light chain sequences were ligated to pcDNA3.4 vector, subjected to transient expression in the 293 system and purified by protein A/G. The obtained chimeric recombinant antibody was subjected to ultrafiltration for buffer replacement with PBS solution. The sequencing results were shown in the table below.

| Clone | VL and VH sequences (CDR Kabat Numbering, underline indicates CDR region) |
|---|---|
| M19 (2F4) | >VL<br>(SEQ ID NO: 39)<br>ATGGGCTGGAGCTGCATCATCCTGT<br>TCCTCGTGGCCACAGCTACAGGAGT<br>GCATAGCGACATCCAGCTGACCCAG |

| Clone | VL and VH sequences (CDR Kabat Numbering, underline indicates CDR region) |
|---|---|
| | TCTCCTAGCAGCCTGAGCGCCAGCG<br>TGGGAGATAGAGTGACCATCACTTG<br>CAGAGCCAGCAGCAGCGTGTCCTAC<br>ATCCATTGGTACCAGCAGAAGCCCG<br>GCAAGAGCCCTAAGCCTTGGATTCA<br>CGGCACCAGCAATCTGGCCAGCGGA<br>GTGCCTAGCAGATTCAGCGGCAGCG<br>GAAGCGGCACCGATTACACCCTGAC<br>CATCAGCTCTCTGCAGCCAGAGGAC<br>GCAGCCACCTACTATTGCCAGCAGT<br>GGAGCAGCAACCTGAGCACCTTTGG<br>CCAGGGAACCAAGCTGGAGATCAAG<br><br>(SEQ ID NO: 26)<br>MGWSCHILFLVATATGVHSDIQLTQ<br>SPSSLSASVGDRVTITC<u>RASSSVSY</u><br><u>IH</u>WYQQKPGKSPKPWIH<u>GTSNLASG</u><br>VPSRFSGSGSGTDYTLTISSLQPED<br>AATYYC<u>QQWSSNLSTF</u>GQGTKLEIK<br><br>>VH<br>(SEQ ID NO: 38)<br>ATGGGCTGGAGCTGCATCATCCTGT<br>TCCTCGTGGCCACAGCTACAGGAGT<br>GCATAGCGAGGTGCAGCTGGTGGAA<br>TCAGGAGGAGGACTGGTGCAGCCAG<br>GAGGATCTCTGAGACTGTCTTGCGC<br>CGCCAGCGGCTTTACATTCACCGAC<br>TACTTCATGAATTGGGTCCGGCAGG<br>CCCCAGGAAAAGCACTCGAGTGGCT<br>GGGACAGATGCGGAACAAGGTCAAC<br>GGCGACACCACAGAGTACGCCGAAA<br>GCGTGGAGGGCAGATTCACCATCAG<br>CCGGGACATCAGCAAGAACAGCCTG<br>TACCTGCAGATGAACAGCCTGAAGA<br>CCGAGGATACCGCCGTGTACTATTG<br>CGCCAGGGACAAGGGCATCGCCTAC<br>TACTTCGACTACTGGGGCCAGGGAA<br>CACTGGTGACAGTGTCT<br><br>(SEQ ID NO: 25)<br>MGWSCHILFLVATATGVHSEVQLVE<br>SGGGLVQPGGSLRLSCAASGFTFTD<br><u>YFMN</u>WVRQAPGKALEWLG<u>QMRNKVN</u><br><u>GDTTEYAESVEG</u>RFTISRDISKNSL<br>YLQMNSLKTEDTAVYYCAR<u>DKGIAY</u><br><u>YFDY</u>WGQGTLVTVSS |
| M7 (11B6) | >VL<br>(SEQ ID NO 41)<br>CAAATTGTTCTCACCCAGTCTCCAG<br>CAATCATGTCTGCTTCTCCAGGGGA<br>GAAGGTCACCATCACCTGCAGTGCC<br>ACCTCAAGTGTAAGTTACATGCACT<br>GGTTCCAGCAGAAGCCAGGCACTTC<br>TCCCAAACTCTGGATTTATAGCACA<br>TCCAACCTGGCTTCTGGAGTCCCTG<br>CTCGCTTCAGTGGCAGTGGATCTGG<br>GACCTCTTACTCTCTCACAATCAGC<br>CGAGTGGAGGCTGAAGATGCTGCCA<br>CTTATTACTGCCAGCAAAGGAGTAG<br>TTACCCGCTCACGTTCGGTGCTGGG<br>ACCAAGCTGGAGCTGAAA<br><br>(SEQ ID NO: 28)<br>QIVLTQSPAIMSASPGEKVTITC<u>SA</u><br><u>TSSSVSYMH</u>WFQQKPGTSPKLWIY<u>ST</u><br><u>SNLASG</u>VPARFSGSGSGTSYSLTIS<br>RVEAEDAATYYC<u>QQRSSYPLT</u>FGAG<br>TKLELK<br><br>>VH<br>(SEQ ID NO: 40)<br>GAGGTTCAGCTGCAGCAGTCTGGGG<br>CTGAGCTTGTGAGGCCAGGGGCCTC |
| | AGTCAAGTTGTCCTGCACAGTTTCT<br>GGCTTTAACATTAAAGACGACTATA<br>TGCACTGGGTGAAGCAGAGGCCTGA<br>ACAGGGCCTGGAGTGGATTGGATGG<br>ATTGATCCTGAGAATGGTGATACTG<br>AATATGCCTCGAAGTTCCAGGGCAA<br>GGCCACTATAACAGCAGACACATCC<br>TCCAACTCAGCCTACCTGCAGCTCA<br>GCAGCCTGACATCTGAGGACACTGC<br>CGTCTATTACTGTACTTTTATCTAC<br>TATGTTAATCCTCATTACTATGCTA<br>TGGACTACTGGGGTCAAGGAACCTC<br>AGTCACCGTCTCCTCA<br><br>(SEQ ID NO: 27)<br>EVQLQQSGAELVRPGASVKLSCTVS<br>GFNIKDDYMHWVKQRPEQGLEWIGW<br><u>IDPENGDTEYASKFQG</u>KATITADTS<br>SNSAYLQLSSLISEDTAVYYC<u>TEIY</u><br><u>YVNPHYYAMDY</u>WGQGTSVTVSS |
| M17 (6A8) | >VL<br>(SEQ ID NO: 43)<br>CAAATTGTTCTCACCCAGTCTCCAG<br>CAATCATGTCTGCATCTCCAGGGGA<br>GAAGGTCACCATAACCTGCAGTGCC<br>AGCTCAAGTGTAAGTTACATGCACT<br>GGTTCCAGCAGAAGCCAGGCACTTC<br>TCCCAAACTCTGGATTTATACCACA<br>TCCACCCTGGCTTCTGGAGTCCCTG<br>CTCGCTTCAGTGGCAGTGGATCTGG<br>GACCTCTTACTTTCTCACAATCAGC<br>CGAATGGAGGCTGAAGATGCTGCCA<br>CTTATTACTGCCACCAAAGGAGTAG<br>TTACCCACTCACGTTCGGTGCTGGG<br>ACCAAGCTGGAGCTGAAA<br><br>(SEQ ID NO: 30)<br>QIVLTQSPAIMSASPGEKVTITC<u>SA</u><br><u>SSSSVSYMH</u>WFQQKPGTSPKLWIY<u>TT</u><br><u>STLASG</u>VPARFSGSGSGTSYFLTIS<br>RMEAEDAATYYC<u>HQRSSYPLT</u>FGAG<br>TKLELK<br><br>>VH<br>(SEQ ID NO: 42)<br>GAGGTTCAGCTGCAGCAGTCTGGGG<br>CTGAGCTTGTGAGGCCAGGGGCCTC<br>AGTCAAGTTGTCCTGCACAGCTTCT<br>GGCTTTAACATTAAAGACGACTATA<br>TGCACTGGGTGAAGCAGAGGCCTGA<br>ACAGGGCCTGGAGTGGATTGGATGG<br>ATTGATCCTGAGAATGGTGATACTG<br>AATATGCCTCGAAGTTCCAGGGCAA<br>GGCCACTATAACAGCAGACACATCC<br>TCCAACACAGCCTACCTGCTGCTCA<br>GCAGCCTGACATCTGAGGACACTGC<br>CGTCTATTACTGTACTACCATTTAT<br>TACTACGGTAGTAGAGGTGCTATGG<br>ACTACTGGGGTCAAGGAACCTCAGT<br>CACCGTCTCCTCA<br><br>(SEQ ID NO: 29)<br>EVQLQQSGAELVRPGASVKLSCTAS<br>GFNIKDDYMHWVKQRPEQGLEWIGW<br><u>IDPENGDTEYASKFQG</u>KATITADTS<br>SNTAYLLLSSLTSEDTAVYYCTT<u>IY</u><br><u>YYGSRGAMDY</u>WGQGTSVTVSS |
| M18 (7G1) | >VL<br>(SEQ ID NO: 45)<br>GGAGGCAAAGTCACCATCACTTGCA<br>AGACAAGCCAAGACATTAACAAGTT |

| Clone | VL and VH sequences (CDR Kabat Numbering, underline indicates CDR region) |
|---|---|
| | TATGGCTTGGTACCAACACAAGCCT<br>GGAAAAGGTCCTAGGCTGCTCATAC<br>GTTACACATCTACATTACAGCCAGG<br>CATCCCATCAAGGTTCAGTGGAAGT<br>GGGTCTGGGAGAGATTATTCCTTCA<br>GCATCAGGAACCTGGAGCCTGAAGA<br>TATTGCAACTTATTATTGTCTACAG<br>TATGATGATCTTACGTGGACGTTCG<br>GTGGAGGCACCAAGCTGGAAATC<br><br>(SEQ ID NO: 32)<br>DIQMTQSPSSLSASLGGKVTITCKT<br>SQDINKFMAWYQHKPGKGPRLLIRY<br>TSTLQPGIPSRFSGSGSGRDYSFSI<br>RNLEPEDIATYYCLQYDDLTWTFGG<br>GTKLEI<br><br>>VH<br>(SEQ ID NO: 44)<br>CAGATCCAGTTGGTACAGTCTGGAC<br>CTGAGCTGAAGAAGCCTGGAGAGAC<br>AGTCAAGATCTCCTGCAAGGCTTCT<br>GGGTATACCTTTACAACCTATGGAA<br>TGACCTGGGTGAAACAGGCTCCAGG<br>AAAGGGTTTAAAGTGGATGGGCTGG<br>ATAAACACCTACTCTGGAGTGCCAA<br>CATATATTGATGACTTCAAGGGACG<br>GTTTGCCTTCTCTTTGGAAACCTCT<br>GCCAGCACTGCCTATTTGCAGATCA<br>ACAACCTCAAAAATGAGGACACGGC<br>TACATATTTCTGTGGAAGAAAGGAT<br>CTACTTGGTTTTATGGACTACTGGG<br>GTCAAGGAACCTCAGTCACCGTCTC<br>CTCAGACATCCAGATGACACAGTCT<br>CCATCCTCACTGTCTGCATCTCTG<br><br>(SEQ ID NO: 31)<br>QIQLVQSGPELKKPGETVKISCKAS<br>GYTFTTYGMTWVKQAPGKGLKW<br>MGWINTYSGVPTYIDDFKGRFAFSL<br>ETSASTAYLQINNLKNEDTATYFC<br>GRKDLLGEMDYWGQGTSVTVSS |

Example 2. ELISA Experiment of Antigen Binding

Figure 3:
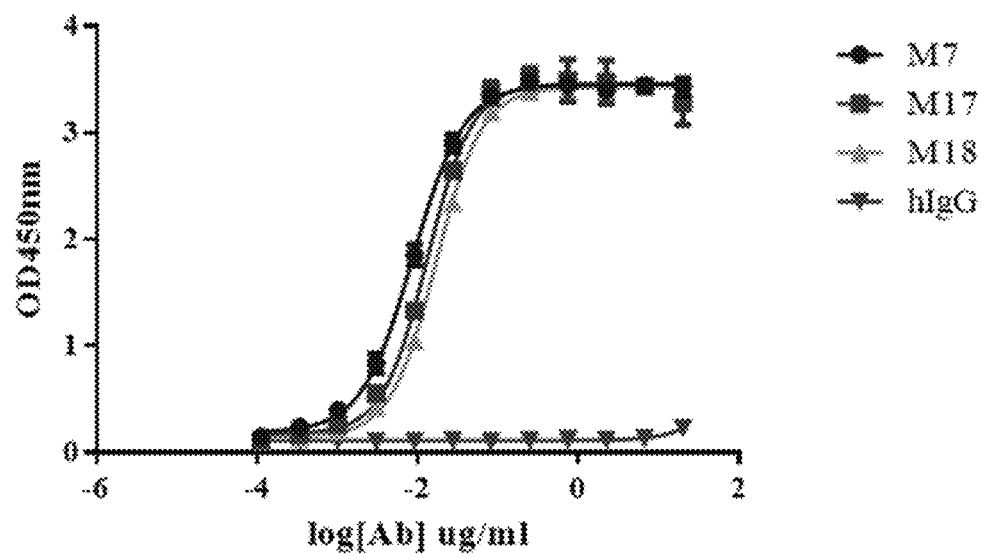
Figure 3:
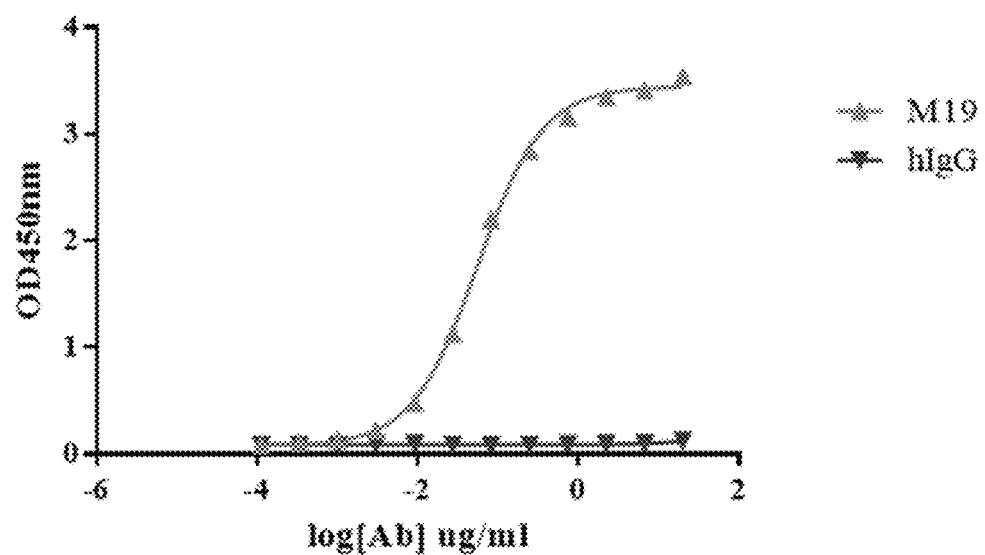

The recombinant CEACAM5 antigen (Sinobiological, 11077-H08H) was diluted to 1 μg/ml with DPBS solution, added to a 96-well plate, 100 μl per well, and coated overnight at 2-8° C.; the coating solution was discarded, washing was performed twice with PBS solution, PBS solution containing 2% BSA was added, and blocked at room temperature for 2 hours; the blocking solution was discarded, the antibody diluted in concentration gradient was added, and incubated at 37° C. for 1 hour; the antibody solution was discarded, and washing was performed for 4 times with with PBS solution containing 0.05% Tween 20 (PBST solution); anti-human IgG Fc-HRP secondary antibody was added and incubated at 37° C. for 30 minutes; washing was performed for 4 times with PBST solution, TMB chromogenic substrate was added, color development was performed for 5-10 minutes, and the reaction was terminated with equal volume of 1M H2SO4; the absorbance at 450 nm was read on a microplate reader. The binding results of the above four antibodies M7, M17, M18, and M19 to CEACAM5 recombinant protein were shown in FIG. 3 and the table below. The results showed that all the above four antibodies could bind CEACAM5-His recombinant protein.

| Antibody | EC50, μg/ml |
|---|---|
| M7 | 0.008 |
| M17 | 0.013 |
| M18 | 0.016 |
| M19 | 0.055 |

Example 3. Experiment Antibody-Epitope Binding

The CEACAM5 molecule was split according to its extracellular domains (A1-B1-A2-B2-A3-B3), A1-B1-His Tag, A2-B2-His Tag, A3-B3-His Tag expression vectors were constructed, and purified using Ni column after being expressed in the 293 system, and their sequences were shown in the table below:

| Extracellular domain | Nucleotide sequence/amino acid sequence (underline indicates signal peptide) |
|---|---|
| A1-B1-His | SEQ ID NO: 46<br>ATGCACAGCTCAGCACTGCTCTGTTGCCTG<br>GTCCTCCTGACTGGGGTGAGGGCCAAGCTC<br>ACTATTGAATCCACGCCGTTCAATGTCGCA<br>GAGGGGAAGGAGGTGCTTCTACTTGTCCAC<br>AATCTGCCCCAGCATCTTTTTGGCTACAGC<br>TGGTACAAAGGTGAAAGAGTGGATGGCAAC<br>CGTCAAATTATAGGATATGTAATAGGAACT<br>CAACAAGCTACCCCAGGGCCCGCATACAGT<br>GGTCGAGAGATAATATACCCCAATGCATCC<br>CTGCTGATCCAGAACATCATCCAGAATGAC<br>ACAGGATTCTACACCCTACACGTCATAAAG<br>TCAGATCTTGTGAATGAAGAAGCAACTGGC<br>CAGTTCCGGGTATACCCGGAGCTGCCCAAG<br>CCCTCCATCTCCAGCAACAACTCCAAACCC<br>GTGGAGGACAAGGATGCTGTGGCCTTCACC<br>TGTGAACCTGAGACTCAGGACGCAACCTAC<br>CTGTGGTGGGTAAACAATCAGAGCCTCCCG<br>GTCAGTCCCAGGCTGCAGCTGTCCAATGGC<br>AACAGGACCCTCACTCTATTCAATGTCACA<br>AGAAATGACACAGCAAGCTACAAATGTGAA<br>ACCCAGAACCCAGTGAGTGCCAGGCGCAGT<br>GATTCAGTCATCCTGAATGTCCTCTATGGC<br>CCGGATGCCCCCACCATTTCCCCTCTAAAC<br>ACATCTTACAGATCAGGGGAAAATCTGAAC<br>CTCTCCTGCCACGCAGCCTCTAACCCACCT<br>GCACAGTACTCTTGGTTTGTCAATGGGACT<br>TTCCAGCAATCCACCCAAGAGCTCTTTATC<br>CCCAACATCACTGTGAATAATAGTGGATCC<br>TATACGTGCCAAGCCCATAACTCAGACACT<br>GGCCTCAATAGGACCACAGTCACGACGATC<br>ACAGTCTATGCACACCATCACCATCACCAT<br>TGAGTCTAGA |
| | SEQ ID NO: 47<br>KLTIESTPFNVAEGKEVLLLVHNLPQHLFG<br>YSWYKGERVDGNRQIIGYVIGTQQATPGPA<br>YSGREIIYPNASLLIQNIIQNDTGFYTLHV<br>IKSDLVNEEATGQFRVYPELPKPSISSNNS<br>KPVEDKDAVAFTCEPETQDATYLWWVNNQS<br>LPVSPRLQLSNGNRTLTLFNVTRNDTASYK<br>CETQNPVSARRSDSVILNVLYGPDAPTISP<br>LNTSYRSGENLNLSCHAASNPPAQYSWFVN<br>GTFQQSTQELFIPNITVNNSGSYTCQAHNS<br>DTGLNRTTVTTITVYAHHHHHH |
| A2-B2-His | SEQ ID NO: 48<br>ATGCACAGCTCAGCACTGCTCTGTTGCCTG<br>GTCCTCCTGACTGGGGTGAGGGCCGAGCCA<br>CCCAAACCCTTCATCACCAGCAACAACTCC<br>AACCCCGTGGAGGATGAGGATGCTGTAGCC<br>TTAACCTGTGAACCTGAGATTCAGAACACA<br>ACCTACCTGTGGTGGGTAAATAATCAGAGC<br>CTCCCGGTCAGTCCCAGGCTGCAGCTGTCC<br>AATGACAACAGGACCCTCACTCTACTCAGT<br>GTCACAAGGAATGATGTAGGACCCTATGAG |

| Extracellular domain | Nucleotide sequence/amino acid sequence (underline indicates signal peptide) |
|---|---|
| | TGTGGAATCCAGAACGAATTAAGTGTTGAC<br>CACAGCGACCCAGTCATCCTGAATGTCCTC<br>TATGGCCCAGACGACCCCACCATTTCCCCC<br>TCATACACCTATTACCGTCCAGGGGTGAAC<br>CTCAGCCTCTCCTGCCATGCAGCCTCTAAC<br>CCACCTGCACAGTATTCTTGGCTGATTGAT<br>GGGAACATCCAGCAACACACAAGAGCTC<br>TTTATCTCCAACATCACTGAGAAGAACAGC<br>GGACTCTATACCTGCCAGGCCAATAACTCA<br>GCCAGTGGCCACAGCAGGACTACAGTCAAG<br>ACAATCACAGTCTCTGCGCACCATCACCAT<br>CACCATTGAGTCTAGA<br><br>SEQ ID NO: 49<br>EPPKPFITSNNSNPVEDEDAVALTCEPEIQ<br>NTTYLWWVNNQSLPVSPRLQLSNDNRTLTL<br>LSVTRNDVGPYECGIQNELSVDHSDPVILN<br>VLYGPDDPTISPSYTYYRPGVNLSLSCHAA<br>SNPPAQYSWLIDGNIQQHTQELFISNITEK<br>NSGLYTCQANNSASGHSRTTVKTITVSAHH<br>HHHH |
| A3-B3-His | SEQ ID NO: 50<br>ATGCACAGCTCAGCACTGCTCTGTTGCCTG<br><u>GTCCTCCTGACTGGGGTGAGGGCCGAGCTG</u><br>CCCAAGCCCTCCATCTCCAGCAACAACTCC<br>AAACTCAGAACACAACCTACCTGTGGTGGG<br>TAAATGGTCAGAGCCTCCCAGTCAGTCCCA<br>GGCTGCAGCTGTCCAATGGCAACAGGACCC<br>TCACTCTATTCAATGTCACAAGAAATGACG<br>CAAGAGCCTATGTATGTGGAATCCAGAACT<br>CAGTGAGTGCAAACCGCAGTGACCCAGTCA<br>CCCTGGATGTCCTCTATGGGCCGGACACCC<br>CCATCATTTCCCCCCAGACTCGTCTTACC<br>TTTCGGGAGCGAACCTCAACCTCTCCTGCC<br>ACTCGGCCTCTAACCCATCCCCGCAGTATT<br>CTTGGCGTATCAATGGGATACCGCAGCAAC<br>ACACACAAGTTCTCTTTATCGCCAAAATCA<br>CGCCAAATAATAACGGGACCTATGCCTGTT<br>TTGTCTCTAACTTGGCTACTGGCCGCAATA<br>ATTCCATAGTCAAGAGCATCACAGTCTCTG<br>CATCTGGAACTTCTCCTGGTCTCTCAGCTC<br>ACCATCACCATCACCATTGAGTCTAGA<br><br>SEQ ID NO: 51<br>ELPKPSISSNNSKPVEDKDAVAFTCEPEAQ<br>NTTYLWWVNGQSLPVSPRLQLSNGNRTLTL<br>FNVTRNDARAYVCGIQNSVSANRSDPVTLD<br>VLYGPDTPIISPPDSSYLSGANLNLSCHSA<br>SNPSPQYSWRINGIPQQHTQVLFIAKITPN<br>NNGTYACFVSNLATGRNNSIVKSITVSASG<br>TSPGLSAHHHHHH |

Figure 4:
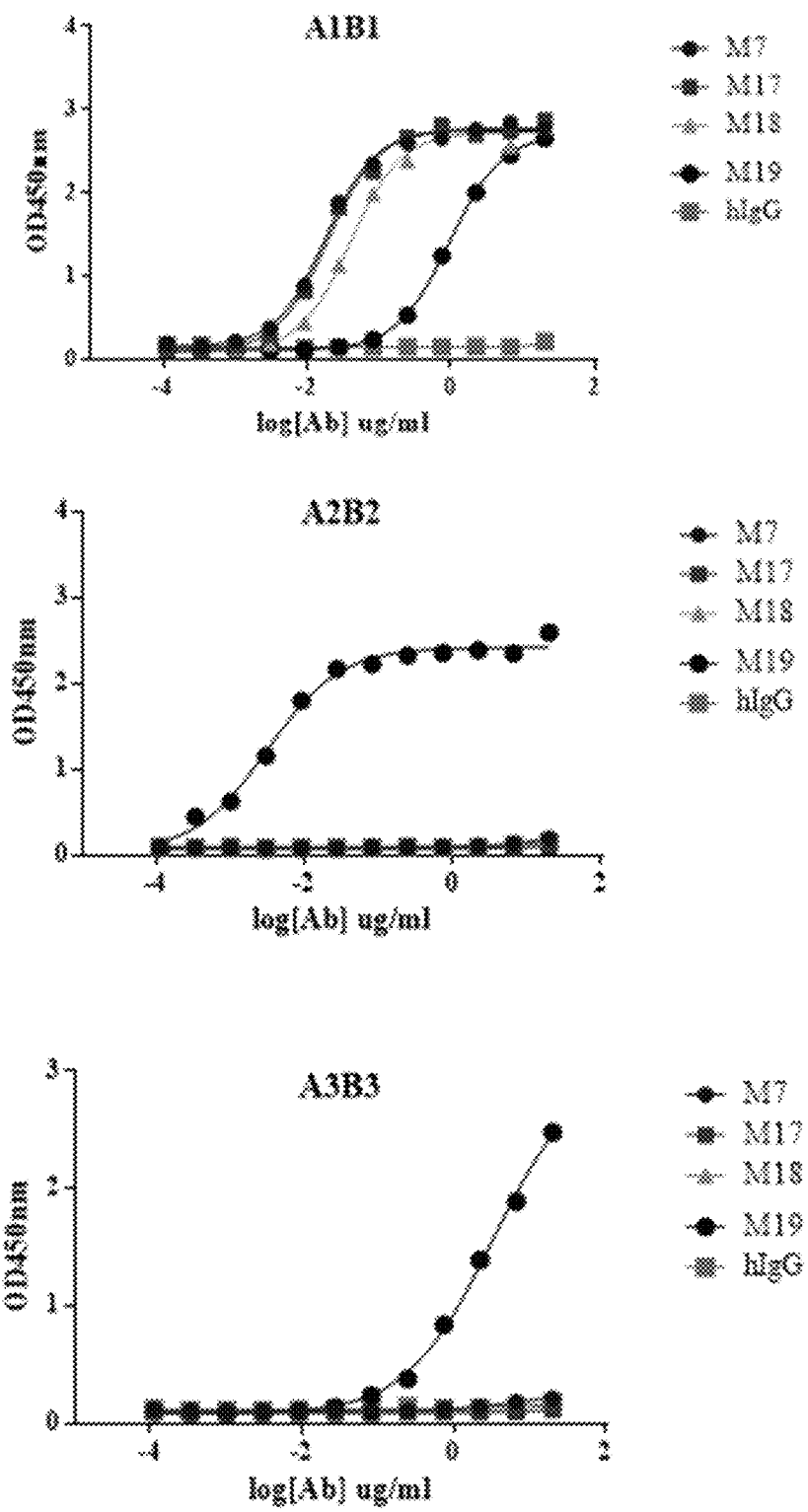

The above CEACAM5 fragment was diluted to 1 μg/ml with DPBS solution, added to a 96-well plate, 100 μl per well, coated overnight at 2-8° C.; the coating solution was discarded, washing was performed twice with PBS solution, PBS solution containing 2% BSA was added, blocking was performed at room temperature for 2 hours; the blocking solution was discarded, antibody diluted in concentration gradient was added, and incubated at 37° C. for 1 hour; the antibody solution was discarded, and washing was performed for 4 times with PBS solution containing 0.05% Tween 20 (PBST solution); anti-human IgG Fc-HRP secondary antibody was added and incubated at 37° C. for 30 minutes; washing was performed for 4 times with PBST solution, TMB chromogenic substrate was added, color development was performed for 5-10 minutes, then the reaction was stopped with an equal volume of 1M H2SO4; the absorbance at 450 nm was read on a microplate reader. The results were shown in FIG. 4.

The epitopes of the above four antibodies M7, M17, M18, and M19 binding to CEACAM5 molecule were as follows:

| Antibody | CEACAM5 domain |
|---|---|
| M7 | A1-B1 |
| M17 | A1-B1 |
| M18 | A1-B1 |
| M19 | A1-B1, A2-B2, A3-B3 |

The above results showed that the M19 antibody could recognize and bind to all three CEACAM5 domains, in which the domain binding EC50 to A2-B2 was the smallest (EC50=0.003 μg/ml), which was much smaller than those of A1-B1 (EC50=0.95 μg/ml) and A3-B3 (EC50=3.23 μg/ml) domain binding; this indicated that the main binding position of the M19 antibody was located in the A2-B2 domain of CEACAM5 molecule, but it could also bind to the A1-B1 and A3-B3 domains, and possibly bind to B1-A2 and B2-A3 domains.

Example 4. FACS Experiment of Antigen Binding

Figure 5:
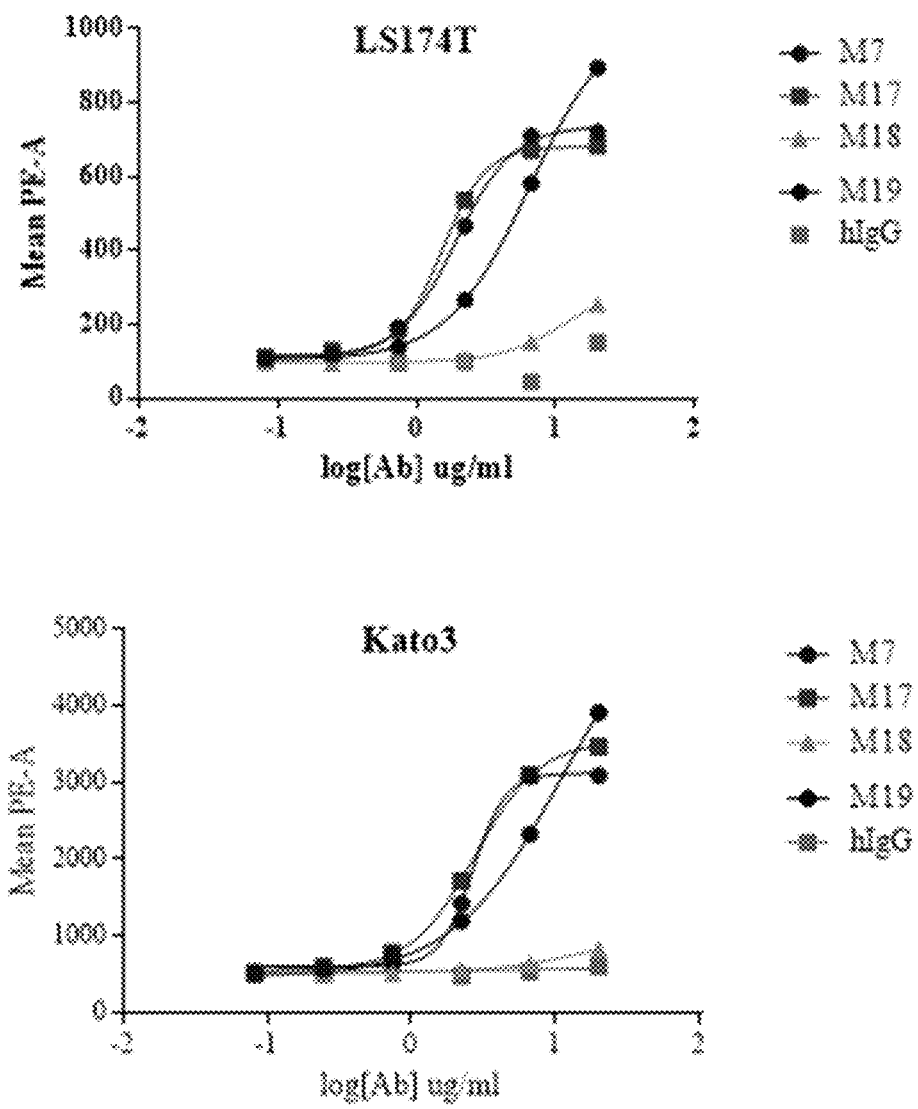

LS174T cells and KATO3 cells (high expression of CEACAM5; ATCC, CL-188) were cultured in RPMI1640 medium containing 10% FBS. After the cells were digested with TrypLE, they were centrifuged and resuspended in DPBS solution containing 2% BSA (FACS buffer solution, 4° C.), and added into a U-bottom 96-well plate, $5 \times 10^5$/100 μl/well, and antibody diluted in concentration gradient was added, incubated at 4° C. for 1 hour, the supernatant was discarded after centrifugation; 100 μl of solution containing anti-human IgG Fc-APC secondary antibody was added and incubated at 4° C. for 1 hour, washing was performed once with FACS buffer, resuspending was performed in 200 μl FACS buffer, and the fluorescence signal value was read on BD CantoII. The results were shown in FIG. 5. The results showed that the above antibodies all bound to LS174T cells and KATO3 cells.

| Antibody | LS174T cell binding EC50, μg/ml | KATO3 cell binding EC50, μg/ml |
|---|---|---|
| M7 | 1.9 | 2.6 |
| M17 | 1.5 | 2.7 |
| M18 | 11.9 | 13.9 |
| M19 | 6.5 | 10.8 |

Example 5. Design and Expression of Humanized Antibody

Comparing the M19 antibody (m2F4) with the IMGT database, the human framework sequence with the highest homology to its VH/VL was selected, and subjected to CDR grafting, and computational chemical simulation was performed to maintain its binding to the antigen. The design of humanized antibody was shown in the following table.

| clone | hAb | V region Nt |
|---|---|---|
| m2F4 | mM19 | >VL<br>(SEQ ID NO: 39)<br>ATGGGCTGGAGCTGCATCATCCTGTTCCTC<br>GTGGCCACAGCTACAGGAGTGCATAGCGAC<br>ATCCAGCTGACCCAGTCTCCTAGCAGCCTG |

| clone | hAb | V region Nt |
|---|---|---|
| | | AGCGCCAGCGTGGGAGATAGAGTGACCATC<br>ACTTGCAGAGCCAGCAGCAGCGTGTCCTAC<br>ATCCATTGGTACCAGCAGAAGCCCCGGCAAG<br>AGCCCTAAGCCTTGGATTCACGGCACCAGC<br>AATCTGGCCAGCGGAGTGCCTAGCAGATTC<br>AGCGGCAGCGGAAGCGGCACCGATTACACC<br>CTGACCATCAGCTCTCTGCAGCCAGAGGAC<br>GCAGCCACCTACTATTGCCAGCAGTGGAGC<br>AGCAACCTGAGCACCTTTGGCCAGGGAACC<br>AAGCTGGAGATCAAG<br><br>(SEQ ID NO: 26)<br>MGWSCHILFLVATATGVHSDIQLTQSPSSL<br>SASVGDRVTITC<u>RASSSVSYIH</u>WYQQKPGK<br>SPKPWIH<u>GTSNLAS</u>GVPSRFSGSGSGTDYT<br>LTISSLQPEDAATYYC<u>QQWSSNLST</u>FGQGT<br>KLEIK<br><br>>VH<br>(SEQ ID NO: 38)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTTCATGAATTGGGTCCGGCAGGCCCCA<br>GGAAAAGCACTCGAGTGGCTGGGACAGATG<br>CGGAACAAGGTCAACGGCGACACCACAGAG<br>TACGCCGAAAGCGTGGAGGGCAGATTCACC<br>ATCAGCCGGGACATCAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 25)<br>MGWSCIILFLVATATGVHSEVQLVESGGGL<br>VQPGGSLRLSCAASGFTFTDYFMNWVRQAP<br>GKALEWLG<u>QMRNKVNGDTTEYAES</u>VEGRFT<br>ISRDISKNSLYLQMNSLKTEDTAVYYCARD<br><u>KGIAYYFDY</u>WGQGTLVTVSS |
| hM19-1 | hAb-003 | >VL<br>(SEQ ID NO: 54)<br>ATGGGCTGGAGCTGCATCATCCTGTTCCTC<br>GTGGCCACAGCTACAGGAGTGCATAGCGAC<br>ATCCAGATGACCCAGAGCCCTAGCAGCCTG<br>AGCGCCAGCGTGGGAGATAGAGTGACCATC<br>ACTTGCAGAGCCAGCAGCAGCGTGTCCTAC<br>ATCCATTGGTACCAGCAGAAGCCCGGCAAG<br>AGCCCTAAGCCCCTGATCTACGGCACCAGC<br>AATCTGGCCAGCGGAGTGCCTAGCAGATTC<br>AGCGGCAGCGGAAGCGGCACCGACTTTACC<br>CTGACCATCAGCTCTCTGCAGCCAGAGGAC<br>GCAGCCACCTACTATTGCCAGCAGTGGAGC<br>AGCAACCTGAGCACCTTTGGCCAGGGAACC<br>AAGCTGGAGATCAAG<br><br>(SEQ ID NO: 70)<br>MGWSCHILFLVATATGVHSDIQMTQSPSSL<br>SASVGDRVTITC<u>RASSSVSYIH</u>WYQQKPGK<br>SPKPLIY<u>GTSNLAS</u>GVPSRFSGSGSGTDFT<br>LTISSLQ<u>P</u>EDAATYYC<u>QQWSSNLST</u>FGQGT<br>KLEIK<br><br>>VH<br>(SEQ ID NO: 55)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTTCATGAATTGGGTCCGGCAGGCCCCA<br>GGAAAAGCACTCGAGTGGGTCGGCTTCATC<br>CGGAACAAGGTCAACGGCGACACCACAGAG<br>TACGCCGAGAGCGTGGAGGGAAGATTCACC<br>ATCAGCCGGGACGACAGCAAGAACAGCCTG<br>TACCTGCAGATGAACAGCCTGAAGACCGAG<br>GATACCGCCGTGTACTATTGCGCCAGGGAC<br>AAGGGCGCCTACTACTTCGACTACTGG<br>GGCCAGGGAACACTGGTGACAGTGTCT<br><br>(SEQ ID NO: 71)<br>MGWSCHILFLVATATGVHSEVQLVESGGGL<br>VQPGGSLRLSCAASGFTFTDYFMNWVRQAP<br>GKALEWVG<u>QMRNKVNGDTTEYAES</u>VEGRFT<br>ISRDDSKNSLYLQMNSLKTEDTAVYYCARD<br><u>KGIAYYFDY</u>WGQGTLVTVSS |
| hM19-3 | hAb-005 | >VL<br>(SEQ ID NO: 56)<br>ATGGGCTGGAGCTGCATCATCCTGTTCCTC<br>GTGGCCACAGCTACAGGAGTGCATAGCGAC<br>ATCCAGTCTGACCCAGTCTCCTAGCAGCCTG<br>AGCGCCAGCGTGGGAGATAGAGTGACCATC<br>ACTTGCAGAGCCAGCAGCAGCGTGTCCTAC<br>ATCCATTGGTACCAGCAGAAGCCCGGCAAG<br>AGCCCTAAGCCTTGGATCTACGGCACCAGC<br>AATCTGGCCAGCGGAGTGCCTAGCAGATTC<br>AGCGGCAGCGGAAGCGGCACCGATTACACC<br>CTGACCATCAGCTCTCTGCAGCCAGAGGAC<br>GCAGCCACCTACTATTGCCAGCAGTGGAGC<br>AGCAACCTGAGCACCTTTGGCCAGGGAACC<br>AAGGTGGAGATCAAG<br><br>(SEQ ID NO: 72)<br>MGWSCIILFLVATATGVHSDIQLTQSPSSL<br>SASVGDRVTITC<u>RASSSVSYIH</u>WYQQKPGK<br>SPKPWIY<u>GTSNLAS</u>GVPSRFSGSGSGTDYT<br>LTISSLQPEDAATYYC<u>QQWSSNLST</u>FGQGT<br>KVEIK<br><br>>VH<br>(SEQ ID NO: 57)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACACCATGTCTTGGGTCCGGCAGGCCACA<br>GGAAAAGCACTCGAGTGGGTCGGCTTCATC<br>CGGAACAAGGTCAACGGCGACACCACAGAG<br>TACAGCGACAGCGTGGAGGGAAGGTTCACC<br>ATCAGCCGGGACAACAGCAAGAACACCCTG<br>TACCTGCAGATGAACAGCCTGCGCGCAGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 73)<br>MGWSCIILFLVATATGVHSEVQLVESGGGL<br>VQPGGSLRLSCAASGFTFTDYTMSWVRQAP<br>GKALEWVG<u>FIRNKVNGDTTEYSDS</u>VEGRFT<br>ISRDNSKNTLYLQMNSLRAEDTAVYYCARD<br><u>KGIAYYFDY</u>WGQGTLVTVSS |
| hM19-4 | hAb-006 | >VL<br>(SEQ ID NO: 58)<br>ATGGGCTGGAGCTGCATCATCCTGTTCCTC<br>GTGGCCACAGCTACAGGAGTGCATAGCGAC<br>ATCGTGCTGTCTCAGTCTCCAGGCACCCTG<br>TCTCTGTCTCCAGGAGAGAGAGCCACCCTG<br>TCTTGTAGAGCCAGCAGCAGCGTGTCCTAC<br>ATCCATTGGTACCAGCAGAAGCCCGGACAG<br>GCTCCTAGACCTTGGATTCACGGCACCAGC<br>AATCTGGCCAGCGGAATCCCCGACAGATTC<br>AGCGGCAGCGGAAGCGGCACCGATTACACC<br>CTGACCATCAGCAGACTGGAGCCAGAGGAC<br>TTCGCCGTGTACTATTGCCAGCAGTGGAGC<br>AGCAATCTGAGCACCTTTGGCGGCGGAACC<br>AAGGTGGAGATCAAG |

| clone | hAb | V region Nt |
|---|---|---|
| | | (SEQ ID NO: 74)<br>MGWSCIILFLVATATGVHSDIVLSQSPGTL<br>SLSPGERATLSCRASSSVSYIHWYQQKPGQ<br>APRPWIHGTSNLASGIPDRFSGSGSGTDYT<br>LTISRLEPEDFAVYYCQQWSSNLSTFGGGT<br>KVEIK<br><br>>VH<br>(SEQ ID NO: 59)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTACATGAATTGGGTCCGGCAGGCCCCA<br>GGAAAAGGACTCGAGTGGCTGGGCTTCATC<br>CGGAACAAGGTCAACGGCGACACCACCGAG<br>TACAGCGCCAGCGTGAAGGGCAGGTTCACC<br>ATCCGGGACATCAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 75)<br>MGWSCIHILFLVATATGVHSEVQLVESGGGL<br>VQPGGSLRLSCAASGFTFTDYYMNWVRQAP<br>GKGLEWLGFIRNKVNGDTTEYSASVKGRFT<br>ISRDISKNSLYLQMNSLKTEDTAVYYCARD<br>KGIAYYFDYWGQGTLVTVSS |
| hM19-7 | hAb-009 | >VL<br>(SEQ ID NO: 52)<br>ATGGGCTGGAGCTGCATCATCCTGTTCCTC<br>GTGGCCACAGCTACAGGAGTGCATAGCGAG<br>ATCGTGCTGACCCAGTCTCCAGCCACACTG<br>AGCGCTTCTCCAGGAGAGAGAGCCACACTG<br>TCTTGTAGAGCCAGCCAGAGCGTGTCCTAC<br>ATCCATTGGTACCAGCAGAAGCCCGGACAG<br>TCTCCTAGGCCTTGGATTCACGGCACAAGC<br>AATCTGGCCACCGGAGTGCCAGCTAGATTC<br>AGCGGCAGCGGAAGCGGCACCGACTTTACC<br>CTGACCATCAGCTCTCTGGAGCCAGAGGAC<br>GCAGCCGTGTACTATTGCCAGCAGTGGAGC<br>AGCAATCTGAGCACCTTTGGCGGCGGAACC<br>AAGGTGGAGATCAAG<br><br>(SEQ ID NO: 68)<br>MGWSCIHILFLVATATGVHSEIVLTQSPATL<br>SASPGERATLSCRASQSVSYIHWYQQKPGQ<br>SPRPWIHGTSNLATGVPARFSGSGSGTDFT<br>LTISSLEPEDAAVYYCQQWSSNLSTFGGGT<br>KVEIK<br><br>>VH<br>(SEQ ID NO: 53)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTACATGAATTGGGTCCGGCAGGCCCCA<br>GGAAAAGCACTCGAGTGGCTGGGCTTCATC<br>CGGAACAAGGTCAACGGCGACACCACAGAG<br>TACGCCGCCAGCGTGAAGGGCAGATTCACC<br>ATCAGCCGGGACGACAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 69)<br>MGWSCIILFLVATATGVHSEVQLVESGGGL<br>VQPGGSLRLSCAASGFTFTDYYMNWVRQAP<br>GKALEWLGFIRNKVNGDTTEYAASVKGRFT |

| clone | hAb | V region Nt |
|---|---|---|
| | | ISRDDSKNSLYLQMNSLKTEDTAVYYCARD<br>KGIAYYFDYWGQGTLVTVSS |
| hM19-8 | hAb-010 | >VL<br>(SEQ ID NO: 60)<br>ATGGGCTGGAGCTGCATCATCCTGTTCCTC<br>GTGGCCACAGCTACAGGAGTGCATAGCGAG<br>ATCGTGCTGACCCAGTCTCCAGCCACACTG<br>AGCGCTTCTCCAGGAGAGAGAGCCACACTG<br>TCTTGCAGAGCCAGCTCTAGCGTGTCCTAC<br>ATCCATTGGTACCAGCAGAAGCCCGGCCAG<br>TCTCCTAGACCCCTGATCTACGGCACCAGC<br>AACAGAGCCACAGGCGTGCCAGCTAGATTC<br>AGCGGCAGCGGAAGCGGCACCGACTTTACC<br>CTGACCATCAGCTCTCTGGAGCCAGAGGAC<br>GCAGCCGTGTACTATTGCCAGCAGTGGAGC<br>AGCAATCTGAGCACCTTTGGCGGCGGAACC<br>AAGGTGGAGATCAAG<br><br>(SEQ ID NO: 76)<br>MGWSCIHILFLVATATGVHSEIVLTQSPATL<br>SASPGERATLSCRASSSVSYIHWYQQKPGQ<br>SPRPLIYGTSNRATGVPARFSGSGSGTDFT<br>LTISSLEPEDAAVYYCQQWSSNLSTFGGGT<br>KVEIK<br><br>>VH<br>(SEQ ID NO: 61)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTACATGGATTGGGTCCGGCAGGCTCCA<br>GGAAAAGCACTCGAGTGGGTCGGCTTCATC<br>CGGAACAAGGTCAACGGCGACACCACAGAG<br>TACGCCGCCAGCGTGAAGGGCAGATTCACC<br>ATCAGCCGGGACGACAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 77)<br>MGWSCIILFLVATATGVHSEVQLVESGGGL<br>VQPGGSLRLSCAASGFTFTDYYMDWVRQAP<br>GKALEWVGFIRNKVNGDTTEYAASVKGRFT<br>ISRDDSKNSLYLQMNSLKTEDTAVYYCARD<br>KGIAYYFDYWGQGTLVTVSS |
| hM19-11 | hAb-013 | >VL<br>(SEQ ID NO: 62)<br>ATGGGCTGGAGCTGCATCATCCTGTTCCTC<br>GTGGCCACAGCTACAGGAGTGCATAGCCAG<br>ATCGTGCTGACCCAGTCTCCAGCCACACTG<br>AGCGCTTCTCCAGGAGAGAGAGCCACACTG<br>TCTTGCAGAGCCAGCTCTAGCGTGTCCTAC<br>ATCCATTGGTACCAGCAGAAGCCCGGACAG<br>AGCCCTAGACCTCTGATCTACGGCACCAGC<br>AATCTGGCCAGCGGAGTGCCAGCTAGATTC<br>AGCGGCAGCGGAAGCGGCACCGACTTTACC<br>CTGACCATCAGCTCTCTGGAGCCAGAGGAC<br>GCAGCCGTGTACTATTGCCAGCAGTGGAGC<br>AGCAATCTGAGCACCTTTGGCGGCGGAACC<br>AAGGTGGAGATCAAG<br><br>(SEQ ID NO: 78)<br>MGWSCIHILFLVATATGVHSQIVLTQSPATL<br>SASPGERATLSCRASSSVSYIHWYQQKPGQ<br>SPRPLIYGTSNLASGVPARFSGSGSGTDFT<br>LTISSLEPEDAAVYYCQQWSSNLSTFGGGT<br>KVEIK<br><br>>VH<br>(SEQ ID NO: 63)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT |

| clone | hAb | V region Nt |
|---|---|---|
| | | TGCGCCGCCAGCGGCTTTACATTCACCGAC<br>TACTACATGGATTGGGTCCGGCAGGCTCCA<br>GGAAAAGCACTCGAGTGGGTCGGCTTCACC<br>CGGAACAAGGTCAACGGCGACACCACAGAG<br>TACGCCGCCAGCGTGAAGGGCAGATTCACC<br>ATCAGCCGGGACGACAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 79)<br>MGWSCIILFLVATATGVHSEVQLVESGGGL<br>VQPGGSLRLSCAASGFTFTDYYMDWVRQAP<br>GKALEWVGFTRNKVNGDTTEYAASVKGRFT<br>ISRDDSKNSLYLQMNSLKTEDTAVYYCARD<br>KGIAYYFDYWGQGTLVTVSS |
| hM19-14 | hAb-016 | >VL<br>(SEQ ID NO: 64)<br>ATGGGCTGGAGCTGCATCATCCTGTTCCTC<br>GTGGCCACAGCTACAGGAGTGCATAGCGAG<br>ATCGTGCTGACCCAGTCTCCAGGCACACTG<br>AGCGCTTCTCCAGGAGAGAGAGCCACACTG<br>TCTTGCAGAGCCAGCTCTAGCGTGTCCTAC<br>ATCCATTGGTACCAGCAGAAGCCCGGACAG<br>AGCCCTAGACCTCTGATCTACGGCACCAGC<br>AATCTGGCCAGCGGAGTGCCAGACGATTC<br>AGCGGCAGCGGAAGCGGCACCGACTTTACC<br>CTGACCATCAGCAGACTGGAGCCAGAGGAC<br>GCAGCCGTGTACTATTGCCAGCAGTGGAGC<br>AGCAATCTGAGCACCTTTGGCGGCGGAACC<br>AAGGTGGAGATCAAG<br><br>(SEQ ID NO: 80)<br>MGWSCHILFLVATATGVHSEIVLTQSPGTL<br>SASPGERATLSCRASSSVSYIHWYQQKPGQ<br>SPRPLIYGTSNLASGVPDRFSGSGSGTDFT<br>LTISRLEPEDAAVYYCQQWSSNLSTFGGGT<br>KVEIK<br><br>>VH<br>(SEQ ID NO: 65)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTACATGGATTGGGTCCGGCAGGCTCCA<br>GGAAAAGCACTCGAGTGGGTCGGCTTCACC<br>CGGAACAAGGTCAACGGCGACACCACAGAG<br>TACGCCGCCAGCGTGAAGGGCAGATTCACC<br>ATCAGCCGGGACGACAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 81)<br>MGWSCHILFLVATATGVHSEVQLVESGGGL<br>VQPGGSLRLSCAASGFTFTDYYMDWVRQAP<br>GKALEWVGFTRNKVNGDTTEYAASVKGRFT<br>ISRDDSKNSLYLQMNSLKTEDTAVYYCARD<br>KGIAYYFDYWGQGTLVTVSS |
| hM19-15 | hAb-017 | >VL<br>(SEQ ID NO: 66)<br>ATGGGCTGGAGCTGCATCATCCTGTTCCTC<br>GTGGCCACAGCTACAGGAGTGCATAGCGAG<br>ATCGTGCTGACCCAGTCTCCAGCCACACTG<br>AGCGCTTCTCCAGGAGAGAGAGCCACACTG<br>TCTTGCAGAGCCAGCTCTAGCGTGTCCTAC<br>ATCCATTGGTACCAGCAGAAGCCCGGCCAG<br>TCTCCTAGACCTCTGATCTACGGCGCCAGC<br>AATCTGGCCAGCGGCGTGCCAGCCAGATTC<br>AGCGGAAGCGGCAGCGGCACCGACTTTACC<br>CTGACCATCAGCTCTCTGGAGCCAGAGGAC<br>GCAGCCGTGTACTATTGCCAGCAGTGGAGC<br>AGCAATCTGAGCACCTTTGGCGGCGGAACC<br>AAGGTGGAGATCAAG<br><br>(SEQ ID NO: 82)<br>MGWSCIILFLVATATGVHSEIVLTQSPATL<br>SASPGERATLSCRASSSVSYIHWYQQKPGQ<br>SPRPLIYGASNLASGVPARFSGSGSGTDFT<br>LTISSLEPEDAAVYYCQQWSSNLSTFGGGT<br>KVEIK<br><br>>VH<br>(SEQ ID NO: 67)<br>ATGGGCTGGAGCTGCATCATCCTGTTCCTC<br>GTGGCCACAGCTACAGGAGTGCATAGCGAG<br>GTGCAGCTGGTGGAATCAGGAGGAGGACTG<br>GTGCAGCCAGGAGGATCTCTGAGACTGTCT<br>TGCGCCGCCAGCGGCTTTACATTCACCGAC<br>TACTACATGGATTGGGTCCGGCAGGCTCCA<br>GGAAAAGCACTCGAGTGGGTCGGCTTCACC<br>CGGAACAAGGTCAACGGCGACACCACAGAG<br>TACGCCGCCAGCGTGAAGGGCAGATTCACC<br>ATCAGCCGGGACGACAGCAAGAACAGCCTG<br>TACCTGCAGATGAACAGCCTGAAGACCGAG<br>GATACCGCCGTGTACTATTGCGCCAGGGAC<br>AAGGGCATCGCCTACTACTTCGACTACTGG<br>GGCCAGGGAACACTGGTGACAGTGTCT<br><br>(SEQ ID NO: 83)<br>MGWSCHILFLVATATGVHSEVQLVESGGGL<br>VQPGGSLRLSCAASGFTFTDYYMDWVRQAP<br>GKALEWVGFTRNKVNGDTTEYAASVKGRFT<br>ISRDDSKNSLYLQMNSLKTEDTAVYYCARD<br>KGIAYYFDYWGQGTLVTVSS |

The VH and VL regions of the above antibodies were linked to the human IgG1 Fc region and the kappa constant region, and the heavy chain and light chain sequences of the antibody were inserted into the pcDNA3.4 vector, transiently expressed in 293 cells, and purified by protein A or G.

Example 6. ELISA Binding Experiment of Humanized Antibody

Figure 6:
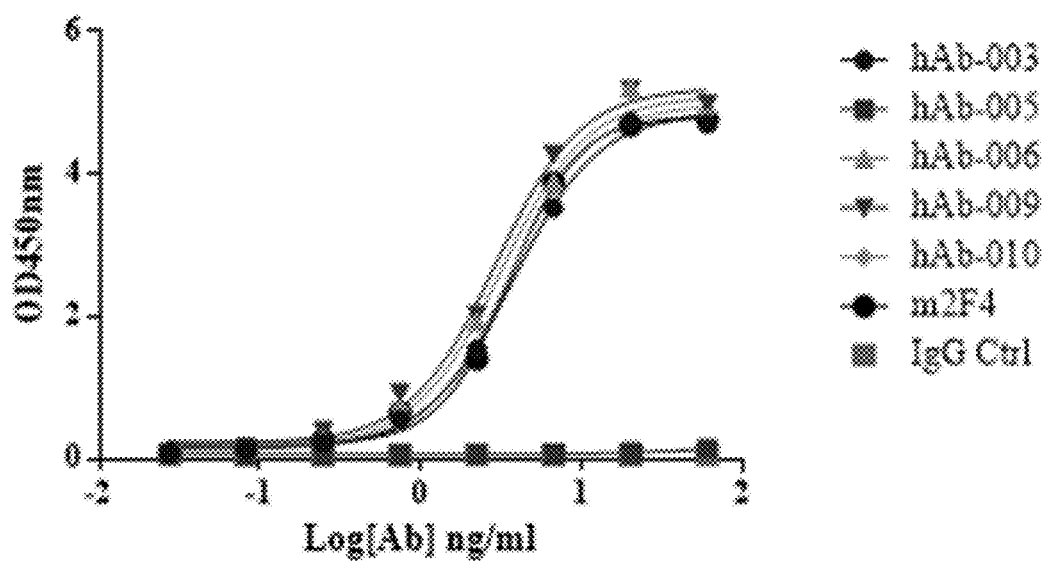
Figure 6:
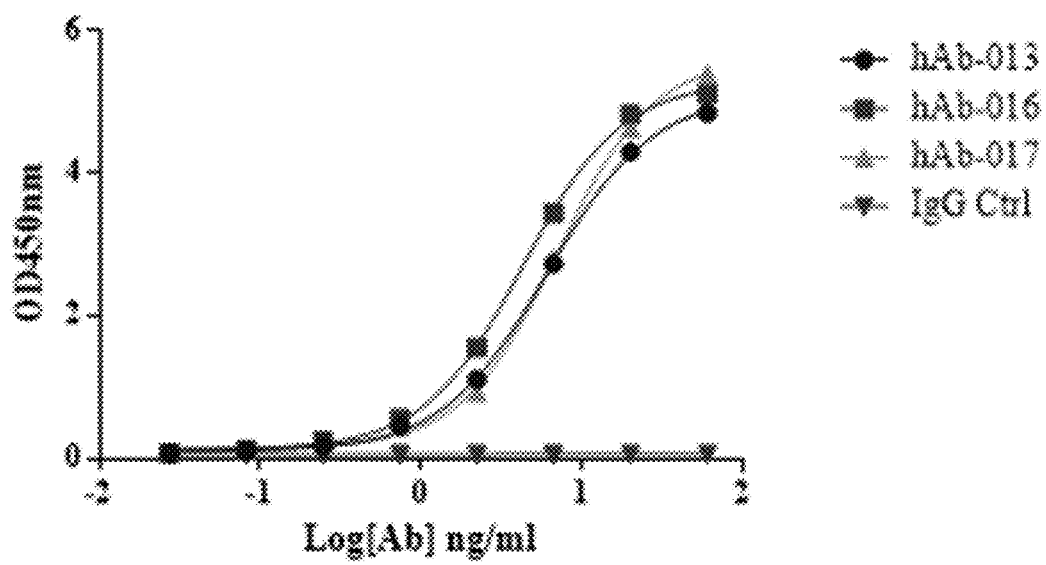

Recombinant CEACAM5 antigen (Sinobiological, 11077-H08H) was diluted to 1 μg/ml with DPBS solution, add into a 96-well plate, 100 μl per well, and coated overnight at 2-8° C.; the coating solution was discarded, washing was performed twice with PBS solution, PBS solution containing 2% BSA was added, and blocking was performed at room temperature for 2 hours; the blocking solution was discarded, the humanized antibody diluted in concentration gradient was added, and incubated at 37° C. for 1 hour; the antibody solution was discarded, and washing was performed for 4 times with PBS solution containing 0.05% Tween 20 (PBST solution); the anti-human IgG Fc-HRP secondary antibody was added and incubated at 37° C. for 30 minutes; washing was performed for 4 times with PBST solution, TMB chromogenic substrate was added, and color development was carried out for 5-10 minutes, then the reaction was terminated by adding equal volume of 1M H2SO4; the absorbance at 450 nm was read on a microplate reader. The binding results of the above humanized antibodies to CEACAM5 recombinant protein were shown in FIG. 6. The results showed that: except hAb-005 antibody, other humanized antibodies could bind CEACAM5-His antigen.

| Humanized antibody | EC50 µg/ml |
| --- | --- |
| M2F4 | 3.53 |
| hAb-003 | 3.69 |
| hAb-005 | No binding |
| hAb-006 | 3.11 |
| hAb-009 | 2.87 |
| hAb-010 | 3.56 |
| hAb-013 | 6.10 |
| hAb-016 | 4.32 |
| hAb-017 | 7.05 |

Example 7. Cell Binding Experiment of Humanized Antibody

Figure 7:
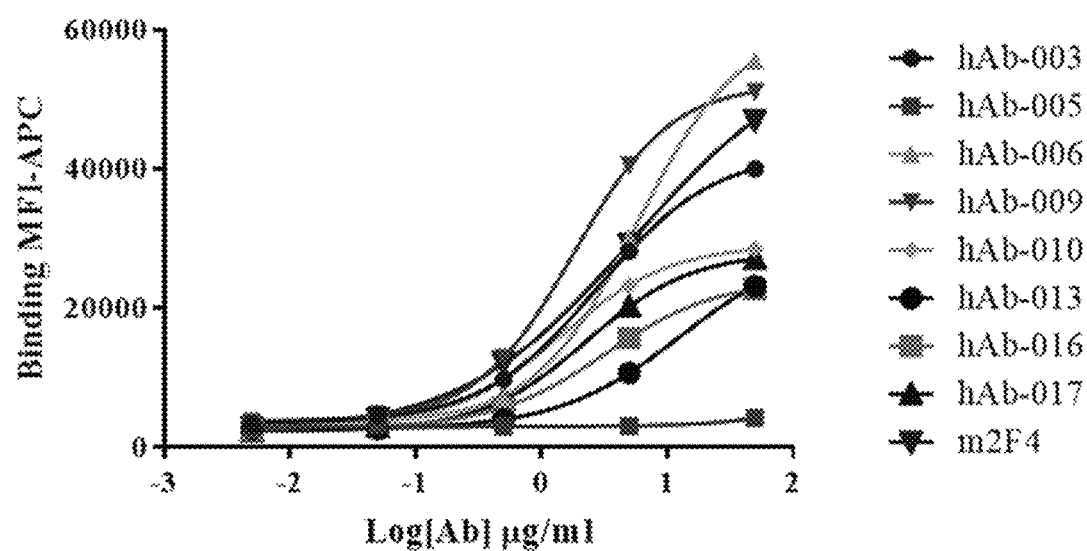

KATO3 cells (high expression of CEACAM5) were cultured in RPMI1640 medium containing 10% FBS. After the cells were digested with TrypLE trypsin, they were centrifuged and resuspended in DPBS solution containing 2% BSA (FACS buffer, 4° C.), and added to a U-bottom 96-well plate, 5×10$^5$/100 µl/well, the antibody diluted in concentration gradient was added, incubated at 4° C. for 1 hour, the supernatant was discarded after centrifugation; 100 of µl solution containing anti-human IgG Fc-APC secondary antibody was added to each well and incubated at 4° C. for 1 hour, then washing was performed with FACS buffer once, resuspending was performed in 200 µl of FACS buffer, and the fluorescence signal value was read on BD C6 plus. The results were shown in FIG. 7.

The EC50 and Emax of humanized antibody binding to KATO3 cells were shown in the table below

| Antibody | EC50, µg/ml | Emax |
| --- | --- | --- |
| m2F4-hIgG1 | 5.3 | 100% |
| hAb-003 | 2.7 | 85.1% |
| hAb-005 | 3250 | 9.1% |
| hAb-006 | 5.7 | 118.2% |
| hAb-009 | 1.8 | 108.6% |
| hAb-010 | 1.3 | 60.6% |
| hAb-013 | 12.7 | 49.3% |
| hAb-016 | 3.2 | 48.4% |
| hAb-017 | 2.2 | 57.7% |

The above results showed that hAb-005 lost its ability of binding to CEACAM5 protein and KATO3 cell line; in which hAb-009 humanized antibody had the strongest binding ability to KATO3 cells and maintained the maximum binding.

Example 8. Experiment of Blocking Antibody Binding

Figure 8:
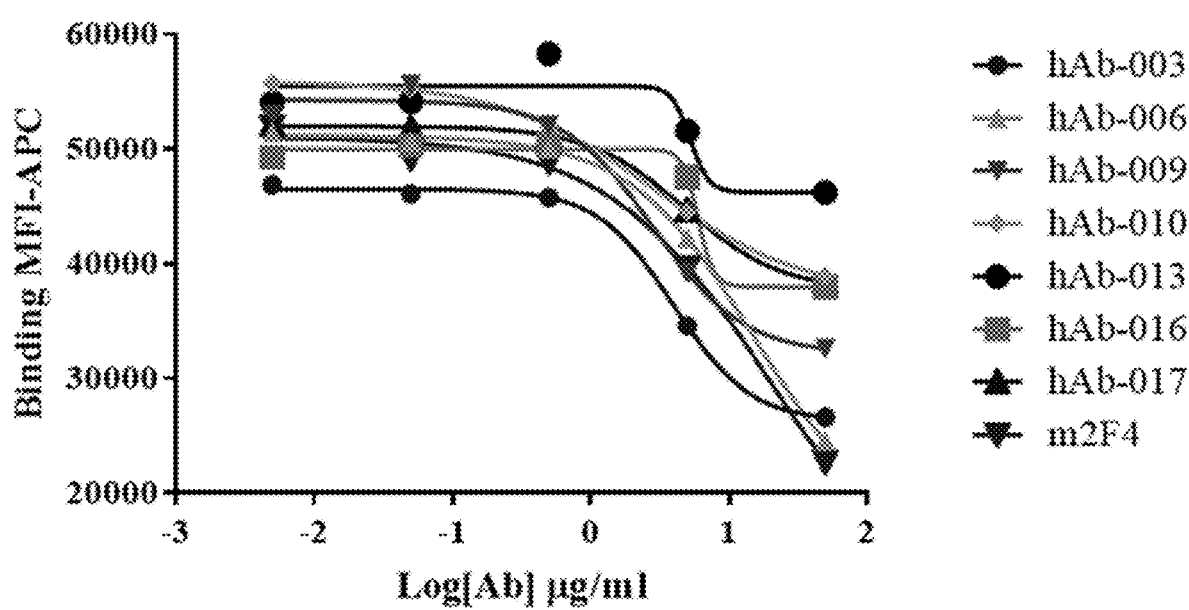

KATO3 cells (high expression of CEACAM5) were cultured in RPMI1640 medium containing 10% FBS. After the cells were digested with TrypLE trypsin, they were centrifuged and resuspended in DPBS solution containing 2% BSA (FACS buffer, 4° C.), and added a U-bottom 96-well plate, 5×10$^5$/100 µl/well, the mouse monoclonal antibody M19 antibody (m2F4) was added to 1 µg/ml and the humanized antibody diluted in gradient (50 µg/ml, 3-fold dilution) was added, then incubated at 4° C. for 1 hour, the supernatant was discarded after centrifugation; 100 µl of solution containing anti-mouse IgG Fc-APC secondary antibody was added to each well and incubated at 4° C. for 1 hour, washing was performed once with FACS buffer, resuspending was performed in 200 µl FACS buffer, and the fluorescence signal value was read on BD C6 plus. The results were shown in FIG. 8.

The results of humanized antibodies blocking mouse monoclonal antibody M19 antibody (m2F4) binding were shown in the table below.

| Antibody | IC50, µg/ml | Emax Inhibition, % |
| --- | --- | --- |
| m2F4-hIgG1 | 6.6 | 43.7% |
| hAb-003 | 3.9 | 51.3% |
| hAb-005 | ND | ND |
| hAb-006 | 6.9 | 47.2% |
| hAb-009 | 2.7 | 62.7% |
| hAb-010 | 2.3 | 75.0% |
| hAb-013 | 5.2 | 89.0% |
| hAb-016 | 6.4 | 73.2% |
| hAb-017 | 4.5 | 73.9% |

The above results showed that the hAb-003, hAb-006, hAb-009, hAb-010, hAb-013, hAb-016, hAb-017 antibodies could compete with the m2F4 antibody, indicating that they could bind to the same epitope on the CEACAM5 molecule.

What is claimed is:

1. A humanized antibody or antigen-binding fragment thereof specifically binding to glycosylated CEACAM5, wherein the antibody comprises a light chain variable region and a heavy chain variable region, wherein:
the light chain variable region comprises: CDR-L1 as set forth in SEQ ID NO: 84, CDR-L2 as set forth in SEQ ID NO: 85 and CDR-L3 as set forth in SEQ ID NO: 86; and the heavy chain variable region comprises: CDR-H1 as set forth in SEQ ID NO: 87, CDR-H2 as set forth in SEQ ID NO: 88 and CDR-H3 as set forth in SEQ ID NO: 89.

2. The humanized antibody or antigen-binding fragment thereof according to claim 1, wherein the light chain variable region comprises an amino acid sequence having at least 90% identity to the amino acid sequence of SEQ ID NO: 68, and wherein the heavy chain variable region comprises an amino acid sequence having at least 90% identity to the amino acid sequence of SEQ ID NO: 69.

3. A pharmaceutical composition, which comprises the antibody or antigen-binding fragment thereof according to claim 1 and a pharmaceutically acceptable carrier.

4. The humanized antibody or antigen-binding fragment thereof according to claim 2, wherein the antibody comprises: a light chain variable region encoded by the nucleotide sequence of SEQ ID NO: 52, and a heavy chain variable region encoded by the nucleotide sequence of SEQ ID NO: 53.

5. The humanized antibody or antigen-binding fragment thereof according to claim 2, wherein the antibody comprises a light chain variable region having the amino acid sequence SEQ ID NO: 68 and a heavy chain variable region having the amino acid sequence SEQ ID NO: 69.

* * * * *